US011612118B2

(12) United States Patent
Gonzalez et al.

(10) Patent No.: US 11,612,118 B2
(45) Date of Patent: Mar. 28, 2023

(54) BIOMASS PRODUCTION

(71) Applicant: POND TECHNOLOGIES INC., Markham (CA)

(72) Inventors: Jaime A. Gonzalez, Oakville, CA (US); Max Kolesnik, Toronto (CA); Steven C. Martin, Toronto (CA); Tony Di Pietro, Brampton (CA); Emidio Di Pietro, Brampton (CA)

(73) Assignee: Pond Technologies Inc., Markham (CA)

( * ) Notice: Subject to any disclaimer, the term of this patent is extended or adjusted under 35 U.S.C. 154(b) by 0 days.

(21) Appl. No.: 15/234,462

(22) Filed: Aug. 11, 2016

(65) Prior Publication Data

US 2017/0118932 A1    May 4, 2017

Related U.S. Application Data

(63) Continuation of application No. 13/327,541, filed on Dec. 15, 2011, now abandoned, and a continuation-in-part of application No. PCT/CA2011/001367, filed on Nov. 18, 2011, and a continuation-in-part of application No. PCT/CA2011/000574, filed on May 18, 2011, which is a continuation-in-part of application No. 13/022,396, filed on Feb. 7, 2011, now abandoned, which is a continuation-in-part of application No. 12/784,172, filed on May 20, 2010, now Pat. No. 8,940,520, said application No. PCT/CA2011/000574 is a continuation-in-part of application No. 12/784,172, filed on May 20, 2010, now Pat. No. 8,940,520, and a continuation-in-part of application No. 12/784,181, filed on May 20, 2010, now abandoned, and a continuation-in-part of application No. 12/784,215, filed on May 20, 2010, now Pat. No. 8,969,067, and a continuation-in-part of application No. 12/784,141, filed on May 20, 2010, now abandoned, and a continuation-in-part of application No. 12/784,106, filed on May 20, 2010, now abandoned, and a continuation-in-part of application No. 12/784,126, filed on May 20, 2010, now Pat. No. 8,889,400.

(30) Foreign Application Priority Data

Apr. 29, 2011    (CA) .................................. CA 2738516

(51) Int. Cl.
*A01G 33/00*     (2006.01)
*C12N 1/12*      (2006.01)

(52) U.S. Cl.
CPC .............. *A01G 33/00* (2013.01); *C12N 1/12* (2013.01); *Y02P 60/20* (2015.11)

(58) Field of Classification Search
None
See application file for complete search history.

(56) References Cited

U.S. PATENT DOCUMENTS

| 2,658,310 | A | 11/1953 | Cook ................................. 435/3 |
| 2,715,795 | A | 8/1955 | Pallotta et al. ............ 435/257.3 |
| 2,732,661 | A | 1/1956 | Spoehr et al. ................... 47/1.4 |
| 2,732,663 | A | 1/1956 | Dewey ............................. 47/1.4 |
| 2,815,607 | A | 12/1957 | Schroeder ....................... 47/1.4 |
| 2,854,792 | A | 10/1958 | Juda ........................... 435/257.3 |
| 3,224,143 | A | 12/1965 | Tew et al. ..................... 435/168 |
| 3,243,918 | A | 4/1966 | Machiedo ................. 435/257.3 |
| 3,303,608 | A | 2/1967 | Hannan ......................... 435/168 |
| 3,403,471 | A | 10/1968 | Clement et al. ................ 47/1.4 |
| 3,504,185 | A | 3/1970 | Zweig et al. ................. 250/565 |
| 3,650,068 | A | 3/1972 | Meyer et al. .................... 47/1.4 |
| 3,712,025 | A | 1/1973 | Wallace ........................... 95/68 |

(Continued)

FOREIGN PATENT DOCUMENTS

| CA | 2738397 | 11/2011 |
| CA | 2738410 | 11/2011 |

(Continued)

OTHER PUBLICATIONS

Hall et al., Growth Rates Made Easy, Mol. Biol. Evol. 31(1): 232-238, 2013.*
Huang et al., Water Res., 43:3009-3018 (2009) (Year: 2009).*
Poulet et al, Marine Biol., 77:93-100 (1983) (Year: 1983).*
FAO (http://www.fao.org/3/w3732e/w3732e06.htm (Accessed Dec. 18, 2019) (Year: 2019).*
Thornton et al., Study Group Report, pp. 54-85 (2010) (Year: 2010).*
Doshi, Thesis (2016) (Year: 2006).*
Taiwan IPO, Office Action for TW Application No. 100142764 dated Oct. 27, 2016.
A Preliminary Experiment on Enclosed and Continuous Culture of Marine Microalgae.

(Continued)

*Primary Examiner* — David W Berke-Schlessel
(74) *Attorney, Agent, or Firm* — Ridout & Maybee LLP

(57) ABSTRACT

A process of growing a phototrophic biomass in a reaction zone, including a reaction mixture that is operative for effecting photosynthesis upon exposure to photosynthetically active light radiation, is provided. The reaction mixture includes phototrophic biomass that is operative for growth within the reaction zone. In one aspect, the carbon dioxide supply is modulated in response to detected process parameters. In another aspect, inputs to the reaction zone are modulated based on changes to the carbon dioxide supply. In another aspect, dilution of the carbon dioxide-comprising supply is effected. In another aspect, pressure of the carbon dioxide-comprising supply is increased. In another aspect, water is condensed from the carbon dioxide-comprising supply and recovered for re-use. In another aspect, the produced phototrophic biomass is harvested at a rate which approximates a predetermined mass growth rate of the phototrophic biomass.

7 Claims, 7 Drawing Sheets

(56) References Cited

U.S. PATENT DOCUMENTS

| | | | |
|---|---|---|---|
| 3,763,824 A | 10/1973 | Schoon | 119/242 |
| 3,855,121 A | 12/1974 | Gough | 210/610 |
| 3,882,635 A | 5/1975 | Yamanaka et al. | 435/257.1 |
| 3,959,923 A | 6/1976 | Selke | 47/1.4 |
| 3,986,297 A | 10/1976 | Ichimura et al. | 435/292.1 |
| 4,043,903 A | 8/1977 | Dor | 47/1.4 |
| 4,078,331 A | 3/1978 | Savins et al. | 435/101 |
| 4,084,346 A | 4/1978 | Stengel et al. | 435/292.1 |
| 4,087,936 A | 5/1978 | Savins et al. | 47/1.4 |
| 4,116,778 A | 9/1978 | Belousov et al. | 435/287.1 |
| 4,235,043 A | 11/1980 | Harasawa et al. | 47/1.4 |
| 4,253,271 A | 3/1981 | Raymond | 47/1.4 |
| 4,267,038 A | 5/1981 | Thompson | 210/602 |
| 4,297,000 A | 10/1981 | Fries | 362/557 |
| 4,324,068 A | 4/1982 | Anthony | 47/1.4 |
| 4,341,038 A | 7/1982 | Bloch et al. | 47/1.4 |
| 4,383,039 A | 5/1983 | Leavitt | 435/107 |
| 4,398,926 A | 8/1983 | Doshi | 95/55 |
| 4,417,415 A | 11/1983 | Cysewski et al. | 47/1.4 |
| 4,438,591 A | 3/1984 | Kessler | 47/1.4 |
| 4,442,211 A | 4/1984 | Greenbaum | 435/168 |
| 4,473,970 A | 10/1984 | Hills | 47/1.4 |
| 4,525,031 A | 6/1985 | Mori | 359/597 |
| 4,539,625 A | 9/1985 | Bornstein et al. | 362/576 |
| 4,595,405 A | 6/1986 | Agrawal et al. | 62/646 |
| 4,626,065 A | 12/1986 | Mori | 385/25 |
| 4,676,956 A | 6/1987 | Mori | 422/186 |
| 4,681,612 A | 7/1987 | O'Brien et al. | 62/624 |
| 4,724,214 A | 2/1988 | Mori | 435/292.1 |
| 4,781,843 A | 11/1988 | Baker et al. | 210/764 |
| 4,851,339 A | 7/1989 | Hills | 435/67 |
| 4,865,969 A | 9/1989 | Amen et al. | 435/3 |
| 4,869,017 A | 9/1989 | Bird et al. | 47/1.4 |
| 4,889,812 A | 12/1989 | Guinn et al. | 435/286.7 |
| 4,900,678 A | 2/1990 | Mori | 435/292.1 |
| 4,939,087 A | 7/1990 | Van Wie et al. | 435/394 |
| 4,952,511 A | 8/1990 | Radmer | 435/292.1 |
| 4,958,460 A | 9/1990 | Nielson et al. | 47/1.4 |
| 4,970,166 A | 11/1990 | Mori | 435/292.1 |
| 4,995,377 A | 2/1991 | Eiden | |
| 5,040,486 A | 8/1991 | Pack | 119/215 |
| 5,081,036 A | 1/1992 | Familletti | 435/296.1 |
| 5,104,803 A | 4/1992 | Delente | 435/292.1 |
| 5,151,342 A | 9/1992 | Wiedemann | 430/270.17 |
| 5,151,347 A | 9/1992 | Delente et al. | 435/3 |
| 5,206,173 A | 4/1993 | Finn | 435/290.1 |
| 5,216,976 A | 6/1993 | Marinkovich | 119/200 |
| 5,330,915 A | 7/1994 | Wilson et al. | 435/286.6 |
| 5,334,497 A | 8/1994 | Inaba et al. | 435/3 |
| 5,358,858 A | 10/1994 | Chiang et al. | 435/71.1 |
| 5,424,209 A | 6/1995 | Kearney | 435/286.5 |
| 5,447,629 A | 9/1995 | Chaumont et al. | 210/96.1 |
| 5,534,404 A | 7/1996 | Laurance et al. | 435/3 |
| 5,534,417 A | 7/1996 | Arad et al. | 435/67 |
| 5,541,056 A | 7/1996 | Huntley et al. | 435/3 |
| 5,552,058 A | 9/1996 | Fanning | 210/669 |
| 5,558,984 A | 9/1996 | Young et al. | 435/3 |
| 5,565,108 A | 10/1996 | Dimesky et al. | 210/750 |
| 5,573,669 A | 11/1996 | Jensen | 210/602 |
| 5,578,472 A | 11/1996 | Ueda et al. | 435/161 |
| 5,614,378 A | 3/1997 | Yang et al. | 435/41 |
| 5,656,421 A | 8/1997 | Gebhard et al. | 435/3 |
| 5,659,977 A | 8/1997 | Jensen et al. | 34/547 |
| 5,670,046 A | 9/1997 | Kimmel | 210/602 |
| 5,682,709 A | 11/1997 | Erickson | 47/58.1 R |
| 5,686,299 A | 11/1997 | Colwell et al. | 435/287.1 |
| 5,711,983 A | 1/1998 | Kyle et al. | 426/635 |
| 5,741,702 A | 4/1998 | Lorenz | 435/292.1 |
| 5,744,041 A | 4/1998 | Grove | 210/602 |
| 5,776,349 A | 7/1998 | Guelcher et al. | 210/703 |
| 5,843,762 A | 12/1998 | Moll | 435/257.1 |
| 5,846,435 A | 12/1998 | Haase | 210/727 |
| 5,846,816 A | 12/1998 | Forth | 435/292.1 |
| 5,851,398 A | 12/1998 | Adey | 210/602 |
| 5,871,952 A | 2/1999 | Ghirardi et al. | 435/34 |
| 5,882,849 A | 3/1999 | Leonard et al. | 435/3 |
| 5,897,997 A | 4/1999 | Louvel | 435/294.1 |
| 5,906,750 A | 5/1999 | Haase | 210/727 |
| 5,910,254 A | 6/1999 | Guelcher et al. | 210/703 |
| 5,912,113 A | 7/1999 | Nakamura et al. | 435/3 |
| 5,951,875 A | 9/1999 | Kanel et al. | 210/703 |
| 5,958,761 A | 9/1999 | Yogev et al. | 435/292.1 |
| 5,981,260 A | 11/1999 | Metz | 435/243 |
| 5,981,271 A | 11/1999 | Doucha et al. | 435/292.1 |
| 5,994,129 A | 11/1999 | Armstrong et al. | 435/325 |
| 6,000,551 A | 12/1999 | Kanel et al. | 209/164 |
| 6,022,701 A | 2/2000 | Boussiba et al. | 435/67 |
| 6,083,740 A | 7/2000 | Kodo et al. | 435/266 |
| 6,110,370 A | 8/2000 | Van Hille et al. | 210/602 |
| 6,120,690 A | 9/2000 | Haase | 210/728 |
| 6,128,135 A | 10/2000 | Stiles et al. | 359/597 |
| 6,140,365 A | 10/2000 | Kiy et al. | 514/560 |
| 6,156,561 A | 12/2000 | Kodo et al. | 435/257.1 |
| 6,174,720 B1 | 1/2001 | Oxley et al. | 435/293.1 |
| 6,228,332 B1 | 5/2001 | Dunn et al. | 422/186.3 |
| 6,237,284 B1 | 5/2001 | Erickson | 47/58.1 R |
| 6,258,588 B1 | 7/2001 | Demetropoulos et al. | 435/257.1 |
| 6,284,453 B1 | 9/2001 | Siano | 435/3 |
| 6,287,852 B1 | 9/2001 | Kondo et al. | 435/292.1 |
| 6,299,774 B1 | 10/2001 | Ainsworth et al. | 210/603 |
| 6,348,347 B1 | 2/2002 | Hirabayashi et al. | 435/292.1 |
| 6,391,238 B1 | 5/2002 | Sato et al. | 264/141 |
| 6,477,841 B1 | 11/2002 | Yantovsky | 60/641.8 |
| 6,492,149 B1 | 12/2002 | Muller-Feuga | 435/173.8 |
| 6,509,188 B1 | 1/2003 | Trosch et al. | 435/292.1 |
| 6,524,486 B2 | 2/2003 | Borodyanski et al. | 210/703 |
| 6,571,735 B1 | 6/2003 | Wilkinson | 119/215 |
| 6,579,714 B1 | 6/2003 | Hirabayashi et al. | 435/292.1 |
| 6,602,703 B2 | 8/2003 | Dutil | 435/292.1 |
| 6,603,069 B1 | 8/2003 | Muhs et al. | 136/246 |
| 6,633,042 B1 | 10/2003 | Funken et al. | 250/435 |
| 6,648,949 B1 | 11/2003 | Der et al. | 96/316 |
| 6,667,171 B2 | 12/2003 | Bayless et al. | 435/292.1 |
| 6,673,532 B2 | 1/2004 | Rao | 435/4 |
| 6,673,592 B1 | 1/2004 | Wang et al. | 435/257.1 |
| 6,709,862 B2 | 3/2004 | Curtis | 435/325 |
| 6,792,336 B1 | 9/2004 | Johnson et al. | 700/266 |
| 6,815,204 B2 | 11/2004 | Muller-Feuga et al. | 435/393 |
| 6,830,699 B2 | 12/2004 | Heidal | 210/748.12 |
| 6,851,387 B2 | 2/2005 | Unterrneyer et al. | 119/212 |
| 6,858,430 B1 | 2/2005 | Reddy et al. | 435/420 |
| 6,887,692 B2 | 5/2005 | Paterek | 435/168 |
| 6,918,354 B2 | 7/2005 | Perriello | 119/231 |
| 6,929,942 B2 | 8/2005 | Moghe et al. | 435/262.5 |
| 6,936,459 B1 | 8/2005 | Venkatesh et al. | 435/257.1 |
| 6,989,252 B2 | 1/2006 | Melis et al. | 435/168 |
| 6,991,919 B1 | 1/2006 | Porter et al. | 435/41 |
| 7,001,519 B2 | 2/2006 | Linden et al. | 210/602 |
| 7,022,232 B2 | 4/2006 | Jensen | 210/602 |
| 7,033,823 B2 | 4/2006 | Chang | 435/297.2 |
| 7,056,725 B1 | 6/2006 | Lu | 435/292.1 |
| 7,135,308 B1 | 11/2006 | Bush et al. | 435/42 |
| 7,135,332 B2 | 11/2006 | Ouellette | 435/290.1 |
| 7,153,344 B2 | 12/2006 | Filippi et al. | 95/51 |
| 7,163,811 B2 | 1/2007 | Behrens et al. | 435/134 |
| 7,172,691 B2 | 2/2007 | Dunlop et al. | 210/151 |
| 7,176,017 B2 | 2/2007 | Parent et al. | 435/297.1 |
| 7,176,024 B2 | 2/2007 | Branson et al. | 435/420 |
| 7,183,074 B2 | 2/2007 | Chen et al. | 435/41 |
| 7,191,597 B2 | 3/2007 | Goldman | 60/641.8 |
| 7,198,940 B2 | 4/2007 | Vellinger et al. | 435/286.5 |
| 7,252,979 B2 | 8/2007 | Behrens et al. | 435/134 |
| 7,270,996 B2 | 9/2007 | Cannon et al. | 435/293.1 |
| 7,279,314 B2 | 10/2007 | Matsuo | 435/119 |
| 7,320,889 B2 | 1/2008 | Kahlert et al. | 435/295.3 |
| 7,331,178 B2 | 2/2008 | Goldman | 60/641.11 |
| 7,333,195 B2 | 2/2008 | Krei.beta. et al. | 356/317 |
| 7,392,615 B2 | 7/2008 | Lee | 47/58.1 S |
| 7,425,441 B2 | 9/2008 | Broneske et al. | 435/292.1 |
| 7,435,581 B2 | 10/2008 | West | 435/289.1 |
| 7,449,313 B2 | 11/2008 | Rush | 435/165 |
| 7,479,226 B2 | 1/2009 | Dunlop et al. | 210/602 |
| 7,507,554 B2 | 3/2009 | Bush et al. | 435/42 |

(56) References Cited

U.S. PATENT DOCUMENTS

| | | |
|---|---|---|
| 7,507,579 B2 | 3/2009 | Boccazzi et al. ............ 435/297.5 |
| 7,510,864 B2 | 3/2009 | Krichevsky et al. ....... 435/286.5 |
| 7,514,247 B2 | 4/2009 | Rush ............................ 435/165 |
| 7,531,350 B2 | 5/2009 | Shiau ......................... 435/292.1 |
| 7,536,827 B2 | 5/2009 | Busch et al. .................. 47/62 R |
| 7,566,551 B2 | 7/2009 | Zhang ............................ 435/67 |
| 7,572,546 B2 | 8/2009 | Karamanev ................... 429/101 |
| 7,585,898 B2 | 9/2009 | Thothathri ..................... 516/80 |
| 7,618,813 B2 | 11/2009 | Lee et al. .................... 435/292.1 |
| 7,632,414 B2 | 12/2009 | Hsu .............................. 210/764 |
| 7,635,586 B2 | 12/2009 | West ........................... 435/286.1 |
| 7,658,851 B2 | 2/2010 | Nelson et al. ................ 210/615 |
| 7,662,615 B2 | 2/2010 | Chang et al. .............. 435/289.1 |
| 7,662,616 B2 | 2/2010 | Hazlebeck et al. ........ 435/289.1 |
| 7,662,617 B2 | 2/2010 | Rush .......................... 435/289.1 |
| 7,682,821 B2 | 3/2010 | Woods et al. .............. 435/292.1 |
| 7,687,161 B2 | 3/2010 | Karamanev ...................... 429/2 |
| 7,687,261 B2 | 3/2010 | Hazlebeck et al. ........ 435/289.1 |
| 7,736,508 B2 | 6/2010 | Limcaco ....................... 210/602 |
| 7,750,494 B1 | 7/2010 | Behrens et al. ................. 290/55 |
| 7,770,322 B2 | 8/2010 | Huntley et al. .................. 47/1.4 |
| 7,771,515 B2 | 8/2010 | Champagne et al. ........... 95/242 |
| 7,905,049 B2 | 3/2011 | Erd .................................. 47/1.4 |
| 7,977,085 B2 | 7/2011 | Rispoli et al. ............... 435/257.1 |
| 8,262,776 B2 | 9/2012 | Hazlebeck et al. |
| 2002/0034817 A1 | 3/2002 | Henry et al. ................ 435/257.1 |
| 2002/0072109 A1 | 6/2002 | Bayless et al. ............... 435/266 |
| 2002/0130076 A1 | 9/2002 | Merritt ......................... 210/615 |
| 2002/0138454 A1 | 9/2002 | Gruenberg et al. .............. 706/7 |
| 2003/0044114 A1 | 3/2003 | Pelka ............................. 385/31 |
| 2003/0153059 A1 | 8/2003 | Pilkington et al. ........... 435/161 |
| 2003/0155090 A1 | 8/2003 | Holmberg et al. ........... 162/161 |
| 2003/0162273 A1 | 8/2003 | Melis et al. .................. 435/168 |
| 2003/0228684 A1 | 12/2003 | Burbidge et al. ........... 435/292.1 |
| 2004/0077036 A1 | 4/2004 | Thomas et al. ................. 435/67 |
| 2004/0191755 A1 | 9/2004 | Kemper et al. ................... 435/3 |
| 2004/0266622 A1 | 12/2004 | Park ........................... 504/116.1 |
| 2005/0036932 A1 | 2/2005 | Takahashi et al. ........... 423/432 |
| 2005/0037480 A1 | 2/2005 | Chiueh ....................... 435/252.1 |
| 2005/0044911 A1 | 3/2005 | Shimose ........................... 71/8 |
| 2005/0064577 A1 | 3/2005 | Berzin ......................... 435/266 |
| 2005/0186671 A1 | 8/2005 | Cannon et al. ............. 435/297.2 |
| 2005/0239182 A1 | 10/2005 | Berzin ......................... 435/166 |
| 2005/0244957 A1 | 11/2005 | Stock ......................... 435/289.1 |
| 2005/0260553 A1 | 11/2005 | Berzin ............................ 435/3 |
| 2006/0019375 A1 | 1/2006 | Seidl et al. ................. 435/289.1 |
| 2006/0134598 A1 | 6/2006 | Kenney ............................ 435/3 |
| 2006/0151402 A1 | 7/2006 | Hsu .............................. 210/764 |
| 2006/0216818 A1 | 9/2006 | Amano ...................... 435/287.5 |
| 2006/0223155 A1 | 10/2006 | Streeter ...................... 435/173.8 |
| 2006/0258000 A1 | 11/2006 | Allen et al. ................... 435/325 |
| 2006/0275858 A1 | 12/2006 | Saucedo et al. ................ 435/25 |
| 2006/0281163 A1 | 12/2006 | Diz et al. ..................... 435/168 |
| 2007/0010002 A1 | 1/2007 | Melkonian et al. ........ 435/252.1 |
| 2007/0015263 A1 | 1/2007 | Wumpelman ............... 435/134 |
| 2007/0042487 A1 | 2/2007 | Cheshire ..................... 435/283.1 |
| 2007/0048848 A1 | 3/2007 | Sears ........................... 435/134 |
| 2007/0048859 A1 | 3/2007 | Sears ......................... 435/289.1 |
| 2007/0054351 A1 | 3/2007 | Zhang ............................ 435/67 |
| 2007/0092962 A1 | 4/2007 | Sheppard ...................... 435/266 |
| 2007/0113474 A1 | 5/2007 | Everett et al. ................. 47/65.8 |
| 2007/0114186 A1 | 5/2007 | Dart et al. .................... 210/749 |
| 2007/0157614 A1 | 7/2007 | Goldman ................... 60/641.15 |
| 2007/0161095 A1 | 7/2007 | Gurin ........................... 465/134 |
| 2007/0202582 A1 | 8/2007 | Bush et al. ................... 435/161 |
| 2007/0264708 A1 | 11/2007 | Bayless et al. ............. 435/292.1 |
| 2007/0269874 A1 | 11/2007 | Kosourov et al. ........... 435/168 |
| 2007/0275856 A1 | 11/2007 | Thothathri .................... 504/151 |
| 2008/0009055 A1 | 1/2008 | Lewnard ...................... 435/262 |
| 2008/0028675 A1 | 2/2008 | Clifford et al. .................. 44/605 |
| 2008/0044887 A1 | 2/2008 | Maliezos et al. ........... 435/257.1 |
| 2008/0050800 A1 | 2/2008 | McKeeman et al. ...... 435/262.5 |
| 2008/0052987 A1 | 3/2008 | Busch et al. ................... 47/62 R |
| 2008/0085536 A1 | 4/2008 | Nobles et al. ............... 435/69.1 |
| 2008/0086938 A1 | 4/2008 | Hazlebeck et al. ............ 47/1.4 |
| 2008/0096267 A1 | 4/2008 | Howard et al. ............ 435/257.1 |
| 2008/0113413 A1 | 5/2008 | Nobles et al. .................... 435/72 |
| 2008/0115500 A1 | 5/2008 | MacAdam et al. |
| 2008/0118964 A1 | 5/2008 | Huntley et al. ................ 435/166 |
| 2008/0131958 A1 | 6/2008 | Remmereit et al. ........ 435/290.1 |
| 2008/0138875 A1 | 6/2008 | Atehortua et al. ............ 435/171 |
| 2008/0155890 A1 | 7/2008 | Oyler ................................ 47/1.4 |
| 2008/0160591 A1 | 7/2008 | Willson et al. ............... 435/132 |
| 2008/0160593 A1 | 7/2008 | Oyler ............................ 435/166 |
| 2008/0160597 A1 | 7/2008 | van der Heiden et al. ................. 435/252.8 |
| 2008/0166779 A1 | 7/2008 | Thomas et al. ............... 435/134 |
| 2008/0176303 A1 | 7/2008 | Massie .......................... 435/163 |
| 2008/0176304 A1 | 7/2008 | Lee ............................... 435/165 |
| 2008/0178739 A1 | 7/2008 | Lewnard ................. 95/186 |
| 2008/0182325 A1 | 7/2008 | Hobbs et al. ............... 435/292.1 |
| 2008/0210632 A1 | 9/2008 | Kruse ........................... 210/612 |
| 2008/0213049 A1 | 9/2008 | Higgins et al. ............. 405/302.6 |
| 2008/0213868 A1 | 9/2008 | Fournier .................... 435/257.1 |
| 2008/0220486 A1 | 9/2008 | Weiss ............................ 435/134 |
| 2008/0220489 A1 | 9/2008 | Offerman ...................... 435/157 |
| 2008/0220515 A1 | 9/2008 | McCall ........................ 435/292.1 |
| 2008/0241902 A1 | 10/2008 | Berry et al. ................... 435/161 |
| 2008/0254056 A1 | 10/2008 | Zhang ...................... 424/195.17 |
| 2008/0268302 A1 | 10/2008 | McCall ......................... 429/513 |
| 2008/0274494 A1 | 11/2008 | Kertz ............................. 435/29 |
| 2008/0293132 A1 | 11/2008 | Goldman et al. ........... 435/292.1 |
| 2008/0299539 A1 | 12/2008 | Lee et al. ......................... 435/3 |
| 2008/0299643 A1 | 12/2008 | Howard et al. ............ 435/252.1 |
| 2008/0303348 A1 | 12/2008 | Witters .......................... 307/72 |
| 2008/0305539 A1 | 12/2008 | Hickey et al. ............... 435/289.1 |
| 2008/0311646 A1 | 12/2008 | Cong et al. ................. 435/257.1 |
| 2008/0318304 A1 | 12/2008 | Burton et al. .............. 435/257.1 |
| 2009/0004715 A1 | 1/2009 | Trimbur et al. .............. 435/166 |
| 2009/0011492 A1 | 1/2009 | Berzin ........................ 435/257.1 |
| 2009/0017514 A1 | 1/2009 | Datta et al. ................... 435/170 |
| 2009/0023199 A1 | 1/2009 | Gal ............................. 435/286.5 |
| 2009/0029445 A1 | 1/2009 | Eckelberry et al. ........ 435/257.1 |
| 2009/0035835 A1 | 2/2009 | Slavin ......................... 435/173.8 |
| 2009/0047722 A1 | 2/2009 | Wilkerson et al. ......... 435/173.7 |
| 2009/0047730 A1 | 2/2009 | Higgins et al. ............ 435/257.1 |
| 2009/0068715 A1 | 3/2009 | Ogaki et al. .................. 435/163 |
| 2009/0068727 A1 | 3/2009 | Karr ........................... 435/292.1 |
| 2009/0075353 A1 | 3/2009 | Ogaki et al. .................. 435/161 |
| 2009/0077863 A1 | 3/2009 | Oyler .............................. 44/307 |
| 2009/0077864 A1 | 3/2009 | Marker et al. ................... 44/307 |
| 2009/0081743 A1 | 3/2009 | Hazelbeck et al. ........... 435/157 |
| 2009/0081744 A1 | 3/2009 | Kastanek ...................... 435/157 |
| 2009/0081748 A1 | 3/2009 | Oyler ............................ 435/165 |
| 2009/0081770 A1 | 3/2009 | Srienc et al. ............... 435/289.1 |
| 2009/0104594 A1 | 4/2009 | Webb ................................ 435/3 |
| 2009/0113790 A1 | 5/2009 | Erd .................................. 47/1.4 |
| 2009/0117647 A1 | 5/2009 | Buddhi Srinivasa et al. ................ 435/289.1 |
| 2009/0126265 A1 | 5/2009 | Rasmussen et al. ............ 47/1.4 |
| 2009/0130706 A1 | 5/2009 | Berzin et al. ................... 435/41 |
| 2009/0130747 A1 | 5/2009 | Wen-Teng et al. ......... 435/292.1 |
| 2009/0134091 A1 | 5/2009 | Stephens et al. ............. 210/602 |
| 2009/0137013 A1 | 5/2009 | Schmid et al. ................ 435/134 |
| 2009/0137025 A1 | 5/2009 | Stephens et al. .......... 435/286.2 |
| 2009/0148927 A1 | 6/2009 | Schroeder et al. ......... 435/257.1 |
| 2009/0148931 A1 | 6/2009 | Wilkerson et al. ......... 435/286.1 |
| 2009/0151240 A1 | 6/2009 | Kayama et al. ................ 47/1.4 |
| 2009/0151241 A1 | 6/2009 | Dressler et al. ................. 47/1.4 |
| 2009/0155864 A1 | 6/2009 | Bauer et al. .................. 435/134 |
| 2009/0170184 A1 | 7/2009 | Shepherd et al. ............ 435/244 |
| 2009/0181438 A1 | 7/2009 | Sayre ............................ 435/134 |
| 2009/0197322 A1 | 8/2009 | Goldman .................... 435/257.1 |
| 2009/0203067 A1* | 8/2009 | Eckerle .................. C12M 21/02 435/41 |
| 2009/0203115 A1 | 8/2009 | Busch et al. ................ 435/252.1 |
| 2009/0203116 A1 | 8/2009 | Bazaire ....................... 435/252.1 |
| 2009/0205638 A1 | 8/2009 | Corcoran ...................... 126/683 |
| 2009/0215155 A1 | 8/2009 | Cloud et al. ................ 435/257.1 |
| 2009/0221057 A1 | 9/2009 | Kennedy ..................... 435/286.5 |
| 2009/0227003 A1 | 9/2009 | Blotsky et al. ............. 435/257.1 |
| 2009/0227456 A1 | 9/2009 | Hsu .............................. 504/151 |
| 2009/0230040 A1 | 9/2009 | Limcaco ....................... 210/151 |
| 2009/0232861 A1 | 9/2009 | Wright et al. ................ 424/405 |

(56) References Cited

U.S. PATENT DOCUMENTS

| | | |
|---|---|---|
| 2009/0233334 A1 | 9/2009 | Hildinger et al. ............ 435/71.1 |
| 2009/0249685 A1 | 10/2009 | Flowers et al. ................. 44/605 |
| 2009/0250401 A1 | 10/2009 | Kotelko et al. ............... 210/695 |
| 2009/0263889 A1 | 10/2009 | Wumpelmann ............. 435/257.1 |
| 2009/0269839 A1 | 10/2009 | Oyler ......................... 435/289.1 |
| 2009/0275120 A1 | 11/2009 | Koch et al. ................. 435/292.1 |
| 2009/0286295 A1 | 11/2009 | Medoff et al. ................ 435/162 |
| 2009/0286296 A1 | 11/2009 | Hickey et al. ................ 435/170 |
| 2009/0291485 A1 | 11/2009 | Shigematsu et al. ...... 435/257.1 |
| 2009/0294354 A1 | 12/2009 | Theodore et al. ............ 210/602 |
| 2009/0298159 A1 | 12/2009 | Wu et al. ................... 435/257.3 |
| 2009/0305388 A1 | 12/2009 | Dressler et al. ........... 435/257.1 |
| 2009/0309515 A1 | 12/2009 | Crabb et al. ................. 315/294 |
| 2009/0317901 A1 | 12/2009 | Vance ........................ 435/292.1 |
| 2009/0321349 A1 | 12/2009 | Offerman et al. ............ 210/603 |
| 2009/0324799 A1 | 12/2009 | Hartman et al. ............. 426/635 |
| 2009/0325253 A1 | 12/2009 | Ascon et al. ................. 435/163 |
| 2010/0003717 A1 | 1/2010 | Oyler ............................. 435/42 |
| 2010/0003741 A1 | 1/2010 | Fromson ...................... 435/262.5 |
| 2010/0005711 A1 | 1/2010 | McNeff .......................... 47/1.4 |
| 2010/0011778 A1 | 1/2010 | Knight et al. .................. 60/772 |
| 2010/0018214 A1 | 1/2010 | Halachmi Katchanov ..... 60/772 |
| 2010/0021968 A1 | 1/2010 | Hu et al. |
| 2010/0028976 A1 | 2/2010 | Hu et al. ..................... 435/257.1 |
| 2010/0028977 A1 | 2/2010 | Ng et al. .................... 435/257.1 |
| 2010/0034050 A1 | 2/2010 | Erb et al. ...................... 366/342 |
| 2010/0035321 A1 | 2/2010 | Wilkerson et al. ......... 435/173.1 |
| 2010/0035343 A1 | 2/2010 | Cheng et al. ................. 435/394 |
| 2010/0043446 A1 | 2/2010 | Shirvanian et al. ............ 60/781 |
| 2010/0050502 A1 | 3/2010 | Wu et al. ........................ 44/308 |
| 2010/0055765 A1 | 3/2010 | Frank ........................ 435/257.1 |
| 2010/0062483 A1 | 3/2010 | Beliaev et al. ................. 435/41 |
| 2010/0068693 A1 | 3/2010 | Tsang et al. ..................... 435/3 |
| 2010/0068779 A1 | 3/2010 | Wells et al. ................... 435/167 |
| 2010/0068791 A1 | 3/2010 | Merimon et al. .......... 435/257.1 |
| 2010/0068801 A1 | 3/2010 | Woods et al. ............... 435/292.1 |
| 2010/0071370 A1 | 3/2010 | O'Kane .......................... 60/685 |
| 2010/0077654 A1 | 4/2010 | Wu et al. ........................ 44/385 |
| 2010/0081122 A1 | 4/2010 | Shibuya et al. .................. 435/3 |
| 2010/0081177 A1 | 4/2010 | Schatz et al. ................ 435/134 |
| 2010/0081835 A1 | 4/2010 | Wu et al. .......................... 554/8 |
| 2010/0093046 A1 | 4/2010 | Remmereit et al. ......... 435/134 |
| 2010/0093078 A1 | 4/2010 | Wang et al. .................. 435/325 |
| 2010/0099151 A1 | 4/2010 | Stroiazzo-Mougin et al. ............ 435/101 |
| 2010/0099157 A1 | 4/2010 | Salvetzki ...................... 435/167 |
| 2010/0099170 A1 | 4/2010 | Aswani ...................... 435/257.1 |
| 2010/0101621 A1 | 4/2010 | Xu ................................ 136/206 |
| 2010/0105125 A1 | 4/2010 | Haley ......................... 435/257.1 |
| 2010/0105126 A1 | 4/2010 | Wright et al. .............. 435/257.1 |
| 2010/0105127 A1 | 4/2010 | Ginsburg ...................... 435/262 |
| 2010/0105129 A1 | 4/2010 | Sanchez-Pina et al. ... 435/286.5 |
| 2010/0107487 A1 | 5/2010 | Rolland ........................... 47/1.4 |
| 2010/0112649 A1 | 5/2010 | Willson et al. .............. 435/134 |
| 2010/0112700 A1 | 5/2010 | Shaaltiel et al. ............. 435/410 |
| 2010/0120134 A1 | 5/2010 | Gal ............................ 435/289.1 |
| 2010/0139265 A1 | 6/2010 | Stroiazzo Mougin .......... 60/531 |
| 2010/0151558 A1 | 6/2010 | Alianell et al. ............. 435/257.3 |
| 2010/0159539 A1 | 6/2010 | Ascon et al. ................. 435/134 |
| 2010/0159567 A1 | 6/2010 | Kuehnle et al. ............ 435/257.3 |
| 2010/0159578 A1 | 6/2010 | Lacaze et al. ............... 435/292.1 |
| 2010/0159579 A1 | 6/2010 | Schuring et al. ........... 435/292.1 |
| 2010/0162620 A1 | 7/2010 | McCaffrey et al. ............ 47/1.4 |
| 2010/0167339 A1 | 7/2010 | Clayton et al. ................. 435/41 |
| 2010/0167381 A1 | 7/2010 | Woerlee et al. ............ 435/257.1 |
| 2010/0170149 A1 | 7/2010 | Keeler et al. ................... 47/1.4 |
| 2010/0173355 A1 | 7/2010 | Haase et al. ................... 435/41 |
| 2010/0173375 A1 | 7/2010 | Oyler ............................ 435/167 |
| 2010/0184177 A1 | 7/2010 | Mitchell ....................... 435/166 |
| 2010/0184194 A1 | 7/2010 | Nagnath ........................ 435/244 |
| 2010/0189806 A1 | 7/2010 | Harper et al. .................. 424/601 |
| 2010/0190227 A1 | 7/2010 | Dauth et al. .................. 435/168 |
| 2010/0196995 A1 | 8/2010 | Weissman et al. ......... 435/257.1 |
| 2010/0203618 A1 | 8/2010 | Rispoli et al. .............. 435/257.3 |
| 2010/0210001 A1 | 8/2010 | Seyfried et al. ............ 435/257.1 |
| 2010/0210002 A1 | 8/2010 | McCaffrey et al. ........ 435/257.1 |
| 2010/0211812 A1 | 8/2010 | Bullen et al. |
| 2010/0216240 A1 | 8/2010 | Moolman et al. ............. 435/395 |
| 2010/0227368 A1 | 9/2010 | Steiner .......................... 435/161 |
| 2010/0233786 A1 | 9/2010 | O'Connor .................. 435/257.1 |
| 2010/0233787 A1 | 9/2010 | Halachmi Katchanov ................... 435/257.1 |
| 2010/0233796 A1 | 9/2010 | Kurihara et al. ........... 435/289.1 |
| 2010/0267122 A1 | 10/2010 | Chinnasamy et al. ..... 435/257.3 |
| 2010/0273210 A1 | 10/2010 | Reddy ............................ 435/41 |
| 2010/0297739 A1 | 11/2010 | Steiner et al. ............. 435/257.1 |
| 2010/0297749 A1 | 11/2010 | Aravanis et al. ........... 435/289.1 |
| 2011/0014683 A1 | 1/2011 | Vermaas et al. ............ 435/252.1 |
| 2011/0020913 A1 | 1/2011 | Rispoli et al. ............. 435/257.1 |
| 2011/0023565 A1 | 2/2011 | Yanik et al. ...................... 71/11 |
| 2011/0027827 A1 | 2/2011 | Chi et al. ........................ 435/41 |
| 2011/0113681 A1 | 5/2011 | Mostertz et al. ................. 47/1.4 |
| 2011/0124091 A1 | 5/2011 | Lu et al. .................... 435/257.1 |
| 2011/0139409 A1 | 6/2011 | Erd ............................... 165/120 |
| 2011/0159581 A1 | 6/2011 | Zhang et al. ............... 435/292.1 |
| 2011/0195473 A1 | 8/2011 | Wilhelm ........................ 435/168 |
| 2011/0195493 A1 | 8/2011 | Stroiazzo-Mougin ..... 435/292.1 |
| 2011/0236958 A1 | 9/2011 | Wong |
| 2011/0287405 A1 | 11/2011 | Gonzalez et al. |
| 2012/0020228 A1 | 1/2012 | Ding et al. |
| 2012/0203714 A1 | 8/2012 | Gonzalez et al. |
| 2012/0276633 A1 | 11/2012 | Gonzalez et al. |
| 2014/0186931 A1 | 7/2014 | Gonzalez et al. |

FOREIGN PATENT DOCUMENTS

| | | |
|---|---|---|
| CA | 2738418 | 11/2011 |
| CA | 2738459 | 11/2011 |
| CA | 2738461 | 11/2011 |
| CA | 2738516 | 11/2011 |
| CN | 1668185 A | 9/2005 |
| CN | 1668185 A | 9/2005 |
| CN | 1724637 A | 1/2006 |
| CN | 2749890 | 1/2006 |
| CN | 101139113 | 3/2008 |
| CN | 101254364 | 9/2008 |
| CN | 101356261 | 1/2009 |
| CN | 101356261 A | 1/2009 |
| CN | 201381254 | 1/2010 |
| CN | 101643700 A | 2/2010 |
| CN | 101648092 | 2/2010 |
| CN | 101669569 | 3/2010 |
| CN | 101696389 | 4/2010 |
| CN | 101696389 A | 4/2010 |
| CN | 10326396 | 8/2013 |
| EP | 1072301 | 1/2001 |
| EP | 2422870 | 2/2012 |
| GB | 2458529 | 9/2009 |
| JP | 3076586 | 4/1991 |
| JP | 4084883 | 3/1992 |
| JP | 4287678 | 10/1992 |
| TW | 200913876 A | 4/2009 |
| WO | WO 91/18108 | 11/1991 |
| WO | 9623865 A1 | 8/1996 |
| WO | WO 98/00559 | 1/1998 |
| WO | WO 98/28081 | 7/1998 |
| WO | WO 98/28082 | 7/1998 |
| WO | WO 98/28083 | 7/1998 |
| WO | WO 98/28403 | 7/1998 |
| WO | WO 98/28404 | 7/1998 |
| WO | WO 99/01021 | 1/1999 |
| WO | WO 03/038348 | 5/2003 |
| WO | 03094598 | 11/2003 |
| WO | WO 2005/006838 | 1/2005 |
| WO | WO 2006/020177 | 2/2006 |
| WO | 2007/047805 | 4/2007 |
| WO | WO 2007/070452 | 6/2007 |
| WO | WO 2007/134141 | 11/2007 |
| WO | WO2007/134141 | 11/2007 |
| WO | 2008008226 A2 | 1/2008 |
| WO | WO2008/008262 | 1/2008 |
| WO | WO 2008/008262 | 1/2008 |
| WO | WO 2008/028143 | 3/2008 |
| WO | 2008/079896 | 7/2008 |

(56) References Cited

FOREIGN PATENT DOCUMENTS

| | | |
|---|---|---|
| WO | WO 2008/089321 | 7/2008 |
| WO | WO2008/128625 | 10/2008 |
| WO | WO 2008/128625 | 10/2008 |
| WO | WO 2008/156795 | 12/2008 |
| WO | WO 2008/156835 | 12/2008 |
| WO | WO 2009/015054 | 1/2009 |
| WO | WO 2009/018498 | 2/2009 |
| WO | WO 2009/094440 | 7/2009 |
| WO | WO 2009/134358 | 11/2009 |
| WO | WO 2009/142765 | 11/2009 |
| WO | 2010/010554 | 1/2010 |
| WO | WO 2010/002745 | 1/2010 |
| WO | WO 2010/009284 | 1/2010 |
| WO | WO 2010/011320 | 1/2010 |
| WO | WO 2010/021753 | 2/2010 |
| WO | WO 2010/034023 | 3/2010 |
| WO | 2010/094015 | 8/2010 |
| WO | 2010/108049 | 9/2010 |
| WO | 2010/123943 | 10/2010 |
| WO | 2011/050578 | 5/2011 |
| WO | 2011/143749 | 11/2011 |

OTHER PUBLICATIONS

Carvalho, A.P., et al., "Microalgal Reactors: A Review of Enclosed System Designs and Performances". Biotechnol. Prog., 2006, vol. 22, No. 6, pp. 1490-1506. ISSN: 87567938.
Eriksen "The technology of microalgal culturing". Biotechnol Lett., 2008, vol. 30, pp. 1525-1536. ISSN: 01415492.
International Search Report and Written Opinion; Application No. PCT/CA2011/001367; dated Apr. 19, 2012; 22 pages.
Ishida, M., et al., "CO2 Recovery in a Power Plant with Chemical Looping Combustion". Energy Convers. Mgmt., 1997, vol. 38, Suppl., pp. S187-S192. ISSN: 01968904.
Negoro, et al., "Carbon Dioxide Fixation by Microalgae Photosynthesis Using Actual Flue Gas Discharged from a Boiler". Appl. Biochem. Biotechnol., 1993, vol. 39/40, pp. 643-653. ISSN: 02732289.
Pulz "Photobioreactors: production systems for phototrophic microorganisms". Appl. Microbial. Biotechnol, 2001, vol. 57, pp. 287-293. ISSN: 01757598.
Wang, et al., "CO2 bio-mitigation using microalgae". Appl. Microbiol. Biotechnol., 2008, vol. 79, pp. 709-718. ISSN: 01757598.
EPO, Office Action for EP Application No. 11 858 246.9 dated Nov. 18, 2016.
EPO, Office Action for EP Application No. 11 782 806.1 dated Jan. 19, 2017.
Chinese Patent Office First Office Action issued in Chinese Application No. 201510307487.2, dated Jul. 25, 2017.
Chinese Patent Office Second Office Action issued in Chinese Application No. 20150307487.2, dated Jun. 15, 2018.
Examination Report; Australian application No. 2018204391 dated Jun. 22, 2019.
Extended European Search report; EP Application No. 181883042 dated Nov. 27, 2018.
Final Rejection; U.S. Appl. No. 14/971,854 dated Dec. 3, 2019.
Final Rejection; U.S. Appl. No. 14/971,854 dated Feb. 28, 2018.
First Exam Report; GC Application No. 2011-18441 dated Apr. 6, 2017.
First Exam Report; GCC Application No. 2011/37439 dated Feb. 22, 2020.
Mata, TM, et al, Renewable and Sustainable Energy Reviews, vol. 14I pp. 217-232 2010.
Muller-Fuega, A et al., J Blotechnol, vol. 103, pp. 153-163 2003.
Pemi, S, et al, Food Microbiol, vol. 22, pp. 491-495 2005.
Office Action; U.S. Appl. No. 14/971,854 dated May 10, 2017.
Restriction Requirement; U.S. Appl. No. 14/971,854 dated Dec. 9, 2016.
Second Exam Report; GC Application No. 2011-18441 dated Dec. 17, 2018.
Office Action; U.S. Appl. No. 14/971,854 dated Mar. 4, 2019.
Office Action; TW Application No. 106126815 dated Mar. 8, 2019.
Notification of the First Office Action; CN Application No. 201180067005 dated Sep. 24, 2014.
Office Action; CA Application No. 2738516 dated Mar. 8, 2018.
Office Action; CA Application No. 2799988 dated Mar. 5, 2018.
Office Action; CA Application No. 2826322 dated Oct. 29, 2018.
Office Action; CA Application No. 2826322 dated Sep. 27, 2017.
Office Action; CA Application No. 2826322 dated Jan. 9, 2020.
Office Action; Indian Application n o. 4045/KOLNP/2012 dated Jul. 20, 2018.
Office Action; Indian Application No. 2689/KOLP/2013 dated Jun. 26, 2019.
Coutteau, P. "Microalgae"; pp. 7-48: FAO Fisheries Technical Papers. No. 361, Lavens, P, et al. eds, Rome, FAO 1996.
Dunham, MJ, Meth Enzymol, vol. 470, pp. 488-507 2010.
Maier, RM, Bacterial Growth, pp. 37-54 in: Environmental Microbiology; Academic Press, San Diego, CA 2000.
Najafpour, GD, chapter 5—Growth Kinetics in: Biochem Eng Biotechnol, pp. 81-141 2007.
Mohamad Hekarl Uzier et al. "Biochemical Enginnering—A consise introduction"; XP055521831; Dec. 2007.
Office Action; U.S. Appl. No. 14/971,854 dated Jun. 23, 2020.
Aquarobic Canada Frequently Asked Questions, pp. 1-3; retrieved from the internet Jun. 16, 2020: http://www.aquarobic-canada.com/faq.html (Year: 2020) 2020.
Alabi et al., Seed Science, 2009, pp. 1-75 2009.
Jaworski et al., British Phycological Journal, vol. 16, No. 4, pp. 395-410 2007.
Larsson et al., Master of Science Thesis Jan. 2011.
Lundquist et al., Energy Biosciences Institute, University of California, pp. 1-153 Oct. 2010.
USPTO, Office Action for U.S. Appl. No. 13/327,541 dated Sep. 19, 2012.
USPTO, Office Action for U.S. Appl. No. 13/327,541 dated Jun. 27, 2013.
USPTO, Office Action for U.S. Appl. No. 13/327,541 dated Sep. 19, 2014.
USPTO, Office Action for U.S. Appl. No. 13/327,541 dated Jul. 14, 2015.
USPTO, Office Action for U.S. Appl. No. 13/327,541 dated Feb. 11, 2016.
USPTO, Office Action for U.S. Appl. No. 13/699,195 dated Oct. 3, 2014.
USPTO, Office Action for U.S. Appl. No. 13/699,195 dated Jun. 16, 2015.
EPO, Office Action for EP Application No. 11858246.9 dated Jan. 15, 2016.
EPO, Office Action for EP Application No. 11782806.1 dated Nov. 27, 2015.
State Intellectial Property Office of P.R.C., Office Action for CN Application No. 201180035594.4 dated Jan. 16, 2015.
IP Australia, Patent Examination Report No. 1 for AU Application No. 2011256085 dated Mar. 27, 2015.
International Search Report and Written Opinion; dated May 10, 2012; World Intellectual Property Organization (WIPO) (International Bureau of); PCT/CA2011/000097; 10 pages.
International Search Report and Written Opinion; dated May 23, 2012; World Intellectual Property Organization (WIPO) (International Bureau of); PCT/CA2012/000093; 17 pages.
International Search Report and Written Opinion; dated Jul. 31, 2012; World Intellectual Property Organization (WIPO) (International Bureau of); PCT/CA2011/000403; 12 pages.
Stewart et al; A Study of Methods of Carbon Dioxide Capture and Sequestration—The Sustainability of a Photosynthetic Bioreacter Approach; Energy Conversion and Management; 2005; 46:403-420.
European Search Report issued in EP 11782806 dated Aug. 1, 2014 (7 pages).
Chinese Office Action (with English Translation) issued in CN 2014091901006550, dated Sep. 24, 2014 (25 pages).
Response to Office Action issued in U.S. Appl. No. 13/022,508 dated Nov. 6, 2014, Examiner William H. Beisner, filed on Apr. 6, 2015 (13 pages).

(56) References Cited

OTHER PUBLICATIONS

Chinese Office Action (with English Translation) issued in CN 201280031706.3, dated Jan. 9, 2015 (12 pages).
European Search Report issued in EP 12776555 dated Dec. 22, 2014 (6 pages).
Herzog et al., "Advanced Post-Combustion $CO_2$ Capture" Clean Air Task Force, Apr. 2009, 39 pages.
Office Action issued in U.S. Appl. No. 13/095,490 dated Oct. 8, 2014, Examiner Cynthia Collins (88 pages).
Office Action issued in U.S. Appl. No. 14/089,278 dated Jan. 12, 2015, Examiner Trent R. Clarke (16 pages).
Final Office Action issued in U.S. Appl. No. 13/022,508 dated Nov. 6, 2014, Examiner William H. Beisner (10 pages).
Office Action issued in U.S. Appl. No. 13/021,489 dated Dec. 4, 2014, Examiner Jan P. Mincarelli (75 pages).
Response to Office Action issued in U.S. Appl. No. 13/095,490 dated Oct. 8, 2014, Examiner Cynthia E. Collins, filed on Mar. 9, 2015, 10 pages.
European Search Report issued in EP 11858246.9, dated Sep. 17, 2014 (6 pages).
Kunjapur et al., Photobioreactor Design for Commercial Biofuel Production from Microalgae, Ind. Eng. Chem. Res., 49:3516-3526, Mar. 2010 (11 pages).
Chinese Office Action (with English translation) issued in CN 201180035594, dated Jan. 16, 2015 (English Translation) (22 pages).
Re-Examination Notice and English Translation thereof; CN application No. 201510307487.2; dated Dec. 1, 2020.
Taiwanese Office Action (with English Translation) issued in TW 10117390, dated Jun. 2, 2015 (19 pages).
Berenguel et al. "Model predictive control of pH in tubular photobioreactors" *Journal of Process Control*, 2004 14, pp. 377 387.
Carvalho, A.P., et al., "Microalgal Reactors: A Review of Enclosed System Designs and Performances", *Biotechnol. Prog.*, 2006. vol. 22, No. 6, pp. 1490-1506.
Cote, R. and Wright, R. "Resource Conservation and Industrial Symbiosis: Strategies for enhancing the environmental sustainability of the Keltic Petrochemical Cluster" Prepared by Eco-Efficiency Centre Dalhousie University, on Mar. 29, 2006 (Mar. 29, 2006), Retrieved on Apr. 19, 2012 from http://eco-efficiency.management.dal.ca/Files/Keltic Petrochemical Cluster.pdf.
Degen, et al. "A novel airlift photobioreactor with baffles for improved light utilization through the flashing light effect", *Journal of Biotechnology*, 2001, 92, pp. 89-94.
Fernandez et al. "Airlift-driven external-loop tubular photobioreactors for outdoor production of microalgae assessment of design and performance", *Chemical Engineering Science* [Online], 2001, 56, 2721-2732.
Greenwell, et al., "Placing microalgae on the biofuels priority list: a review of the technological challenges" *J. R. Soc. Interface* Jul. 2010, 703-726 first published online Dec. 23, 2009 doi: 10.1098/rsif.2009.0322.
Hamilton, T. "CO2-eating algae turns cement maker green" *The Star*, Published on Mar. 18, 2010, Retrieved on Apr. 1, 2013 from http://www.thestar.com/business/article/781426--co2-eating-algae-turns-cement-maker-green.
Hurst, T., "Canadian Cement Plant Becomes First to Capture CO2 in Algae-A Canadian company called Pond Biofuels is capturing CO2 emissions from a cement plant in algae-algae the company ultimately plans on using to make biofuel." *Earth and Industry*, Mar. 19, 2010, Retrieved on Apr. 1, 2013 from http://earthandindustry.com/2010/03/canadian-cement-plant-becomes-first-to-capture-co2-in-algae.
Ishida, M., et al., "CO2 Recovery in a Power Plant with Chemical Looping Combustion". *Energy Convers. Mgmt.*, 1997, vol. 38, Suppl., pp. S187-S192.
Janssen, M. et al., "Enclosed outdoor photobireactors: Light regime, photosynthetic efficiency, scale-up, and future prospects", *Biotechnology and Bioengineering*, vol. 81, Iss. 2, 2003, pp. 193-210.
Lee et al. "High density algal photobioreactors using light emitting diodes", *Biotech. BioEng.* [Online] 1994, 44. pp. 1161-1167.

Maeda, et al., "CO2 fixation from the flue gas on coal-fired thermal power plant by microalgae", *Energy Convers. Mgmt* vol. 36, No. 6-9, pp. 717-720, 1995.
Masojidek et al. "A closed solar photobioreactor for cultivation of microalgae under supra-high irradiance basic design and performance", *Journal of Applied Phycology* [Online] 2003, 15, 239-248.
Matthijs et al. "Application of light emitting diodes in bioreactors: flashing light effects and energy economy in algal culture", *Biotechnol. Bioeng.* 1996, 50, pp. 98-107.
Meridian Planning Consultants Inc., "Bruce Energy Center Discussion Paper, Municipality of Kincardine", Prepared by Meridian Planning Consultants Inc. Jun. 2005 (Jun. 2005), Retrieved on Apr. 1, 2013 from http://www.kincardine.net/public docs/documents/Bruce%20Energy%20Center%20Discussion%20Paper1.pdf.
Negoro, et al., "Carbon Dioxide Fixation by Microalgae Photosynthesis Using Actual Flue Gas Discharged from a Boiler", *Appl. Biochem. Biotechnol.*, 1993, vol. 39/40, pp. 643-653.
Eriksen, "The technology of microalgal culturing", *Biotechnol Lett.*, 2008, vol. 30, pp. 1525-1536.
Pulz, O., "Photobioreactors: production systems for phototrophic microorganisms", *Appl. Microbiol. Biotechnol*, 2001, vol. 57, pp. 287-293.
Putt. "Algae as a Biodiesel Feedstock: A Feasibility Assessment" (Center for Microfibrous Materials Manufacturing, Department of Chemical Engineering, Auburn University, Alabama), 2007.
Stewart, C., et al., "A study of methods of carbon dioxide capture and sequestration—the sustainability of a photosynthetic bioreactor approach", *Energy Conversion and Management*, 2005, vol. 46, pp. 403-420.
Suh, et al., "Photobioreactor Engineering: Design and Performance". *Biotechnol. Bioprocess Eng.*, 2003, vol. 8, No. 6, pp. 313-321.
Wang, et al., "CO2 bio-mitigation using mieroalgae". *Appl. Microbiol. Biotechnol.*, 2008, vol. 79, pp. 709-718.
Yang, et al., "Progress in carbon dioxide separation and capture: A review". *J.Env. Sci.*, 2008, vol. 20, pp. 14-27.
Zebib, "Microalgae Grown in Photobiorecators for Mass Production of Biofuel". Rutger University, Department of Bioenvironmental Engineering, Sep. 2008. Retrieved from http://www.water.rutgers.edu/Educational_Programs/Senior%20Design2008/Algae%20to%20E nergy%20Report.pdf.
Corrected International Search Report and Written Opinion issued in PCT Application PCT/CA2011/000574, dated Nov. 1, 2011.
Shi et al., "Effects of the pH/pCO$_2$ control method on medium chemistry and phytoplankton growth," Biogeosciences, 6:1199-1207 (2009).
Sun et al., "An Experiment on Enclosed and Constant Culture of Marine Microalgae," Fisheries Science, 22(3):22-24 (2003) (Translation).
Cote and Wright, "Resource Conservation and Industrial Symbiosis: Strategies for enhancing the environmental sustainability of the Keltic Petrochemical Cluster" Prepared by Eco-Efficiency Centre Dalhousie University, on Mar. 29, 2006 (Mar. 29, 2006), Retrieved on Apr. 19, 2012 (Apr. 19, 2012), Retrieved from the internet: <URL: http://eco-efficiency.management.dal.ca/Files/KelticPetrochemical Cluster.pdf.
Greenwell, et al., "Placing microalgae on the biofuels priority list: a review of the technological challenges" J. R. Soc. Interface 2010 7, 703-726 first published online Dec. 23, 2009 doi: 10.1098/rsif.2009.0322.
Hamilton, "CO2-eating algae turns cement maker green" The Star, Published on Mar. 18, 2010, Retrieved on Apr. 19, 2012, Retrieved from the internet: <URL: http://www.thestar.com/business/article/781426--co2-eating-algae-turns-cement-maker-green.
Hurst, "Canadian Cement Plant Becomes First to Capture CO2 in Algae-A Canadian company called Pond Biofuels is capturing CO2 emissions from a cement plant in algae-algae the company ultimately plans on using to make biofuel." Earth and Industry, Mar. 19, 2010, Retrieved on Apr. 19, 2012, Retrieved from the internet: <URL: http://earthandindustry.com/2010/03/canadian-cement-plant-becomes-first-to-capture-co2-in-algae.
International Search Report and Written Opinion; Application No. PCT/CA2011/000574; dated Sep. 22, 2011; 21 pages.

(56) References Cited

OTHER PUBLICATIONS

Ishida et al., "$CO_2$ Recovery in a Power Plant with Chemical Looping Combustion". Energy Convers. Mgmt., 1997, vol. 38, Suppl., pp. S187-S192. ISSN: 01968904.
Janssen et al., Enclosed outdoor photobireactors: Light regime, photosynthetic efficiency, scale-up, and future prospects. Biotechnology and Bioengineering, vol. 81, Iss. 2, 2003, pp. 193-210.
Matthijs et al. "Application of light emitting diodes in bioreactors: flashing light effects and energy economy in algal culture." *Biotechnol. Bioeng.* [Online] 2000, 50, pp. 98-107.
Meridian Planning Consultants Inc., "Bruce Energy Center Discussion Paper, Municipality of Kincardine" Prepared by Meridian Planning Consultants Inc. Jun. 2005 (Jun. 2005), Retrieved on Apr. 19, 2012 (Apr. 19, 2012), Retrieved from the internet: <URL: http://www.kincardine.net/publicdocs/documents/Bruce%20Energy%20C enter%20Discussion%20Paper1.pdf.
Niels T. Eriksen, "The technology of microalgal culturing". Biotechnol Lett., 2008, vol. 30, pp. 1525-1536. ISSN: 01415492.
Pulz, "Photobioreactors: production systems for phototrophic microorganisms". Appl. Microbiol. Biotechnol, 2001, vol. 57, pp. 287-293. ISSN: 01757598.
Putt, "Algae as a Biodiesel Feedstock: A Feasibility Assessment" (Center for Microfibrous Materials Manufacturing, Department of Chemical Engineering, Auburn University, Alabama).
Suh et al., "Photobioreactor Engineering: Design and Performance". Biotechnol. Bioprocess Eng., 2003, vol. 8, No. 6, pp. 313-321. ISSN: 12268372.
Yang et al., "Progress in carbon dioxide separation and capture: A review". J.Env. Sci., 2008, vol. 20, pp. 14-27. ISSN: 10010742.
Zebib, "Microalgae Grown in Photobiorecators for Mass Production of Biofuel". Rutger University, Department of Bioenvironmental Engineering, Sep. 2008 http://www.water.rutgers.edu/Educational_Programs/Senior%20Design2008/Algae%20to%20Energy%20Report. pdf.
Tarik Zebib, "Microalgae Grown in Photobioreactors for Mass Production of Biofuel," *Rutgers University, Department of Bioenvironmental Engineering*, Sep. 30, 2008 (pp. 1-15).
Office Communication in Chinese Filing No. 201180035594.4/ Chinese Issuing No. 2014022101011280 dated Feb. 26, 2014.
Sun, et al., "An Experiment on Enclosed and Constant Culture of Marine Microalgae" Fisheries Science. 22(3):22-24, 2003 (in Chinese with English Abstract).
Final Office Action issued in U.S. Appl. No. 13/021,489 dated Nov. 29, 2013, (65 pages).
Final Office Action issued in U.S. Appl. No. 13/659,693 dated Feb. 20, 2014, (16 pages).
Hendershot et al., "Use Oxygen to Improve Combustion and Oxidation," American Institute of Chemical Engineers (AIChE), Chemical Engineering Progress, 57-60 (2010).
http://www.britannica.com/EBchecked/topic/108636/chemical-element/81245/Theatmosphere on May 13, 2013.
International Search Report and Written Opinion; Application No. PCT/CA2013/000908; dated Jan. 23, 2014; 12 pages.

International Search Report and Written Opinion; Application No. PCT/CA2013/000904; dated Feb. 7, 2014; 10 pages.
Kunjapur et al., "Photobioreactor Design for Commercial Biofuel Production from Microalgae," Ind. Eng. Chem. Res., 49:3516-3526 (2010).
Myklestad et al., "A photobioreactor with pH control: demonstration by growth of the marine diatom Skeletonema costatum," Journal of Plankton Research, 24(6):557-563 (2002).
Office Action issued in CN2014022101011280 dated Feb. 26, 2014 with translation (20 pages).
Office Action issued in U.S. Appl. No. 13/021,489 dated Mar. 18, 2013, (52 pages).
Office Action issued in U.S. Appl. No. 13/022,396 dated Dec. 18, 2012, (19 pages).
Office Action issued in U.S. Appl. No. 13/022,508 dated Feb. 13, 2014 (13 pages).
Office Action issued in U.S. Appl. No. 13/659,693 dated May 24, 2013, (19 pages).
Office Action issued in U.S. Appl. No. 13/659,714 dated May 24, 2013, (17 pages).
Response to Office Action issued in U.S. Appl. No. 13/021,489 dated Mar. 18, 2013, filed Sep. 18, 2013 (20 pages).
Response to Office Action issued in U.S. Appl. No. 13/659,693 dated May 24, 2013, filed Oct. 24, 2013 (14 pages).
Response to Restriction Requirement issued in U.S. Appl. No. 13/022,508 dated Sep. 18, 2013, filed Oct. 18, 2013 (1 page).
Restriction Requirement issued in U.S. Appl. No. 13/022,508 dated Sep. 18, 2013, (6 pages).
Restriction Requirement issued in U.S. Appl. No. 13/095,490 dated Apr. 11, 2014, (8 pages).
Sun et al., "An Experiment on Enclosed and Constant Culture of Marine Microalgae," Fisheries Science, 22(3):22-24 (2003) (with abstract translation).
Douskova, I. et al., Simultavious flue gas bioremediation and reduction of microalgal biomass production costs:, Appl. Microbiol. Biotechnol., 2009, vol. 82, pp. 179-185 2009.
Lee, J-S., et al., "Review of advances in biological CO2 mitigation technology", Biotechnol, Bioprocess., vol. 8, p. s354-359 2003.
Office Action; CA Application No. 2799988 dated Aug. 18, 2020.
Office Action for U.S. Appl. No. 14/971,854 dated Apr. 21, 2021.
Examination Report for EP18 188 304.2 dated Jan. 12, 2021.
Office Action for U.S. Appl. No. 14/971,854 dated Feb. 11, 2022.
Communication in pursuant to Article 94(3) EPC, issued in connection with EP Patent Application 18188304.2, dated Apr. 5, 2022.
Examination Report issued in connection with AU Patent Application 2020250220, dated Feb. 14, 2022.
Examination Report issued in connection with Application GC 2011-18441, dated Dec. 17, 2018.
Office Action issued in connection with U.S. Appl. No. 14/971,854, dated Oct. 8, 2021.
Examination Report issued in connection with Application GC 2011-37439, dated Feb. 22, 2020.

\* cited by examiner

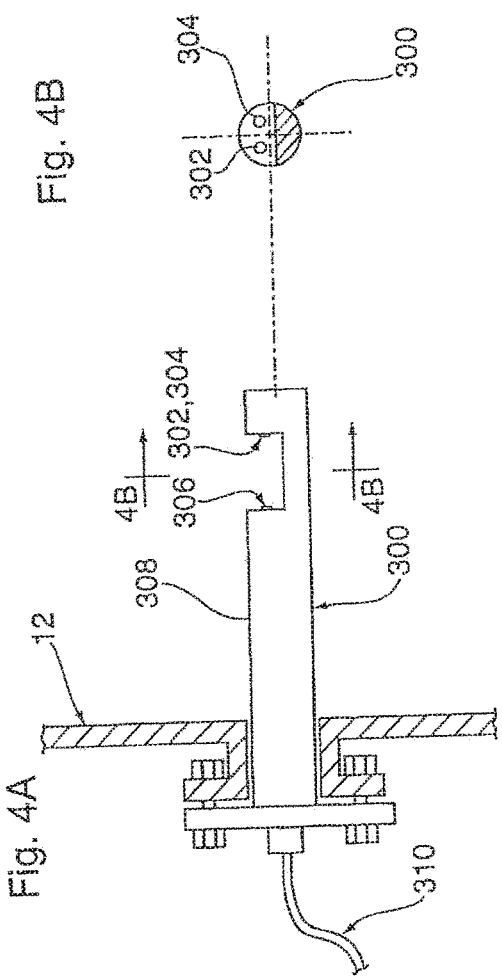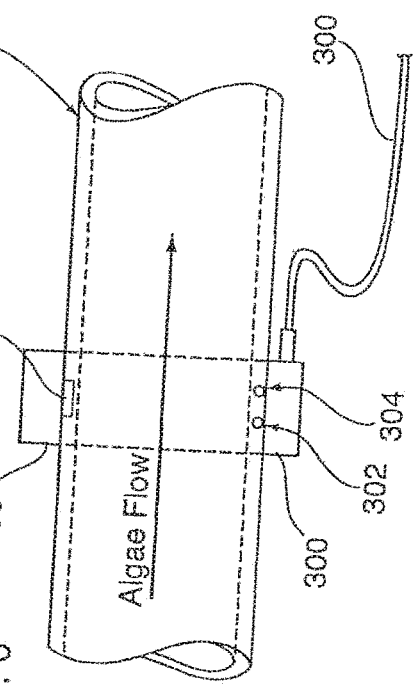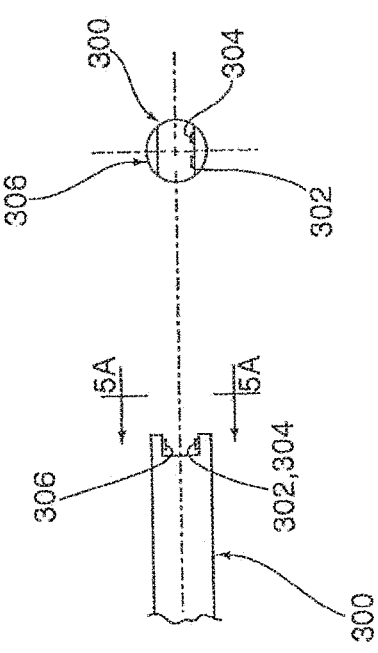

BIOMASS PRODUCTION

RELATED APPLICATIONS

This application is a continuation of U.S. patent application Ser. No. 13/327,541, filed on Dec. 15, 2011, which is a continuation-in-part of U.S. patent application Ser. No. 13/022,396, filed on Feb. 7, 2011, which is a continuation-in-part of U.S. patent application Ser. No. 12/784,172, filed on May 20, 2010. This application claims priority to Canadian Patent Application No. 2,738,516, filed on Apr. 29, 2011. This application is also a continuation-in-part of International (PCT) Application No. PCT/CA2011/000574, which has an international filing date of May 18, 2011, which PCT application is a continuation-in-part of U.S. patent application Ser. No. 12/784,215, filed on May 20, 2010, and is also a continuation-in-part of U.S. patent application Ser. No. 12/784,181, filed on May 20, 2010, and is also a continuation-in-part of U.S. patent application Ser. No. 12/784,172, filed on May 20, 2010, and is also a continuation-in-part of U.S. patent application Ser. No. 12/784,141, filed on May 20, 2010, and is also a continuation-in-part of U.S. application Ser. No. 12/784,126, filed on May 20, 2010, and is also a continuation-in-part of U.S. patent application Ser. No. 12/784,106, filed on May 20, 2010, and is also a continuation-in-part of U.S. application Ser. No. 13/022,396, filed on Feb. 7, 2011. This application is also a continuation-in-part of International (PCT) Application No. PCT/CA2011/001367, filed on Nov. 18, 2011. These applications are incorporated herein by reference in their entirety.

FIELD

The present disclosure relates to a process for growing biomass.

BACKGROUND

The cultivation of phototrophic organisms has been widely practised for purposes of producing a fuel source. Exhaust gases from industrial processes have also been used to promote the growth of phototrophic organisms by supplying carbon dioxide for consumption by phototrophic organisms during photosynthesis. By providing exhaust gases for such purpose, environmental impact is reduced and, in parallel a potentially useful fuel source is produced. Challenges remain, however, to render this approach more economically attractive for incorporation within existing facilities.

SUMMARY

In one aspect, there is provided a process of growing a phototrophic biomass in a reaction zone. The reaction zone includes a reaction mixture that is operative for effecting photosynthesis upon exposure to photosynthetically active light radiation, wherein the reaction mixture includes phototrophic biomass that is operative for growth within the reaction zone. While exposing the reaction mixture to photosynthetically active light radiation and effecting growth of the phototrophic biomass in the reaction zone, wherein the effected growth includes growth effected by photosynthesis, and while discharging phototrophic biomass from the reaction zone, when a phototrophic biomass growth indicator is different than a target value of the phototrophic biomass growth indicator, modulating the rate of discharge of mass of the phototrophic biomass from the reaction zone, wherein the target value of the phototrophic biomass growth indicator is based upon a predetermined growth rate of the phototrophic biomass within the reaction mixture which is disposed within the reaction zone and is being exposed to photosynthetically active light radiation.

In another aspect, there is provided another process of growing a phototrophic biomass in a reaction zone. The reaction zone includes a production purpose reaction mixture that is operative for effecting photosynthesis upon exposure to photosynthetically active light radiation, wherein the production purpose reaction mixture includes production purpose phototrophic biomass that is operative for growth within the reaction zone. While exposing the reaction mixture to photosynthetically active light radiation and effecting growth of the production purpose phototrophic biomass in the reaction zone, wherein the effected growth includes growth effected by photosynthesis, and while discharging production purpose phototrophic biomass from the reaction zone, when a phototrophic biomass growth indicator is different than a predetermined target value of the phototrophic biomass growth indicator, modulating the rate of discharge of mass of the production purpose phototrophic biomass from the reaction zone, wherein the target value of the phototrophic biomass growth indicator is based upon a predetermined growth rate of the production purpose phototrophic biomass within the reaction mixture which is disposed within the reaction zone and is being exposed to photosynthetically active light radiation. The predetermination of the target value includes supplying an evaluation purpose reaction mixture that is representative of the production purpose reaction mixture and is operative for effecting photosynthesis upon exposure to photosynthetically active light radiation, such that the phototrophic biomass of the evaluation purpose reaction mixture is an evaluation purpose phototrophic biomass that is representative of the production purpose phototrophic biomass. While the evaluation purpose reaction mixture disposed in the reaction zone is exposed to photosynthetically active light radiation and growth of the evaluation purpose phototrophic biomass is being effected within the evaluation purpose reaction mixture, at least periodically detecting the phototrophic biomass growth indicator to provide a plurality of detected values of the phototrophic biomass growth indicator that have been detected during a time period, and calculating growth rates of the evaluation purpose phototrophic biomass based on the plurality of detected values of the phototrophic biomass growth indicator such that a plurality of growth rates of the evaluation purpose phototrophic biomass are determined during the time period A relationship between the growth rate of the evaluation purpose phototrophic biomass and the phototrophic biomass growth indicator is established, based on the calculated growth rates and the detected values of the phototrophic biomass growth indicator upon which the calculated growth rates have been based, such that the established relationship between the growth rate of the evaluation purpose phototrophic biomass and the phototrophic biomass growth indicator is representative of a relationship between the growth rate of the production purpose phototrophic biomass within the reaction zone and the phototrophic biomass growth indicator, and such that the relationship between the growth rate of the production purpose phototrophic biomass within the reaction zone and the phototrophic biomass growth indicator is thereby determined. The predetermined growth rate of the production purpose phototrophic biomass is selected. The phototrophic biomass growth indicator target value is defined as the phototrophic biomass growth indicator at which the predetermined growth rate is being effected based on the determined relationship between the growth rate of the production purpose phototrophic biomass within the reaction zone and the phototrophic biomass growth indicator, such that the correlation between the phototrophic biomass growth indicator target value and the predetermined growth rate is also thereby effected.

In another aspect, there is provided another process for growing a phototrophic biomass in a reaction zone. The reaction zone includes a reaction mixture that is operative for effecting photosynthesis upon exposure to photosynthetically active light radiation, wherein the reaction mixture includes phototrophic biomass that is operative for growth within the reaction zone. While exposing the reaction mixture disposed in the reaction zone to photosynthetically active light radiation and growth of the phototrophic biomass is being effected within the reaction mixture, discharging mass of the phototrophic biomass from the reaction zone at a rate that is within 10% of the rate at which the growth of mass of the phototrophic biomass is being effected within the reaction zone. The effected growth of the phototrophic biomass within the reaction zone is being effected at a rate that is at least 90% of the maximum rate of growth of mass of the phototrophic biomass within the reaction mixture which is disposed in reaction zone and is being exposed to the photosynthetically active light radiation.

In another aspect, there is provided another process for growing phototrophic biomass in a reaction zone. The reaction zone includes a reaction mixture that is operative for effecting photosynthesis upon exposure to photosynthetically active light radiation, wherein the reaction mixture includes phototrophic biomass that is operative for growth within the reaction zone. While exposing the reaction mixture to photosynthetically active light radiation and effecting growth of the phototrophic biomass within the reaction mixture disposed in the reaction zone, wherein the effected growth of the phototrophic biomass includes growth which is effected by the photosynthesis, discharging phototrophic biomass from the reaction zone such that the rate of discharge of mass of the phototrophic biomass is within 10% of the rate at which the growth of mass of the phototrophic biomass is being effected.

In another aspect, there is provided a process for growing a phototrophic biomass in a reaction zone, wherein the reaction zone includes a reaction mixture that is operative for effecting photosynthesis upon exposure to photosynthetically active light radiation, wherein the reaction mixture includes phototrophic biomass that is operative for growth within the reaction zone, wherein the growth of the phototrophic biomass includes that which is effected by the photosynthesis, comprising: while the gaseous exhaust material is being discharged by the gaseous exhaust material producing process, wherein any of the gaseous exhaust material being supplied to the reaction zone defines a gaseous exhaust material reaction zone supply, supply of the gaseous exhaust material reaction zone supply to the reaction zone is modulated based on detection of at least one carbon dioxide processing capacity indicator.

In another aspect, there is provided a process for growing a phototrophic biomass in a reaction zone, wherein the reaction zone includes a reaction mixture that is operative for effecting photosynthesis upon exposure to photosynthetically active light radiation, wherein the reaction mixture includes phototrophic biomass that is operative for growth within the reaction zone, wherein the growth of the phototrophic biomass includes that which is effected by the photosynthesis, comprising: while the gaseous exhaust material is being discharged by the gaseous exhaust material producing process, and while at least a fraction of the gaseous exhaust material is being supplied to the reaction zone, wherein the at least a fraction of the gaseous exhaust material which is being supplied to the reaction zone defines a gaseous exhaust material reaction zone supply, and there is effected a reduction in the molar rate of supply, or the termination of the supply, of the gaseous exhaust material reaction zone supply being supplied to the reaction zone, the process further includes initiating the supply of a supplemental gas-comprising material, or increasing the molar rate of supply of a supplemental gas-comprising material, to the reaction zone.

In another aspect, there is provided a process for growing a phototrophic biomass in a reaction zone, wherein the reaction zone includes a reaction mixture that is operative for effecting photosynthesis upon exposure to photosynthetically active light radiation, wherein the reaction mixture includes phototrophic biomass that is operative for growth within the reaction zone, wherein the growth of the phototrophic biomass includes that which is effected by the photosynthesis, comprising: supplying gaseous exhaust material reaction zone supply to the reaction zone, wherein the gaseous exhaust material reaction zone supply is defined by at least a fraction of gaseous exhaust material produced by a gaseous exhaust material producing process, wherein the gaseous exhaust material reaction zone supply includes carbon dioxide, and supplying a supplemental aqueous material supply from a container to the reaction zone, wherein the supplemental aqueous material supply includes aqueous material that has been condensed from the gaseous exhaust material reaction zone supply and collected in the container, wherein the condensing of the aqueous material is effected while the gaseous exhaust material reaction zone supply is being cooled before being supplied to the reaction zone.

In another aspect, there is provided a process for growing a phototrophic biomass in a reaction zone, wherein the reaction zone includes a reaction mixture that is operative for effecting photosynthesis upon exposure to photosynthetically active light radiation, wherein the reaction mixture includes phototrophic biomass that is operative for growth within the reaction zone, wherein the growth of the phototrophic biomass includes that which is effected by the photosynthesis, comprising: while carbon dioxide is being discharged by the gaseous exhaust material producing process, and while at least a fraction of the discharged carbon dioxide is being supplied to the reaction zone, wherein the at least a fraction of the discharged carbon dioxide which is being supplied to the reaction zone defines a discharged carbon dioxide reaction zone supply, at least one material input to the reaction zone is modulated based on, at least, the molar rate at which the discharged carbon dioxide reaction zone supply is being supplied to the reaction zone.

In another aspect, there is provided a process for growing a phototrophic biomass in a reaction zone, wherein the reaction zone includes a reaction mixture that is operative for effecting photosynthesis upon exposure to photosynthetically active light radiation, wherein the reaction mixture includes phototrophic biomass that is operative for growth within the reaction zone, wherein the growth of the phototrophic biomass includes that which is effected by the photosynthesis, comprising: while carbon dioxide is being discharged by the gaseous exhaust material producing process, and while at least a fraction of the discharged carbon dioxide is being supplied to the reaction zone, wherein the at least a fraction of the discharged carbon dioxide which is being supplied to the reaction zone defines a discharged carbon dioxide reaction zone supply, at least one material input to the reaction zone is modulated based on, at least, an indication of the molar rate at which the discharged carbon dioxide reaction zone supply is being supplied to the reaction zone.

In another aspect, there is provided a process for growing a phototrophic biomass in a reaction zone, wherein the reaction zone includes a reaction mixture that is operative for effecting photosynthesis upon exposure to photosynthetically active light radiation, wherein the reaction mixture includes phototrophic biomass that is operative for growth within the reaction zone, wherein the growth of the phototrophic biomass includes that which is effected by the photosynthesis, comprising: while carbon dioxide is being discharged by the gaseous exhaust material producing process, and while at least a fraction of the discharged carbon dioxide is being supplied to the reaction zone, wherein the at least a fraction of the discharged carbon dioxide which is being supplied to the reaction zone defines a discharged carbon dioxide reaction zone supply, when an indication of a change in the molar rate of supply of the discharged carbon dioxide reaction zone supply being supplied to the reaction zone is detected, modulation of at least one material input to the reaction zone is effected.

In another aspect, there is provided a process for growing a phototrophic biomass in a reaction zone, wherein the reaction zone includes a reaction mixture that is operative for effecting photosynthesis upon exposure to photosynthetically active light radiation, wherein the reaction mixture includes phototrophic biomass that is operative for growth within the reaction zone, wherein the growth of the phototrophic biomass includes that which is effected by the photosynthesis, comprising: while carbon dioxide is being discharged by the gaseous exhaust material producing process, and while at least a fraction of the discharged carbon dioxide is being supplied to the reaction zone, wherein the at least a fraction of the discharged carbon dioxide which is being supplied to the reaction zone defines a discharged carbon dioxide reaction zone supply, when a decrease in the molar rate of supply of the discharged carbon dioxide reaction zone supply being supplied to the reaction zone is detected, or when an indication of a decrease in the molar rate of supply of the discharged carbon dioxide reaction zone supply being supplied to the reaction zone is detected, either the molar rate of supply of a supplemental carbon dioxide supply to the reaction zone is increased, or supply of the supplemental carbon dioxide supply to the reaction zone is initiated.

In another aspect, there is provided a process for growing a phototrophic biomass in a reaction zone, wherein the reaction zone includes a reaction mixture that is operative for effecting photosynthesis upon exposure to photosynthetically active light radiation, wherein the reaction mixture includes phototrophic biomass that is operative for growth within the reaction zone, wherein the growth of the phototrophic biomass includes that which is effected by the photosynthesis, comprising: prior to supplying reaction zone carbon dioxide supply to the reaction zone at a pressure sufficient to effect flow of the reaction zone carbon dioxide supply through a vertical extent of the reaction zone of at least a seventy (70) inches, increasing pressure of the reaction zone carbon dioxide supply by flowing the reaction zone carbon dioxide supply through an eductor or a jet pump.

In another aspect, there is provided a process for growing a phototrophic biomass in a reaction zone, wherein the reaction zone includes a reaction mixture that is operative for effecting photosynthesis upon exposure to photosynthetically active light radiation, wherein the reaction mixture includes phototrophic biomass that is operative for growth within the reaction zone, wherein the growth of the phototrophic biomass includes that which is effected by the photosynthesis, comprising: prior to supplying reaction zone carbon dioxide supply to the reaction zone at a pressure sufficient to effect flow of the reaction zone carbon dioxide supply through a vertical extent of the reaction zone of at least a seventy (70) inches, transferring pressure energy to the reaction zone carbon dioxide supply from a motive fluid flow using the venturi effect.

In another aspect, there is provided a process for growing a phototrophic biomass in a reaction zone, wherein the reaction zone includes a reaction mixture that is operative for effecting photosynthesis upon exposure to photosynthetically active light radiation, wherein the reaction mixture includes phototrophic biomass that is operative for growth within the reaction zone, wherein the growth of the phototrophic biomass includes that which is effected by the photosynthesis, comprising: while a reaction zone feed material is supplied to the reaction zone, supplying the reaction zone feed material with a supplemental gaseous dilution agent, wherein the molar concentration of carbon dioxide of the supplemental gaseous dilution agent is less than the molar concentration of carbon dioxide of the gaseous exhaust material reaction zone supply which is being supplied to the reaction zone feed material.

In another aspect, there is provided a process for growing a phototrophic biomass in a reaction zone, wherein the reaction zone includes a reaction mixture that is operative for effecting photosynthesis upon exposure to photosynthetically active light radiation, wherein the reaction mixture includes phototrophic biomass that is operative for growth within the reaction zone, wherein the growth of the phototrophic biomass includes that which is effected by the photosynthesis, comprising: while a carbon dioxide concentrated supply is being supplied, admixing the carbon dioxide concentrated supply with a supplemental gaseous dilution agent to effect production of a diluted carbon dioxide supply, wherein the molar concentration of carbon dioxide of the diluted carbon dioxide supply is less than the molar concentration of carbon dioxide of the carbon dioxide concentrated supply; and supplying at least a fraction of the diluted carbon dioxide reaction zone supply to the reaction zone.

BRIEF DESCRIPTION OF THE DRAWINGS

The process of the preferred embodiments of the invention will now be described with the following accompanying drawing:

FIG. 4A is a sectional side elevation view of an embodiment of a mass concentration sensor mounted to a vessel;

FIG. 4B is a view of the sensor of FIG. 4A taken along lines 4B-4B;

FIG. 5A is a fragmentary side elevation view of another embodiment of a mass concentration sensor configured for mounting to a vessel;

FIG. 5B is a view of the sensor of FIG. 5B taken along lines 5A-5A;

FIG. 6 is a schematic illustration of another embodiment of a mass concentration sensor;

DETAILED DESCRIPTION

Reference throughout the specification to "some embodiments" means that a particular feature, structure, or characteristic described in connection with some embodiments are not necessarily referring to the same embodiments. Furthermore, the particular features, structure, or characteristics may be combined in any suitable manner with one another.

Figure 1:
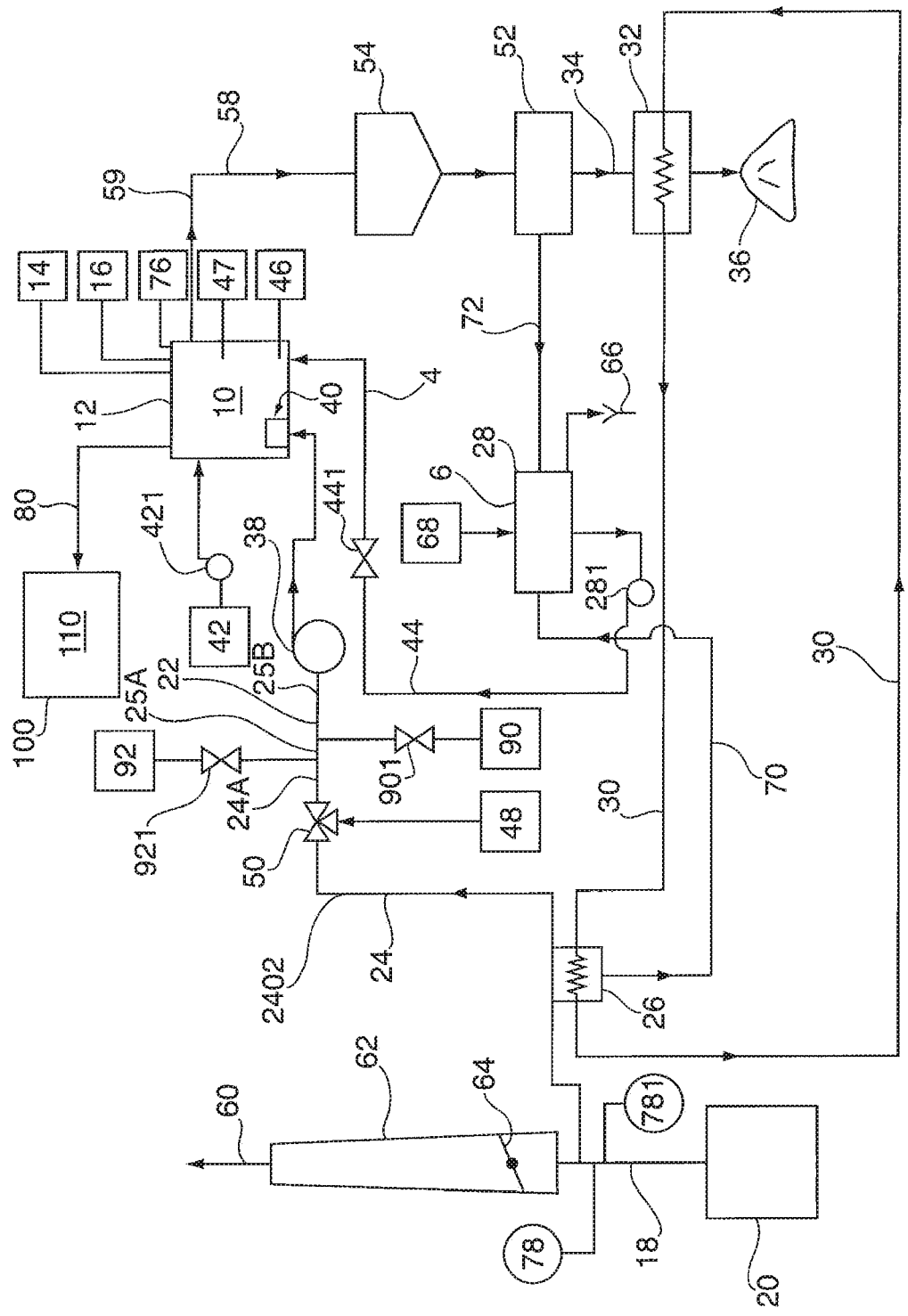
FIG. 1 is a process flow diagram of an embodiment of the process.

Referring to FIG. 1, there is provided a process of growing a phototrophic biomass in a reaction zone 10. The reaction zone 10 includes a reaction mixture that is operative for effecting photosynthesis upon exposure to photosynthetically active light radiation. The reaction mixture includes phototrophic biomass material, carbon dioxide, and water. In some embodiments, the reaction zone includes phototrophic biomass and carbon dioxide disposed in an aqueous medium. Within the reaction zone, the phototrophic biomass is disposed in mass transfer communication with both of carbon dioxide and water. In some embodiments, for example, the reaction mixture includes phototrophic biomass disposed in an aqueous medium, and carbon dioxide-enriched phototrophic biomass is provided upon the receiving of carbon dioxide by the phototrophic biomass.

"Phototrophic organism" is an organism capable of phototrophic growth in the aqueous medium upon receiving light energy, such as plant cells and micro-organisms. The phototrophic organism is unicellular or multicellular. In some embodiments, for example, the phototrophic organism is an organism which has been modified artificially or by gene manipulation. In some embodiments, for example, the phototrophic organism is an algae. In some embodiments, for example, the algae is microalgae.

"Phototrophic biomass" is at least one phototrophic organism. In some embodiments, for example, the phototrophic biomass includes more than one species of phototrophic organisms.

"Reaction zone 10" defines a space within which the growing of the phototrophic biomass is effected. In some embodiments, for example, the reaction zone 10 is provided in a photobioreactor 12. In some embodiments, for example, pressure within the reaction zone is atmospheric pressure.

"Photobioreactor 12" is any structure, arrangement, land formation or area that provides a suitable environment for the growth of phototrophic biomass. Examples of specific structures which can be used is a photobioreactor 12 by providing space for growth of phototrophic biomass using light energy include, without limitation, tanks, ponds, troughs, ditches, pools, pipes, tubes, canals, and channels. Such photobioreactors may be either open, closed, partially closed, covered, or partially covered. In some embodiments, for example, the photobioreactor 12 is a pond, and the pond is open, in which case the pond is susceptible to uncontrolled receiving of materials and light energy from the immediate environments. In other embodiments, for example, the photobioreactor 12 is a covered pond or a partially covered pond, in which case the receiving of materials from the immediate environment is at least partially interfered with. The photobioreactor 12 includes the reaction zone 10 which includes the reaction mixture. In some embodiments, the photobioreactor 12 is configured to receive a supply of phototrophic reagents (and, in some of these embodiments, optionally, supplemental nutrients), and is also configured to effect discharge of phototrophic biomass which is grown within the reaction zone 10. In this respect, in some embodiments, the photobioreactor 12 includes one or more inlets for receiving the supply of phototrophic reagents and supplemental nutrients, and also includes one or more outlets for effecting the recovery or harvesting of biomass which is grown within the reaction zone 10. In some embodiments, for example, one or more of the inlets are configured to be temporarily sealed for periodic or intermittent time intervals. In some embodiments, for example, one or more of the outlets are configured to be temporarily sealed or substantially sealed for periodic or intermittent time intervals. The photobioreactor 12 is configured to contain the reaction mixture which is operative for effecting photosynthesis upon exposure to photosynthetically active light radiation. The photobioreactor 12 is also configured so as to establish photosynthetically active light radiation (for example, a light of a wavelength between about 400-700 nm, which can be emitted by the sun or another light source) within the photobioreactor 12 for exposing the phototrophic biomass. The exposing of the reaction mixture to the photosynthetically active light radiation effects photosynthesis and growth of the phototrophic biomass. In some embodiments, for example, the established light radiation is provided by an artificial light source 14 disposed within the photobioreactor 12. For example, suitable artificial lights sources include submersible fiber optics or light guides, light-emitting diodes ("LEDs"), LED strips and fluorescent lights. Any LED strips known in the art can be adapted for use in the photobioreactor 12. In the case of the submersible LEDs, in some embodiments, for example, energy sources include alternative energy sources, such as wind, photovoltaic cells, fuel cells, etc. to supply electricity to the LEDs. Fluorescent lights, external or internal to the photobioreactor 12, can be used as a back-up system. In some embodiments, for example, the established light is derived from a natural light source 16 which has been transmitted from externally of the photobioreactor 12 and through a transmission component. In some embodiments, for example, the transmission component is a portion of a containment structure of the photobioreactor 12 which is at least partially transparent to the photosynthetically active light radiation, and which is configured to provide for transmission of such light to the reaction zone 10 for receiving by the phototrophic biomass. In some embodiments, for example, natural light is received by a solar collector, filtered with selective wavelength filters, and then transmitted to the reaction zone 10 with fiber optic material or with a light guide. In some embodiments, for example, both natural and artificial lights sources are provided for effecting establishment of the photosynthetically active light radiation within the photobioreactor 12.

"Aqueous medium" is an environment that includes water. In some embodiments, for example, the aqueous medium also includes sufficient nutrients to facilitate viability and growth of the phototrophic biomass. In some embodiments, for example, supplemental nutrients may be included such as one of, or both of, $NO_x$ and $SO_x$. Suitable aqueous media are discussed in detail in: Rogers, L. J. and Gallon J. R. "Biochemistry of the Algae and Cyanobacteria," Clarendon Press Oxford, 1988; Burlew, John S. "Algal Culture: From Laboratory to Pilot Plant." Carnegie Institution of Washington Publication 600. Washington, D.C., 1961 (hereinafter "Burlew 1961"); and Round, F. E. The Biology of the Algae. St Martin's Press, New York, 1965; each of which is incorporated herein by reference). A suitable supplemental nutrient composition, known as "Bold's Basal Medium", is described in Bold, H. C. 1949, *The morphology of Chlamydomonas chlamydogama sp. nov. Bull. Torrey Bot. Club.* 76: 101-8 (see also Bischoff, H. W. and Bold, H. C. 1963, *Phycological Studies IV. Some soil algae from Enchanted Rock* and *related algal* species, Univ. Texas Publ. 6318: 1-95, and Stein, J. (ED.) *Handbook of Phycological Methods, Culture methods and growth measurements*, Cambridge University Press, pp. 7-24).

"Modulating", with respect to a process variable, such as an input or an output, means any one of initiating, terminating, increasing, decreasing, or otherwise changing the process parameter, such as that of an input or an output.

In some embodiments, the process includes supplying the reaction zone 10 with carbon dioxide. In some of these embodiments, for example, the carbon dioxide supplied to the reaction zone 10 is derived from a gaseous exhaust material 18 which includes carbon dioxide. In this respect, in some embodiments, the carbon dioxide is supplied by a gaseous exhaust material producing process 20, and the supplying is, therefore, effected from the gaseous exhaust material 18 being discharged by a gaseous exhaust material producing process 20. In some embodiments, for example, at least a fraction of the carbon dioxide being discharged by the gaseous exhaust material producing process 20 is supplied to the reaction zone 10, wherein the at least a fraction of the discharged carbon dioxide which is being supplied to the reaction zone 10 defines a discharged carbon dioxide reaction zone supply. In some embodiments, for example, at least a fraction of the gaseous exhaust material 18 being discharged by the gaseous exhaust material producing process 20 is supplied to the reaction zone 10, wherein the at least a fraction of the gaseous exhaust material 18 which is being supplied to the reaction zone 10 defines gaseous exhaust material reaction zone supply 24, such that the discharged carbon dioxide reaction zone supply is supplied to the reaction zone 10 as a portion of the gaseous exhaust material reaction zone supply 24 (along with other non-carbon dioxide materials deriving from the gaseous exhaust material 18). In some of these embodiments, for example, the exposing of the phototrophic biomass disposed in the reaction zone 10 to photosynthetically active light radiation is effected while the gaseous exhaust material reaction zone supply 24 is being supplied to the reaction zone 10.

In some embodiments, for example, the gaseous exhaust material 18 includes a carbon dioxide concentration of at least 2 volume % based on the total volume of the gaseous exhaust material 18. In this respect, in some embodiments, for example, the gaseous exhaust material reaction zone supply 24 includes a carbon dioxide concentration of at least 2 volume % based on the total volume of the gaseous exhaust material reaction zone supply 24. In some embodiments, for example, the gaseous exhaust material 18 includes a carbon dioxide concentration of at least 4 volume % based on the total volume of the gaseous exhaust material 18. In this respect, in some embodiments, for example, the gaseous exhaust material reaction zone supply 24 includes a carbon dioxide concentration of at least 4 volume % based on the total volume of the gaseous exhaust material reaction zone supply 24. In some embodiments, for example, the gaseous exhaust material reaction zone supply 24 also includes one of, or both of, $NO_x$ and $SO_x$.

In some embodiments, for example, the at least a fraction of the gaseous exhaust material 18 being supplied to the reaction zone 10 has been treated prior to being supplied to the reaction zone 10 so as to effect removal of undesirable components of the gaseous exhaust material 18 such that the material composition of the at least a fraction of the gaseous material 18 being supplied to the reaction zone 10 is different relative to the material composition of the gaseous exhaust material 18 being discharged from the gaseous exhaust material producing process 20.

The gaseous exhaust material producing process 20 includes any process which effects production and discharge of the gaseous exhaust material 18. In some embodiments, for example, at least a fraction of the gaseous exhaust material 18 being discharged by the gaseous exhaust material producing process 20 is supplied to the reaction zone 10. The at least a fraction of the gaseous exhaust material 18, being discharged by the gaseous exhaust material producing process 20, and supplied to the reaction zone 10, includes carbon dioxide derived from the gaseous exhaust material producing process 20. In some embodiments, for example, the gaseous exhaust material producing process 20 is a combustion process. In some embodiments, for example, the combustion process is effected in a combustion facility. In some of these embodiments, for example, the combustion process effects combustion of a fossil fuel, such as coal, oil, or natural gas. For example, the combustion facility is any one of a fossil fuel-fired power plant, an industrial incineration facility, an industrial furnace, an industrial heater, or an internal combustion engine. In some embodiments, for example, the combustion facility is a cement kiln.

Reaction zone feed material 22 is supplied to the reaction zone 10 such that carbon dioxide of the reaction zone feed material 22 is received within the reaction zone 10. At least a fraction of the carbon dioxide of the reaction zone feed material 22 is derived from the gaseous exhaust material 18. During at least some periods of operation of the process, at least a fraction of the reaction zone feed material 22 is supplied by the gaseous exhaust material 18 which is discharged from the gaseous exhaust material producing process 20. As discussed above, any of the gaseous exhaust material 18 that is supplied to the reaction zone 10 is supplied as a gaseous exhaust material reaction zone supply 24. In some of these embodiments, for example, the exposing of the phototrophic biomass disposed in the reaction zone 10 to photosynthetically active light radiation is effected while the gaseous exhaust material reaction zone supply 24 is being supplied to the reaction zone 10. It is understood that, in some embodiments, not the entirety of the gaseous exhaust material 18 is necessarily supplied to the reaction zone 10 as the gaseous exhaust material reaction zone supply 24, such that the reaction zone feed material 22 includes the gaseous exhaust material reaction zone supply 24. It is also understood that, in some embodiments, the gaseous exhaust material 18, or at least a fraction thereof, is not necessarily supplied to the reaction zone 10 as the gaseous exhaust material reaction zone supply 24 for the entire time period during which the process is operational. The gaseous exhaust material reaction zone supply 24 includes carbon dioxide. In some of these embodiments, for example, the gaseous exhaust material reaction zone supply 24 is at least a fraction of the gaseous exhaust material 18 being discharged by the gaseous exhaust material producing process 20. In some cases, the entirety of the gaseous exhaust material 18 discharged by the gaseous exhaust material producing process 20 is supplied to the gaseous exhaust material reaction zone supply 24.

With respect to the reaction zone feed material 22, the reaction zone feed material 22 is a fluid. In some embodiments, for example, the reaction zone feed material 22 is a gaseous material. In some embodiments, for example, the reaction zone feed material 22 includes gaseous material disposed in liquid material. In some embodiments, for example, the liquid material is an aqueous material. In some of these embodiments, for example, at least a fraction of the gaseous material is dissolved in the liquid material. In some of these embodiments, for example, at least a fraction of the gaseous material is disposed as a gas dispersion in the liquid material. In some of these embodiments, for example, and during at least some periods of operation of the process, the gaseous material of the reaction zone feed material 22 includes carbon dioxide supplied by the gaseous exhaust material reaction zone supply 24. In some of these embodiments, for example, the reaction zone feed material 22 is supplied to the reaction zone 10 as a flow. In some embodiments, for example, a flow of reaction zone feed material 22 includes a flow of the gaseous exhaust material reaction zone feed material supply 24. In some embodiments, for example, a flow of reaction zone feed material 22 is a flow of the gaseous exhaust material reaction zone feed material supply 24.

In some embodiments, for example, the reaction zone feed material 22 is supplied to the reaction zone 10 as one or more reaction zone feed material flows. For example, each of the one or more reaction zone feed material flows is flowed through a respective reaction zone feed material fluid passage. In some of those embodiments where there are more than one reaction zone feed material flow, the material composition varies between the reaction zone feed material flows.

In some embodiments, for example, the reaction zone feed material 22 is cooled prior to supply to the reaction zone 10 so that the temperature of the reaction zone feed material 22 aligns with a suitable temperature at which the phototrophic biomass can grow In some embodiments, for example, the gaseous exhaust material reaction zone supply 24 being supplied to the reaction zone material 22 is disposed at a temperature of between 110 degrees Celsius and 150 degrees Celsius. In some embodiments, for example, the temperature of the gaseous exhaust material reaction zone supply 24 is about 132 degrees Celsius. In some embodiments, the temperature at which the gaseous exhaust material reaction zone supply 24 is disposed is much higher than this, and, in some embodiments, such as the gaseous exhaust material reaction zone supply 24 from a steel mill, the temperature is over 500 degrees Celsius. In some embodiments, for example, the reaction zone feed material 22, which includes the gaseous exhaust material reaction zone supply 24, is cooled to between 20 degrees Celsius and 50 degrees Celsius (for example, about 30 degrees Celsius). In some embodiments, the reaction zone feed material 22 is defined by the gaseous exhaust material reaction zone supply 24. Supplying the reaction zone feed material 22 at higher temperatures could hinder growth, or even kill, the phototrophic biomass in the reaction zone 10. In some of these embodiments, in effecting the cooling of the reaction zone feed material 22, at least a fraction of any water vapour of the gaseous exhaust material reaction zone supply 24 is condensed in a heat exchanger 26 (such as a condenser) and separated from the reaction zone feed material 22 as an aqueous material 70. In some embodiments, the resulting aqueous material 70 is supplied to a container 28 (described below) where it provides supplemental aqueous material supply 44 for supply to the reaction zone 10. In some embodiments, the condensing effects heat transfer from the reaction zone feed material 22 to a heat transfer medium 30, thereby raising the temperature of the heat transfer medium 30 to produce a heated heat transfer medium 30, and the heated heat transfer medium 30 is then supplied (for example, flowed) to a dryer 32 (discussed below), and heat transfer is effected from the heated heat transfer medium 30 to an intermediate concentrated reaction zone product 34 to effect drying of the intermediate concentrated reaction zone product 34 and thereby effect production of the final reaction zone product 36. In some embodiments, for example, after being discharged from the dryer 32, the heat transfer medium 30 is recirculated to the heat exchanger 26. Examples of a suitable heat transfer medium 30 include thermal oil and glycol solution.

In some embodiments, for example, the supply of the reaction zone feed material 22 to the reaction zone 10 effects agitation of at least a fraction of the phototrophic biomass disposed in the reaction zone 10. In this respect, in some embodiments, for example, the reaction zone feed material 22 is introduced to a lower portion of the reaction zone 10. In some embodiments, for example, the reaction zone feed material 22 is introduced from below the reaction zone 10 so as to effect mixing of the contents of the reaction zone 10. In some of these embodiments, for example, the effected mixing (or agitation) is such that any difference in concentration of mass of the phototrophic biomass between any two points in the reaction zone 10 is less than 20%. In some embodiments, for example, any difference in the mass concentration of the phototrophic biomass between any two points in the reaction zone 10 is less than 10%. In some of these embodiments, for example, the effected mixing is such that a homogeneous suspension is provided in the reaction zone 10. In those embodiments with a photobioreactor 12, for some of these embodiments, for example, the supply of the reaction zone feed material 22 is co-operatively configured with the photobioreactor 12 so as to effect the desired agitation of the at least a fraction of the phototrophic biomass disposed in the reaction zone 10.

With further respect to those embodiments where the supply of the reaction zone feed material 22 to the reaction zone 10 effects agitation of at least a fraction of the phototrophic biomass disposed in the reaction zone 10, in some of these embodiments, for example, the reaction zone feed material 22 flows through a gas injection mechanism, such as a sparger 40, before being introduced to the reaction zone 10. In some of these embodiments, for example, the sparger 40 provides reaction zone feed material 22 as a gas-liquid mixture, including fine gas bubbles entrained in a liquid phase, to the reaction zone 10 in order to maximize the interface contact area between the phototrophic biomass and the carbon dioxide (and, in some embodiments, for example, one of, or both of, SOX and NOX) of the reaction zone feed material 22. This assists the phototrophic biomass in efficiently absorbing the carbon dioxide (and, in some embodiments, other gaseous components) required for photosynthesis, thereby promoting the optimization of the growth rate of the phototrophic biomass. As well, in some embodiments, for example, the sparger 40 provides reaction zone feed material 22 in larger bubbles that agitate the phototrophic biomass in the reaction zone 10 to promote mixing of the components of the reaction zone 10. An example of a suitable sparger 40 is EDI FLEXAIR™ T-Series Tube Diffuser Model 91 X 1003 supplied by Environmental Dynamics Inc of Columbia, Mo. In some embodiments, for example, this sparger 40 is disposed in a photobioreactor 12 having a reaction zone 10 volume of 6000 litres and with an algae concentration of between 0.8 grams per litre and 1.5 grams per litre, and the reaction zone feed material 22 is a gaseous fluid flow supplied at a flowrate of between 10 cubic feet per minute and 20 cubic feet per minute, and at a pressure of about 68 inches of water.

With respect to the sparger 40, in some embodiments, for example, the sparger 40 is designed to consider the fluid head of the reaction zone 10, so that the supplying of the reaction zone feed material 22 to the reaction zone 10 is effected in such a way as to promote the optimization of carbon dioxide absorption by the phototrophic biomass. In this respect, bubble sizes are regulated so that they are fine enough to promote optimal carbon dioxide absorption by the phototrophic biomass from the reaction zone feed material. Concomitantly, the bubble sizes are large enough so that at least a fraction of the bubbles rise through the entire height of the reaction zone 10, while mitigating against the reaction zone feed material 22 "bubbling through" the reaction zone 10 and being released without being absorbed by the phototrophic biomass. To promote the realization of an optimal bubble size, in some embodiments, the pressure of the reaction zone feed material 22 is controlled using a pressure regulator upstream of the sparger 40.

With respect to those embodiments where the reaction zone 10 is disposed in a photobioreactor 12, in some of these embodiments, for example, the sparger 40 is disposed externally of the photobioreactor 12. In other embodiments, for example, the sparger 40 is disposed within the photobioreactor 12. In some of these embodiments, for example, the sparger 40 extends from a lower portion of the photobioreactor 12 (and within the photobioreactor 12).

In one aspect, carbon dioxide is supplied to the reaction zone 10, and the supplied carbon dioxide defines the reaction zone carbon dioxide supply 2402. The reaction zone carbon dioxide supply 2402 is supplied to the reaction zone 10 at a pressure which effects flow of the reaction zone carbon dioxide supply through a vertical extent of the reaction zone of at least seventy (70) inches. In some embodiments, for example, the vertical extent is at least 10 feet. In some embodiments, for example, the vertical extent is at least 20 feet. In some embodiments, for example, the vertical extent is at least 30 feet. In some embodiments, for example, the pressure of the reaction zone carbon dioxide supply 2402 is increased before being supplied to the reaction zone 10. In some embodiments, the increase in pressure of the reaction zone carbon dioxide supply 2402 is effected while the gaseous exhaust material 18 is being produced by the gaseous exhaust material producing process 20. In some embodiments, for example the increase in pressure of the reaction zone carbon dioxide supply 2402 is effected while the reaction zone carbon dioxide supply is being supplied to the reaction zone 10. In some embodiments, for example, the exposing of the phototrophic biomass disposed in the reaction zone 10 to photosynthetically active light radiation is effected while the reaction zone carbon dioxide supply 2402 is being supplied to the reaction zone 10.

Figure 3:
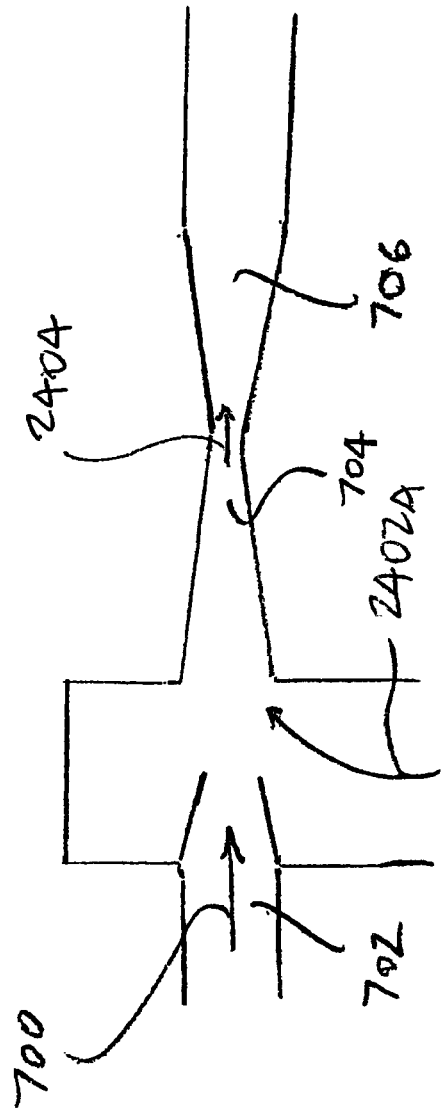
FIG. 3 is a schematic illustration of a portion of a fluid passage of an embodiment of the process.

In some embodiments, for example, the pressure increase is at least partially effected by a prime mover 38. For those embodiments where the pressure increase is at least partially effected by the prime mover 38. An example of a suitable prime mover 38, for embodiments where the reaction zone carbon dioxide supply 2402 is a portion of the reaction zone feed material 22, and the reaction zone feed material 22 includes liquid material, is a pump. Examples of a suitable prime mover 38, for embodiments where the pressure increase is effected to a gaseous flow, include a blower, a compressor, and an air pump. In other embodiments, for example, the pressure increase is effected by a jet pump or eductor.

Where the pressure increase is effected by a jet pump or eductor, in some of these embodiments, for example, the reaction zone carbon dioxide supply 2402 is supplied to the jet pump or eductor and pressure energy is transferred to the reaction zone carbon dioxide supply from another flowing fluid (the "motive fluid flow") using the venturi effect to effect a pressure increase in the reaction zone carbon dioxide supply. In this respect, in some embodiments, for example, and referring to FIG. 3, a motive fluid flow 700 is provided, wherein material of the motive fluid flow 700 includes a motive fluid pressure $P_{M1}$. In this respect also, a lower pressure reaction zone carbon dioxide supply 2402A is provided including a pressure $P_E$, wherein the lower pressure state carbon dioxide supply 2402A includes the reaction zone carbon dioxide supply 2402. In some embodiments, the lower pressure reaction zone carbon dioxide supply 2402A is defined by the reaction zone carbon dioxide supply 2402. $P_{M1}$ of the motive fluid flow is greater than $P_E$ of the lower pressure state carbon dioxide supply 2402A. Pressure of the motive fluid flow 700 is reduced from $P_{M1}$ to $P_{M2}$, such that $P_{M2}$ is less than $P_E$, by flowing the motive fluid flow 700 from an upstream fluid passage portion 702 to an intermediate downstream fluid passage portion 704. The intermediate downstream fluid passage portion 704 is characterized by a smaller cross-sectional area relative to the upstream fluid passage portion 702. By flowing the motive fluid flow 700 from the upstream fluid passage portion 702 to the intermediate downstream fluid passage portion 704, static pressure energy is converted to kinetic energy. When the pressure of the motive fluid flow 700 has becomes reduced to $P_{M2}$, fluid communication between the motive fluid flow 700 and the lower pressure state carbon dioxide supply 2402A is effected such that the lower pressure state carbon dioxide supply 2402A is induced to mix with the motive fluid flow 700 in the intermediate downstream fluid passage portion 704, in response to the pressure differential between the lower pressure state carbon dioxide supply 2402A and the motive fluid flow 700, to produce a reaction zone carbon dioxide supply-comprising mixture 2404 which includes the reaction zone carbon dioxide supply 2402. At least a fraction of the reaction zone carbon dioxide supply-comprising mixture 2404 is supplied to the reaction zone 10. Pressure of the reaction zone carbon dioxide supply-comprising mixture 2404, which includes the reaction zone carbon dioxide supply 2402, is increased to $P_{M3}$, such that the pressure of the reaction zone carbon dioxide supply 2402 is also increased to $P_{M3}$. $P_{M3}$ is greater than $P_E$ and is also sufficient to effect supply of the reaction zone carbon dioxide supply 2402 to the reaction zone 10 and, upon supply of the reaction zone carbon dioxide supply 2402 to the reaction zone 10, effect flow of the reaction zone carbon dioxide supply 2402 through a vertical extent of the reaction zone 10 of at least seventy (70) inches. In some embodiments, for example, $P_{M3}$ is greater than $P_E$ and is also sufficient to effect supply of the reaction zone carbon dioxide supply 2402 to the reaction zone 10 and, upon supply of the reaction zone carbon dioxide supply 2402 to the reaction zone 10, effect flow of the reaction zone carbon dioxide supply 2402 through a vertical extent of the reaction zone 10 of at least 10 feet. In some embodiments, for example, $P_{M3}$ is greater than $P_E$ and is also sufficient to effect supply of the reaction zone carbon dioxide supply 2402 to the reaction zone 10 and, upon supply of the reaction zone carbon dioxide supply 2402 to the reaction zone 10, effect flow of the reaction zone carbon dioxide supply 2402 through a vertical extent of the reaction zone 10 of at least 20 feet. In some embodiments, for example, $P_{M3}$ is greater than $P_E$ and is also sufficient to effect supply of the reaction zone carbon dioxide supply 2402 to the reaction zone 10 and, upon supply of the reaction zone carbon dioxide supply 2402 to the reaction zone 10, effect flow of the reaction zone carbon dioxide supply 2402 through a vertical extent of the reaction zone 10 of at least 30 feet. In any of these embodiments, the pressure increase is designed to overcome the fluid head within the reaction zone 10. The pressure increase is effected by flowing the reaction zone carbon dioxide supply-comprising mixture 2404 from the intermediate downstream fluid passage portion 704 to a "kinetic energy to static pressure energy conversion" downstream fluid passage portion 706. The cross-sectional area of the "kinetic energy to static pressure energy conversion" downstream fluid passage portion 706 is greater than the cross-sectional area of the intermediate downstream fluid passage portion 704, such that kinetic energy of the reaction zone carbon dioxide supply-comprising mixture 2404 disposed in the intermediate downstream fluid passage portion 704 is converted into static pressure energy when the reaction zone carbon dioxide supply-comprising mixture 2404 becomes disposed in the "kinetic energy to static pressure energy conversion" downstream fluid passage portion 706 by virtue of the fact that the reaction zone carbon dioxide supply-comprising mixture 2404 has become flowed to a fluid passage portion with a larger cross-sectional area. In some embodiments, for example, a converging nozzle portion of a fluid passage defines the upstream fluid passage portion 702 and a diverging nozzle portion of the fluid passage defines the "kinetic energy to static pressure energy conversion" downstream fluid passage portion 706, and the intermediate downstream fluid passage portion 704 is disposed intermediate of the converging and diverging nozzle portions. In some embodiments, for example, the combination of the upstream fluid passage portion 702 and the "kinetic energy to static pressure energy conversion" downstream fluid passage portion 706 is defined by a venture nozzle. In some embodiments, for example, the combination of the upstream fluid passage portion 702 and the "kinetic energy to static pressure energy conversion" downstream fluid passage portion 706 is disposed within an eductor or jet pump. In some of these embodiments, for example, the motive fluid flow 700 includes liquid aqueous material and, in this respect, the reaction zone carbon dioxide supply-comprising mixture 2404 includes a combination of liquid and gaseous material. In this respect, in some embodiments, for example, the reaction zone carbon dioxide supply-comprising mixture 2404 includes a dispersion of a gaseous material within a liquid material, wherein the dispersion of a gaseous material includes the reaction zone carbon dioxide supply. Alternatively, in some of these embodiments, for example, the motive fluid flow 700 is another gaseous flow, such as an air flow, and the reaction zone carbon dioxide supply-comprising mixture is gaseous. At least a fraction of the reaction zone carbon dioxide supply-comprising mixture 2404 is supplied to the reaction zone feed material 22 so as to effect supply of the at least a fraction of the reaction zone carbon dioxide supply-comprising mixture to the reaction zone 10. In this respect, the carbon dioxide of the reaction zone feed material 22 includes at least a fraction of the reaction zone carbon dioxide supply 2402. In some embodiments, for example, the carbon dioxide of the reaction zone feed material 22 is defined by at least a fraction of the reaction zone carbon dioxide supply 2402.

In some of these embodiments, for example, the reaction zone carbon dioxide supply 2402 is supplied by at least a fraction of the gaseous exhaust material 18 being discharged by the gaseous exhaust material producing process 20, and the supplying of the reaction zone carbon dioxide supply 2402, by the at least a fraction of the gaseous exhaust material 18 being discharged by the gaseous exhaust material producing process 20, is effected while the gaseous exhaust material 18 is being discharged by the gaseous exhaust material producing process 20 and while the reaction zone carbon dioxide supply 2402 is being supplied to the reaction zone 10. In this respect, in some embodiments, for example, the reaction zone carbon dioxide supply 2402 is supplied by at least a fraction of the carbon dioxide being discharged by the gaseous exhaust material producing process 20, and the supplying of the reaction zone carbon dioxide supply 2402, by the at least a fraction of the carbon dioxide being discharged by the gaseous exhaust material producing process 20, is effected while the carbon dioxide is being discharged by the gaseous exhaust material producing process 20 and while the reaction zone carbon dioxide supply 2402 is being supplied to the reaction zone 10. In some embodiments, for example, the reaction zone carbon dioxide supply 2402 is defined by the discharged carbon dioxide reaction zone supply.

In some embodiments, for example, the photobioreactor 12, or plurality of photobioreactors 12, are configured so as to optimize carbon dioxide absorption by the phototrophic biomass and reduce energy requirements. In this respect, the photobioreactor (s) is (are) configured to provide increased residence time of the carbon dioxide within the reaction zone 10. As well, movement of the carbon dioxide over horizontal distances is minimized, so as to reduce energy consumption. To this end, the one or more photobioreactors 12 is, or are, relatively taller, and provide a reduced footprint, so as to increase carbon dioxide residence time while conserving energy.

In some embodiments, for example, a supplemental nutrient supply 42 is supplied to the reaction zone 10. In some of these embodiments, for example, the exposing of the phototrophic biomass disposed in the reaction zone 10 to photosynthetically active light radiation is effected while the supplemental nutrient supply 42 is being supplied to the reaction zone 10. In some embodiments, for example, the supplemental nutrient supply 42 is effected by a pump, such as a dosing pump. In other embodiments, for example, the supplemental nutrient supply 42 is supplied manually to the reaction zone 10. Nutrients within the reaction zone 10 are processed or consumed by the phototrophic biomass, and it is desirable, in some circumstances, to replenish the processed or consumed nutrients. A suitable nutrient composition is "Bold's Basal Medium", and this is described in Bold, H. C. 1949, *The morphology of Chlamydomonas chlamydogama sp. nov. Bull. Torrey Bot. Club.* 76: 101-8 (see also Bischoff, H. W. and Bold, H. C. 1963, *Phycological Studies IV. Some soil algae from Enchanted Rock and related algal species*, Univ. Texas Publ. 6318: 1-95, and Stein, J. (ED.) *Handbook of Phycological Methods, Culture methods and growth measurements*, Cambridge University Press, pp. 7-24). The supplemental nutrient supply 42 is supplied for supplementing the nutrients provided within the reaction zone, such as "Bold's Basal Medium", or one ore more dissolved components thereof. In this respect, in some embodiments, for example, the supplemental nutrient supply 42 includes "Bold's Basal Medium". In some embodiments for example, the supplemental nutrient supply 42 includes one or more dissolved components of "Bold's Basal Medium", such as $NaNO_3$, $CaCl_2$, $MgSO_4$, $KH_2PO_4$, NaCl, or other ones of its constituent dissolved components.

In some of these embodiments, the rate of supply of the supplemental nutrient supply 42 to the reaction zone 10 is controlled to align with a desired rate of growth of the phototrophic biomass in the reaction zone 10. In some embodiments, for example, regulation of nutrient addition is monitored by measuring any combination of pH, $NO_3$ concentration, and conductivity in the reaction zone 10.

In some embodiments, for example, the supplemental aqueous material supply 44 is supplied to the reaction zone 10 so as to replenish water within the reaction zone 10 of the photobioreactor 12. In some embodiments, for example, and as further described below, the supply of the supplemental aqueous material supply 24 effects the discharge of product from the photobioreactor 12. For example, the supplemental aqueous material supply 44 effects the discharge of product from the photobioreactor 12 as an overflow.

In some embodiments, for example, the supplemental aqueous material is water.

In another aspect, the supplemental aqueous material supply 44 includes at least one of: (a) aqueous material 70 that has been condensed from the reaction zone feed material 22 while the reaction zone feed material 22 is cooled before being supplied to the reaction zone 10, and (b) aqueous material that has been separated from a discharged phototrophic biomass-comprising product 500. In some embodiments, for example, the supplemental aqueous material supply 44 is derived from an independent source (ie. a source other than the process), such as a municipal water supply.

In some embodiments, for example, the supplemental aqueous material supply 44 is supplied by the pump 281. In some of these embodiments, for example, the supplemental aqueous material supply 44 is continuously supplied to the reaction zone 10.

In some embodiments, for example, at least a fraction of the supplemental aqueous material supply 44 is supplied from a container 28, which is further described below. At least a fraction of aqueous material which is discharged from the process is recovered and supplied to the container 28 to provide supplemental aqueous material in the container 28.

Figure 2:
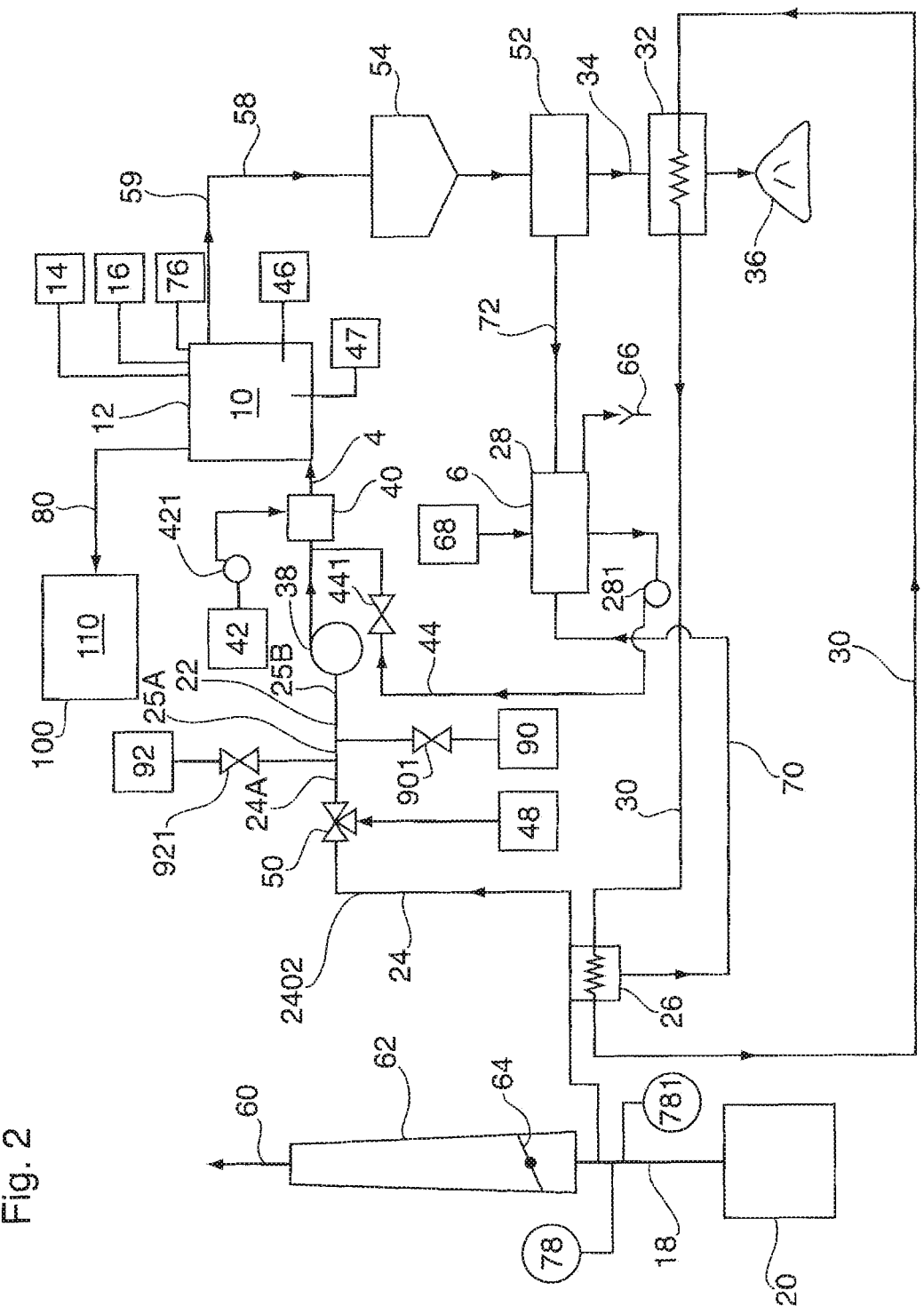
FIG. 2 is a process flow diagram of another embodiment of the process.

Referring to FIG. 2, in some embodiments, the supplemental nutrient supply 42 and the supplemental aqueous material supply 44 are supplied to the reaction zone feed material 22 through the sparger 40 before being supplied to the reaction zone 10. In those embodiments where the reaction zone 10 is disposed in the photobioreactor 12, in some of these embodiments, for example, the sparger 40 is disposed externally of the photobioreactor 12. In some embodiments, it is desirable to mix the reaction zone feed material 22 with the supplemental nutrient supply 42 and the supplemental aqueous material supply 44 within the sparger 40, as this effects better mixing of these components versus separate supplies of the reaction zone feed material 22, the supplemental nutrient supply 42, and the supplemental aqueous material supply 44. On the other hand, the rate of supply of the reaction zone feed material 22 to the reaction zone 10 is limited by virtue of saturation limits of gaseous material of the reaction zone feed material 22 in the combined mixture. Because of this trade-off, such embodiments are more suitable when response time required for providing a modulated supply of carbon dioxide to the reaction zone 10 is not relatively immediate, and this depends on the biological requirements of the phototrophic organisms being used.

In another aspect, at least a fraction of the supplemental nutrient supply 42 is mixed with the supplemental aqueous material in the container 28 to provide a nutrient-enriched supplemental aqueous material supply 44, and the nutrient-enriched supplemental aqueous material supply 44 is supplied directly to the reaction zone 10 or is mixed with the reaction zone feed material 22 in the sparger 40. In some embodiments, for example, the direct or indirect supply of the nutrient-enriched supplemental aqueous material supply is effected by a pump.

In another aspect, while carbon dioxide is being discharged by the gaseous exhaust material producing process 20, and while at least a fraction of the discharged carbon dioxide is being supplied to the reaction zone 10, wherein the at least a fraction of the discharged carbon dioxide which is being supplied to the reaction zone 10 defines a discharged carbon dioxide reaction zone supply, at least one material input to the reaction zone 10 is modulated based on at least the rate (the molar rate and/or the volumetric rate) at which the discharged carbon dioxide reaction zone supply is being supplied to the reaction zone 10. In some of these embodiments, the exposing of the phototrophic biomass disposed in the reaction zone 10 to photosynthetically active light radiation is effected while the modulating of at least one input is being effected.

As suggested above, modulating of a material input is any one of initiating, terminating, increasing, decreasing, or otherwise changing the material input. A material input to the reaction zone 10 is an input whose supply to the reaction zone 10 is material to the rate of growth of the phototrophic biomass within the reaction zone 10. Exemplary material inputs to the reaction zone 10 include supply of photosynthetically active light radiation of a characteristic intensity being to the reaction zone, and supply of supplemental nutrient supply 42 to the reaction zone 10.

In this respect, modulating the intensity of photosynthetically active light radiation being supplied to the reaction zone 10 is any one of: initiating supply of photosynthetically active light radiation to the reaction zone, terminating supply of photosynthetically active light radiation which is being supplied to the reaction zone, increasing the intensity of photosynthetically active light radiation being supplied to the reaction zone, and decreasing the intensity of photosynthetically active light radiation being supplied to the reaction zone 10. In some embodiments, for example, the modulating of the intensity of photosynthetically active light radiation being supplied to the reaction zone includes modulating of the intensity of photosynthetically active light radiation to which at least a fraction of the carbon dioxide-enriched phototrophic biomass is exposed.

Modulating the rate of supply (the molar rate of supply and/or the volumetric rate of supply) of supplemental nutrient supply 42 to the reaction zone is any one of initiating the supply of supplemental nutrient supply 42 to the reaction zone, terminating the supply of supplemental nutrient supply 42 being supplied to the reaction zone, increasing the rate of supply (the molar rate of supply and/or the volumetric rate of supply) of supplemental nutrient supply 42 being supplied to the reaction zone, or decreasing the rate of supply (the molar rate of supply and/or the volumetric rate of supply) of supplemental nutrient supply 42 being supplied to the reaction zone.

In some embodiments, for example, the modulation is based on, at least, an indication of the rate (the molar rate and/or the volumetric rate) at which the discharged carbon dioxide reaction zone supply is being supplied to the reaction zone 10. In this respect, in some embodiments, for example, while carbon dioxide is being discharged by the gaseous exhaust material producing process 20, and while at least a fraction of the discharged carbon dioxide is being supplied to the reaction zone 10, wherein the at least a fraction of the discharged carbon dioxide which is being supplied to the reaction zone 10 defines a discharged carbon dioxide reaction zone supply, at least one material input to the reaction zone 10 is modulated based on, at least, an indication of the rate (molar rate and/or volumetric rate) at which the discharged carbon dioxide reaction zone supply is being supplied to the reaction zone 10. In some of these embodiments, the exposing of the phototrophic biomass disposed in the reaction zone 10 to photosynthetically active light radiation is effected while the modulating of at least one input is being effected.

In some embodiments, for example, the indication of the rate of supply of the discharged carbon dioxide reaction zone supply which is being supplied to the reaction zone 10 is the rate (molar rate and/or volumetric rate) at which gaseous exhaust material 18 is being discharged by the gaseous exhaust material producing process 20, such that the modulation is based on, at least, the rate (molar rate and/or volumetric rate) at which the gaseous exhaust material 18 is being discharged by the gaseous exhaust material producing process 20, wherein the gaseous exhaust material includes the discharged carbon dioxide reaction zone supply. In this respect, in some embodiments, for example, a flow sensor 78 is provided for detecting the flow rate of the gaseous exhaust material 18 being discharged by the gaseous exhaust material producing process 20, and transmitting a signal representative of the detected flow rate of the gaseous exhaust material 18 being discharged by the gaseous exhaust material producing process 20 to the controller. Where molar flow rate is being detected, a gas analyzer operates integrally with the flow sensor 78. Upon the controller receiving a signal from the flow sensor 78 which is representative of the detected flow rate of the gaseous exhaust material 18, the controller effects modulation of at least one material input to the reaction zone 10 based on the detected flow rate of the gaseous exhaust material 18 being discharged by the gaseous exhaust material producing process 20. In some embodiments, for example, the modulating of at least one material input includes at least one of: (i) initiating supply of the photosynthetically active light radiation to the reaction zone 10, or (ii) effecting an increase in the intensity of the photosynthetically active light radiation being supplied to the reaction zone 10. In some embodiments, for example, the modulating of at least one material input includes: (i) initiating supply of the supplemental nutrient supply 42 to the reaction zone, or (ii) effecting an increase in the rate of supply (molar rate of supply and/or volumetric rate of supply) of the supplemental nutrient supply 42 being supplied to the reaction zone 10. In some embodiments, the modulation of at least one material input includes at least one of: (i) terminating supply of the photosynthetically active light radiation being supplied to the reaction zone 10, or (ii) effecting a decrease in the intensity of the photosynthetically active light radiation being supplied to the reaction zone 10. In some embodiments, for example, the modulating of at least one material input includes at least one of: (i) terminating supply of the supplemental nutrient supply 42 being supplied to the reaction zone, or (ii) effecting a decrease in the rate of supply (molar rate of supply and/or the volumetric rate) of the supplemental nutrient supply 42 being supplied to the reaction zone 10.

In some embodiments, for example, the indication of the rate of supply of the discharged carbon dioxide reaction zone supply which is being supplied to the reaction zone 10 is the concentration of carbon dioxide of the gaseous exhaust material 18 being discharged by the gaseous exhaust material producing process 20, such that the modulation is based on, at least, the concentration of carbon dioxide of the gaseous exhaust material 18 being discharged by the gaseous exhaust material producing process 20, wherein the gaseous exhaust material 18 includes the discharged carbon dioxide reaction zone supply. In this respect, in some embodiments, for example, a carbon dioxide sensor 781 is provided for detecting the concentration of carbon dioxide of the gaseous exhaust material 18 being discharged by the gaseous exhaust material producing process 20, and transmitting a signal representative of the concentration of carbon dioxide of the gaseous exhaust material 18 being discharged by the gaseous exhaust material producing process 20 to the controller. In some embodiments, the carbon dioxide sensor is a gas analyzer such that the concentration detected is a molar concentration. Upon the controller receiving a signal from the carbon dioxide sensor 781 which is representative of a detected concentration of carbon dioxide of the gaseous exhaust material 18, the controller effects modulation of at least one material input to the reaction zone 10 based on the detected concentration of carbon dioxide of the gaseous exhaust material 18. In some embodiments, for example, the modulating of at least one material input includes at least one of: (i) initiating supply of the photosynthetically active light radiation to the reaction zone 10, or (ii) effecting an increase in the intensity of the photosynthetically active light radiation being supplied to the reaction zone 10. In some embodiments, for example, the modulating of at least one material input includes: (i) initiating supply of the supplemental nutrient supply 42 to the reaction zone, or (ii) effecting an increase in the rate of supply (molar rate of supply and/or volumetric rate of supply) of the supplemental nutrient supply 42 being supplied to the reaction zone 10. In some embodiments, the modulation of at least one material input includes at least one of: (i) terminating supply of the photosynthetically active light radiation being supplied to the reaction zone 10, or (ii) effecting a decrease in the intensity of the photosynthetically active light radiation being supplied to the reaction zone 10. In some embodiments, for example, the modulating of at least one material input includes at least one of: (i) terminating supply of the supplemental nutrient supply 42 being supplied to the reaction zone, or (ii) effecting a decrease in the molar rate of supply (molar rate of supply and/or volumetric rate of supply) of the supplemental nutrient supply 42 being supplied to the reaction zone 10.

In some embodiments, for example, the indication of the molar rate of supply of the discharged carbon dioxide reaction zone supply which is being supplied to the reaction zone 10 is the rate (molar rate and/or volumetric rate) at which carbon dioxide is being discharged by the gaseous exhaust material producing process 20, such that the modulation is based on, at least, the rate (molar rate and/or volumetric rate) at which carbon dioxide is being discharged by the gaseous exhaust material producing process 20, wherein the gaseous exhaust material 18 includes the discharged carbon dioxide reaction zone supply. In some embodiments, for example, the rate at which carbon dioxide is being discharged by the gaseous exhaust material producing process 20 is calculated based on the combination of the detected flow rate (molar flow rate and/or volumetric flow rate) of the gaseous exhaust material 18 being discharged by the gaseous exhaust material producing process 20 and the detected concentration of carbon dioxide of the gaseous effluent material 18 being discharged by the gaseous exhaust material producing process 20. The combination of (i) the detected flow rate of the gaseous exhaust material 18 being discharged by the gaseous exhaust material producing process 20, and (ii) the detected molar concentration of carbon dioxide of the gaseous effluent material 18 being discharged by the gaseous exhaust material producing process 20, provides a basis for calculating a rate (molar rate and/or volumetric rate) at which carbon dioxide is being discharged by the gaseous exhaust material producing process 20. In this respect, a flow sensor 78 is provided for detecting the flow rate of the gaseous exhaust material 18 being discharged by the gaseous exhaust material producing process 20, and transmitting a signal representative of the detected flow rate of the gaseous exhaust material 18, being discharged by the gaseous exhaust material producing process 20, to the controller. In this respect also, a carbon dioxide sensor 781 is provided for detecting the concentration of carbon dioxide of the gaseous exhaust material 18 being discharged by the gaseous exhaust material producing process 20, and transmitting a signal representative of the detected concentration of carbon dioxide of the gaseous exhaust material 18, being discharged by the gaseous exhaust material producing process 20, to the controller. In some embodiments, the carbon dioxide sensor is a gas analyzer such that the concentration detected is a molar concentration. Upon the controller receiving a flow sensor signal from the flow sensor 78, which is representative of a detected flow rate of the gaseous exhaust material 18 being discharged by the gaseous exhaust material producing process 20, and also receiving a carbon dioxide sensor signal from a carbon dioxide sensor 781, which is representative of a detected concentration of carbon dioxide of the gaseous exhaust material 18 being discharged by the gaseous exhaust material producing process 20, wherein the detected concentration of carbon dioxide of the gaseous exhaust material 18 is being detected contemporaneously, or substantially contemporaneously, with the detecting of the flow rate of the gaseous exhaust material 18 being discharged by the process 20, upon which the flow sensor signal is based, and calculating a rate (molar rate and/or volumetric rate) of carbon dioxide being discharged by the gaseous exhaust material producing process 20, based upon the received flow sensor signal and the received carbon dioxide sensor signal, the controller effects modulation of at least one material input to the reaction zone 10 based on the calculated rate of carbon dioxide being discharged by the gaseous exhaust material producing process 20. In some embodiments, for example, the modulating of at least one material input includes at least one of: (i) initiating supply of the photosynthetically active light radiation to the reaction zone 10, or (ii) effecting an increase in the intensity of the photosynthetically active light radiation being supplied to the reaction zone 10. In some embodiments, for example, the modulating of at least one material input includes: (i) initiating supply of the supplemental nutrient supply 42 to the reaction zone, or (ii) effecting an increase in the rate of supply (molar rate of supply and/or volumetric rate of supply) of the supplemental nutrient supply 42 being supplied to the reaction zone 10. In some embodiments, the modulation of at least one material input includes at least one of: (i) terminating supply of the photosynthetically active light radiation being supplied to the reaction zone 10, or (ii) effecting a decrease in the intensity of the photosynthetically active light radiation being supplied to the reaction zone 10. In some embodiments, for example, the modulating of at least one material input includes at least one of: (i) terminating supply of the supplemental nutrient supply 42 being supplied to the reaction zone, or (ii) effecting a decrease in the rate of supply (molar rate of supply and/or volumetric rate of supply) of the supplemental nutrient supply 42 being supplied to the reaction zone 10.

In another aspect, while carbon dioxide is being discharged by the gaseous exhaust material producing process 20, and while at least a fraction of the discharged carbon dioxide is being supplied to the reaction zone 10, wherein the at least a fraction of the discharged carbon dioxide which is being supplied to the reaction zone 10 defines a discharged carbon dioxide reaction zone supply, when a change in the rate of supply (molar rate of supply and/or volumetric rate of supply) of the discharged carbon dioxide reaction zone supply being supplied to the reaction zone 10 is detected, modulation of at least one material input to the reaction zone 10 is effected. In this respect, the modulation of at least one material input to the reaction zone 10 is effected in response to the detection of a change in the rate of supply (molar rate of supply and/or volumetric rate of supply) of the discharged carbon dioxide reaction zone supply being supplied to the reaction zone 10. In some of these embodiments, the exposing of the phototrophic biomass disposed in the reaction zone 10 to photosynthetically active light radiation is effected while the modulating of at least one material input is being effected.

In another aspect, while carbon dioxide is being discharged by the gaseous exhaust material producing process 20, and while at least a fraction of the discharged carbon dioxide is being supplied to the reaction zone 10, wherein the at least a fraction of the discharged carbon dioxide which is being supplied to the reaction zone 10 defines a discharged carbon dioxide reaction zone supply, when an indication of a change in the rate of supply (molar rate of supply and/or volumetric rate of supply) of the discharged carbon dioxide reaction zone supply being supplied to the reaction zone 10 is detected, modulation of at least one material input to the reaction zone 10 is effected. In this respect, the modulation of at least one material input to the reaction zone 10 is effected in response to the detection of an indication of a change in the rate of supply (molar rate of supply and/or volumetric rate of supply) of the discharged carbon dioxide reaction zone supply being supplied to the reaction zone 10. In some of these embodiments, the exposing of the phototrophic biomass disposed in the reaction zone 10 to photosynthetically active light radiation is effected while the modulating of at least one material input is being effected.

As above-described, modulating of a material input is any one of initiating, terminating, increasing, or decreasing the material input. Exemplary material inputs to the reaction zone include supply of photosynthetically active light radiation of a characteristic intensity to the reaction zone 10, and supply of supplemental nutrient supply 42 to the reaction zone 10.

As also above-described, modulating the intensity of photosynthetically active light radiation being supplied to the reaction zone 10 is any one of: initiating supply of photosynthetically active light radiation to the reaction zone, terminating supply of photosynthetically active light radiation being supplied to the reaction zone, increasing the intensity of photosynthetically active light radiation being supplied to the reaction zone, and decreasing the intensity of photosynthetically active light radiation being supplied to the reaction zone. In some embodiments, for example, the modulating of the intensity of photosynthetically active light radiation being supplied to the reaction zone includes modulating of the intensity of photosynthetically active light radiation to which at least a fraction of the carbon dioxide-enriched phototrophic biomass is exposed.

As also above-described, modulating the rate of supply (molar rate of supply and/or volumetric rate of supply) of supplemental nutrient supply 42 to the reaction zone is any one of initiating the supply of supplemental nutrient supply 42 to the reaction zone, terminating the supply of supplemental nutrient supply 42 being supplied to the reaction zone, increasing the rate of supply (molar rate of supply and/or volumetric rate of supply) of supplemental nutrient supply 42 being supplied to the reaction zone, or decreasing the rate of supply (molar rate of supply and/or volumetric rate of supply) of supplemental nutrient supply 42 being supplied to the reaction zone.

In some embodiments, for example, and as also above-described, the modulating of the intensity of the photosynthetically active light radiation is effected by a controller. In some embodiments, for example, to increase or decrease light intensity of a light source, the controller changes the power output to the light source from the power supply, and this can be effected by controlling either one of voltage or current. As well, in some embodiments, for example, the modulating of the rate of supply of the supplemental nutrient supply 42 is also effected by a controller. To modulate the rate of supply of the supplemental nutrient supply 42, the controller can control a dosing pump 421 to provide a predetermined flow rate of the supplemental nutrient supply 42.

In some embodiments, for example, while carbon dioxide is being discharged by the gaseous exhaust material producing process 20, and while at least a fraction of the discharged carbon dioxide is being supplied to the reaction zone 10, wherein the at least a fraction of the discharged carbon dioxide which is being supplied to the reaction zone 10 defines a discharged carbon dioxide reaction zone supply, when an increase in the rate of supply (molar rate of supply and/or volumetric rate of supply) of the discharged carbon dioxide reaction zone supply being supplied to the reaction zone 10 is detected, the modulating of at least one material input includes at least one of: (i) initiating supply of the photosynthetically active light radiation to the reaction zone 10, or (ii) effecting an increase in the intensity of the photosynthetically active light radiation being supplied to the reaction zone 10. In this respect, such modulation is effected in response to the detection of an increase in the rate of supply (molar rate of supply and/or volumetric rate of supply) of the discharged carbon dioxide reaction zone supply being supplied to the reaction zone 10. In some embodiments, for example, the increase in the intensity of the photosynthetically active light radiation being supplied to the reaction zone 10 is proportional to the increase in the molar rate of supply of the discharged carbon dioxide reaction zone supplied being supplied to the reaction zone 10.

In some embodiments, for example, while carbon dioxide is being discharged by the gaseous exhaust material producing process 20, and while at least a fraction of the discharged carbon dioxide is being supplied to the reaction zone 10, wherein the at least a fraction of the discharged carbon dioxide which is being supplied to the reaction zone 10 defines a discharged carbon dioxide reaction zone supply, when an indication of an increase in the rate of supply (molar rate of supply and/or volumetric rate of supply) of the discharged carbon dioxide reaction zone supply being supplied to the reaction zone 10 is detected, the modulating of at least one material input includes at least one of: (i) initiating supply of the photosynthetically active light radiation to the reaction zone 10, or (ii) effecting an increase in the intensity of the photosynthetically active light radiation being supplied to the reaction zone 10. In this respect, such modulation is effected in response to the detection of an indication of an increase in the rate of supply (molar rate of supply and/or volumetric rate of supply) of the discharged carbon dioxide reaction zone supply being supplied to the reaction zone 10. In some embodiments, for example, the increase in the intensity of the photosynthetically active light radiation being supplied to the reaction zone 10 is proportional to the increase in the rate of supply (molar rate of supply and/or volumetric rate of supply) of the discharged carbon dioxide reaction zone supplied being supplied to the reaction zone 10.

In some embodiments, for example, upon the initiating of the supply of photosynthetically active light radiation being supplied to the reaction zone, or the increasing of the intensity of photosynthetically active light radiation being supplied to the reaction zone, the rate of cooling of a light source, that is provided in the reaction zone 10 and that is supplying the photosynthetically active light radiation to the reaction zone, is increased. The cooling is effected for mitigating heating of the reaction zone by any thermal energy that is dissipated from the light source while the light source is supplying the photosynthetically active light radiation to the reaction zone. Heating of the reaction zone 10 increases the temperature of the reaction zone. In some embodiments, excessive temperature within the reaction zone 10 is deleterious to the phototrophic biomass. In some embodiments, for example, the light source is disposed in a liquid light guide and a heat transfer fluid is disposed within the liquid light guide, and the rate of cooling is increased by increasing the rate of exchanges of the heat transfer fluid within the liquid light guide.

In some embodiments, for example, while carbon dioxide is being discharged by the gaseous exhaust material producing process 20, and while at least a fraction of the discharged carbon dioxide is being supplied to the reaction zone 10, wherein the at least a fraction of the discharged carbon dioxide which is being supplied to the reaction zone 10 defines a discharged carbon dioxide reaction zone supply, when an increase in the rate of supply (molar rate of supply and/or volumetric rate of supply) of the discharged carbon dioxide reaction zone supply being supplied to the reaction zone 10 is detected, the modulating of at least one material input includes at least one of: (i) initiating supply of the supplemental nutrient supply 42 to the reaction zone 10, or (ii) effecting an increase in the rate of supply (molar rate of supply and/or volumetric rate of supply) of the supplemental nutrient supply 42 being supplied to the reaction zone 10. In this respect, such modulation is effected in response to the detection of an increase in the rate of supply (molar rate of supply and/or volumetric rate of supply) of the discharged carbon dioxide reaction zone supply being supplied to the reaction zone 10.

In some embodiments, for example, while carbon dioxide is being discharged by the gaseous exhaust material producing process 20, and while at least a fraction of the discharged carbon dioxide is being supplied to the reaction zone 10, wherein the at least a fraction of the discharged carbon dioxide which is being supplied to the reaction zone 10 defines a discharged carbon dioxide reaction zone supply, when an indication of an increase in the rate of supply (molar rate of supply and/or volumetric rate of supply) of the discharged carbon dioxide reaction zone supply being supplied to the reaction zone 10 is detected, the modulating of at least one material input includes at least one of: (i) initiating supply of the supplemental nutrient supply 42 to the reaction zone 10, or (ii) effecting an increase in the rate of supply (molar rate of supply and/or volumetric rate of supply) of the supplemental nutrient supply 42 being supplied to the reaction zone 10. In this respect, such modulation is effected in response to the detection of an indication of an increase in the rate of supply (molar rate of supply and/or volumetric rate of supply) of the discharged carbon dioxide reaction zone supply being supplied to the reaction zone 10.

In some embodiments, for example, the indication of an increase in the rate of supply (molar rate of supply and/or volumetric rate of supply) of the discharged carbon dioxide reaction zone supply being supplied to the reaction zone 10 which is detected is an increase in the rate (molar rate and/or volumetric rate) at which gaseous exhaust material 18 is being discharged by the gaseous exhaust material producing process 20, wherein the gaseous exhaust material 18 includes the discharged carbon dioxide reaction zone supply. In this respect, in some embodiments, for example, a flow sensor 78 is provided for detecting the flow rate of the gaseous exhaust material 18 being discharged by the gaseous exhaust material producing process 20 (in the case of molar flow rate, a gas analyzer is also incorporated) and transmitting a signal representative of the detected molar flow rate of the gaseous exhaust material 18 to the controller. Upon the controller comparing a received signal from the flow sensor 78, which is representative of the detected flow rate of the gaseous exhaust material 18 being discharged by the gaseous exhaust material producing process 20, to a previously received signal representative of a previously detected flow rate of the gaseous exhaust material 18 being discharged by the gaseous exhaust material producing process 20, and determining that an increase in the flow rate of the gaseous exhaust material 18 being discharged by the gaseous exhaust material producing process 20 has been effected, the controller effects at least one of: (a) initiation of supply of photosynthetically active light radiation to the reaction zone 10, or an increase in the intensity of photosynthetically active light radiation supply being supplied to the reaction zone 10, and (b) initiation of supply of a supplemental nutrient supply 42 to the reaction zone 10, or an increase in the rate of supply (molar rate of supply and/or volumetric rate of supply) of a supplemental nutrient supply 42 being supplied to the reaction zone 10.

In some embodiments, for example, the indication of an increase in the molar rate of supply of the discharged carbon dioxide reaction zone supply being supplied to the reaction zone 10 which is detected is an increase in the concentration of carbon dioxide of gaseous exhaust material 18 being discharged by the gaseous exhaust material producing process 20, wherein the gaseous exhaust material 18 includes the discharged carbon dioxide reaction zone supply. In this respect, in some embodiments, for example, a carbon dioxide sensor 781 is provided for detecting the concentration of carbon dioxide of the gaseous exhaust material 18 being discharged by the gaseous exhaust material producing process 20, and transmitting a signal representative of the detected concentration of carbon dioxide of the gaseous exhaust material producing process 20, to the controller. In some embodiments, the carbon dioxide sensor is a gas analyzer such that the concentration detected is a molar concentration. Upon the controller comparing a received signal from the carbon dioxide sensor 781, which is representative of the detected concentration of carbon dioxide of the gaseous exhaust material 18 being discharged by the gaseous exhaust material producing process 20, to a previously received signal representative of a previously detected concentration of carbon dioxide of the gaseous exhaust material 18 being discharged by the gaseous exhaust material producing process 20, and determining that an increase in the concentration of carbon dioxide of the gaseous exhaust material 18 has been effected, the controller effects at least one of: (a) initiation of supply of photosynthetically active light radiation to the reaction zone 10, or an increase in the intensity of photosynthetically active light radiation supply being supplied to the reaction zone 10, and (b) initiation of supply of a supplemental nutrient supply 42 to the reaction zone 10, or an increase in the rate of supply (molar rate of supply and/or volumetric rate of supply) of a supplemental nutrient supply 42 being supplied to the reaction zone 10.

In some embodiments, for example, the indication of an increase in the rate of supply (molar rate of supply and/or volumetric rate of supply) of the discharged carbon dioxide reaction zone supply being supplied to the reaction zone 10 is an increase in the rate at which carbon dioxide (molar rate of supply and/or volumetric rate of supply) is being discharged by the gaseous exhaust material producing process 20. In this respect, in some embodiments, for example, the increase in the rate at which carbon dioxide is being discharged by the gaseous exhaust material producing process 20 is based on a comparison between (i) a calculated rate at which carbon dioxide is being discharged by the gaseous exhaust producing process 20, wherein the calculation is based on the combination of a detected flow rate of the gaseous exhaust material 18 being discharged by the gaseous exhaust material producing process 20 and also a detected concentration of carbon dioxide of the gaseous exhaust material 18 being discharged by the gaseous exhaust material producing process 20, and (ii) a calculated rate at which carbon dioxide has been previously discharged by the gaseous exhaust producing process 20, wherein the calculation is based on the combination of a previously detected flow rate of the gaseous exhaust material 18 previously being discharged by the gaseous exhaust material producing process 20 and also a previously detected concentration of carbon dioxide of the gaseous exhaust material 18 previously being discharged by the gaseous exhaust material producing process 20. In this respect, a flow sensor 78 is provided for detecting the flow rate of the gaseous exhaust material 18 being discharged by the gaseous exhaust material producing process 20, and transmitting a signal representative of the detected flow rate of the gaseous exhaust material 18 being discharged by the gaseous exhaust material producing process 20, to the controller. In this respect also, a carbon dioxide sensor 781 is provided for detecting the concentration of carbon dioxide of the gaseous exhaust material 18 being discharged by the gaseous exhaust material producing process 20, and transmitting a signal representative of the detected concentration of carbon dioxide of the gaseous exhaust material 18, being discharged by the gaseous exhaust material producing process 20, to the controller. In some embodiments, the carbon dioxide sensor is a gas analyzer such that the concentration detected is a molar concentration. Upon the controller receiving a flow sensor signal from the flow sensor 78, which is representative of a detected flow rate of the gaseous exhaust material 18 being discharged by the gaseous exhaust material producing process 20, and also receiving a carbon dioxide sensor signal from a carbon dioxide sensor 781, which is representative of a detected concentration of carbon dioxide of the gaseous exhaust material 18 being discharged by the gaseous exhaust material producing process 20, wherein the detecting of the detected concentration of carbon dioxide of the gaseous exhaust material 18 is contemporaneous, or substantially contemporaneous, with the detecting of the detected flow rate of the gaseous exhaust material 18 being discharged by the process 20, upon which the flow sensor signal is based, and calculating a rate (molar rate and/or volumetric rate) at which carbon dioxide is being discharged by the gaseous exhaust material producing process 20, based upon the received flow sensor signal and the received carbon dioxide sensor signal, and comparing the calculated rate at which carbon dioxide is being discharged by the gaseous exhaust material producing process 20 to a calculated rate at which carbon dioxide has previously been discharged by the gaseous exhaust material producing process 20, wherein the calculated rate at which carbon dioxide has previously been discharged by the gaseous exhaust material producing process 20 is based upon the combination of a previously received flow sensor signal, which is representative of a previously detected flow rate of the gaseous exhaust material 18 previously discharged by the gaseous exhaust material producing process 20, and a previously received carbon dioxide sensor signal, which is representative of a previously detected concentration of carbon dioxide of the gaseous exhaust material 18 previously discharged by the gaseous exhaust material producing process 20, wherein the detecting of the previously detected concentration of carbon dioxide has been effected contemporaneously, or substantially contemporaneously, with the detecting of the previously detected flow rate of the previously discharging gaseous exhaust material 18, upon which the previously received flow sensor signal is based, and determining that an increase in the rate at which carbon dioxide is being discharged by the gaseous exhaust material producing process 20 has been effected, the controller effects at least one of: (a) initiation of supply of photosynthetically active light radiation to the reaction zone 10, or an increase in the intensity of photosynthetically active light radiation supply being supplied to the reaction zone 10, and (b) initiation of supply of a supplemental nutrient supply 42 to the reaction zone 10, or an increase in the rate of supply (molar rate of supply and/or volumetric rate of supply) of a supplemental nutrient supply 42 being supplied to the reaction zone 10.

In some embodiments, for example, any one of: (a) an increase in the detected flow rate of the gaseous exhaust material 18 being discharged by the gaseous exhaust material producing process 20, (b) an increase in the detected concentration of carbon dioxide of the gaseous exhaust material 18 being discharged by the gaseous exhaust material producing process 20, or (c) an increase in the calculated rate of supply of carbon dioxide being discharged by the gaseous exhaust material producing process 20, is an indicator of an increase in the rate of supply of the discharged carbon dioxide reaction zone supply being supplied to the reaction zone 10. Where there is provided an increase in the rate of supply of the discharged carbon dioxide reaction zone supply to the reaction zone 10, the rate of supply of at least one condition for growth (ie. increased rate of supply of carbon dioxide) of the phototrophic biomass is increased, and the rates of supply of other inputs, relevant to such growth, are correspondingly initiated or increased, in anticipation of growth of the phototrophic biomass in the reaction zone 10.

In some embodiments, for example, while carbon dioxide is being discharged by the gaseous exhaust material producing process 20, and while at least a fraction of the discharged carbon dioxide is being supplied to the reaction zone 10, wherein the at least a fraction of the discharged carbon dioxide which is being supplied to the reaction zone 10 defines a discharged carbon dioxide reaction zone supply, when a decrease in the rate of supply (molar rate of supply and/or volumetric rate of supply) of the discharged carbon dioxide reaction zone supply being supplied to the reaction zone 10 is detected, the modulating of at least one material input includes effecting at least one of: (i) terminating supply of the photosynthetically active light radiation being supplied to the reaction zone 10, or (ii) effecting a decrease in the intensity of the photosynthetically active light radiation being supplied to the reaction zone 10. In this respect, such modulation is effected in response to the detection of a decrease in the rate of supply (molar rate of supply and/or volumetric rate of supply) of the discharged carbon dioxide reaction zone supply being supplied to the reaction zone 10. In some embodiments, for example, the decrease in the intensity of the photosynthetically active light radiation being supplied to the reaction zone is proportional to the decrease in the rate of supply (molar rate of supply and/or volumetric rate of supply) of the discharged carbon dioxide reaction zone supplied being supplied to the reaction zone 10.

In some embodiments, for example, while carbon dioxide is being discharged by the gaseous exhaust material producing process 20, and while at least a fraction of the discharged carbon dioxide is being supplied to the reaction zone 10, wherein the at least a fraction of the discharged carbon dioxide which is being supplied to the reaction zone 10 defines a discharged carbon dioxide reaction zone supply, when an indication of a decrease in the rate of supply (molar rate of supply and/or volumetric rate of supply) of the discharged carbon dioxide reaction zone supply being supplied to the reaction zone 10 is detected, the modulating of at least one material input includes effecting at least one of: (i) terminating supply of the photosynthetically active light radiation being supplied to the reaction zone 10, or (ii) effecting a decrease in the intensity of the photosynthetically active light radiation being supplied to the reaction zone 10. In this respect, such modulation is effected in response to the detection of an indication of a decrease in the rate of supply (molar rate of supply and/or volumetric rate of supply) of the discharged carbon dioxide reaction zone supply being supplied to the reaction zone 10. In some embodiments, for example, the decrease in the intensity of the photosynthetically active light radiation being supplied to the reaction zone is proportional to the decrease in the rate of supply (molar rate of supply and/or volumetric rate of supply) of the discharged carbon dioxide reaction zone supplied being supplied to the reaction zone 10.

In some embodiments, for example, while carbon dioxide is being discharged by the gaseous exhaust material producing process 20, and while at least a fraction of the discharged carbon dioxide is being supplied to the reaction zone 10, wherein the at least a fraction of the discharged carbon dioxide which is being supplied to the reaction zone 10 defines a discharged carbon dioxide reaction zone supply, when a decrease in the rate of supply (molar rate of supply and/or volumetric rate of supply) of the discharged carbon dioxide reaction zone supply being supplied to the reaction zone 10 is detected, the modulating of at least one material input includes effecting at least one of: (i) terminating supply of the supplemental nutrient supply 42 being supplied to the reaction zone, or (ii) effecting a decrease in the rate of supply (molar rate of supply and/or volumetric rate of supply) of the supplemental nutrient supply 42 being supplied to the reaction zone 10. In this respect, such modulation is effected in response to the detection of a decrease in the rate of supply (molar rate of supply and/or volumetric rate of supply) of the discharged carbon dioxide reaction zone supply being supplied to the reaction zone 10.

In some embodiments, for example, while carbon dioxide is being discharged by the gaseous exhaust material producing process 20, and while at least a fraction of the discharged carbon dioxide is being supplied to the reaction zone 10, wherein the at least a fraction of the discharged carbon dioxide which is being supplied to the reaction zone 10 defines a discharged carbon dioxide reaction zone supply, when an indication of a decrease in the rate of supply (molar rate of supply and/or volumetric rate of supply) of the discharged carbon dioxide reaction zone supply being supplied to the reaction zone 10 is detected, the modulating of at least one material input includes effecting at least one of: (i) terminating supply of the supplemental nutrient supply 42 being supplied to the reaction zone, or (ii) effecting a decrease in the rate of supply (molar rate of supply and/or volumetric rate of supply) of the supplemental nutrient supply 42 being supplied to the reaction zone 10. In this respect, such modulation is effected in response to the detection of an indication of a decrease in the rate of supply (molar rate of supply and/or volumetric rate of supply) of the discharged carbon dioxide reaction zone supply being supplied to the reaction zone 10.

In some embodiments, for example, the indication of a decrease in the molar rate of supply of the discharged carbon dioxide reaction zone supply being supplied to the reaction zone 10 which is detected is a decrease in the rate (molar rate and/or volumetric rate) at which the gaseous exhaust material 18 is being discharged by the gaseous exhaust material producing process 20. In this respect, in some embodiments, for example, a flow sensor 78 is provided for detecting the flow rate of the gaseous exhaust material 18 being discharged by the gaseous exhaust material producing process 20 (for detecting molar flow rate, a gas analyzer is incorporated), and transmitting a signal representative of the detected flow rate of the gaseous exhaust material 18 to the controller. Upon the controller comparing a received signal from the flow sensor 78, which is representative of the detected flow rate of the gaseous exhaust material 18 being discharged by the gaseous exhaust material producing process 20, to a previously received signal representative of a previously detected flow rate of the gaseous exhaust material 18 previously being discharged by the gaseous exhaust material producing process 20, and determining that a decrease in the flow rate of the gaseous exhaust material 18, being discharged by the gaseous exhaust material producing process 20, has been effected, the controller effects at least one of: (a) a decrease in the intensity of, or termination of, supply of the photosynthetically active light radiation being supplied to the reaction zone 10, and (b) a decrease in the rate of supply (molar rate of supply and/or volumetric rate of supply) of, or termination of supply of, of a supplemental nutrient supply 42 being supplied to the reaction zone 10.

In some embodiments, for example, the indication of a decrease in the rate of supply (molar rate of supply and/or volumetric rate of supply) of the discharged carbon dioxide reaction zone supply being supplied to the reaction zone 10 which is detected is a decrease in the concentration of carbon dioxide of the gaseous effluent material 18 being discharged by the gaseous exhaust material producing process 20. In this respect, in some embodiments, for example, a carbon dioxide sensor 781 is provided for detecting the concentration of carbon dioxide of the gaseous exhaust material 18 being discharged by the gaseous exhaust material producing process 20, and transmitting a signal representative of the detected concentration of carbon dioxide of the gaseous exhaust material 18 being discharged by the gaseous exhaust material producing process 20, to the controller. In some embodiments, the carbon dioxide sensor is a gas analyzer such that the concentration detected is a molar concentration. Upon the controller comparing a received signal from the carbon dioxide sensor 781 which is representative of the detected concentration of carbon dioxide of the gaseous exhaust material 18 being discharged by the gaseous exhaust material producing process 20, to a previously received signal representative of a previously detected concentration of carbon dioxide of the gaseous exhaust material 18 previously being discharged by the gaseous exhaust material producing process 20, and determining that a decrease in the concentration of carbon dioxide of the gaseous exhaust material 18, being discharged by the gaseous exhaust material producing process 20, has been effected, the controller effects at least one of: (a) a decrease in the intensity of, or termination of, supply of the photosynthetically active light radiation being supplied to the reaction zone 10, and (b) a decrease in the rate of supply (molar rate of supply and/or volumetric rate of supply) of, or termination of supply of, a supplemental nutrient supply 42 being supplied to the reaction zone 10.

In some embodiments, for example, the indication of a decrease in the rate of supply (molar rate of supply and/or volumetric rate of supply) of the discharged carbon dioxide reaction zone supply being supplied to the reaction zone 10 is a decrease in the rate (molar rate and/or volumetric rate) at which carbon dioxide is being discharged by the gaseous exhaust material producing process 20. In this respect, in some embodiments, for example, the decrease in the rate at which carbon dioxide is being discharged by the gaseous exhaust material producing process 20 is based on a comparison between (i) a calculated rate at which carbon dioxide is being discharged by the gaseous exhaust producing process 20, wherein the calculation is based on the combination of a detected flow rate of the gaseous exhaust material 18 being discharged by the gaseous exhaust material producing process 20 and also a detected concentration of carbon dioxide of the gaseous exhaust material 18 being discharged by the gaseous exhaust material producing process 20, and (ii) a calculated rate at which carbon dioxide has previously been discharged by the gaseous exhaust producing process 20, wherein the calculation is based on the combination of a previously detected flow rate of the gaseous exhaust material 18 previously being discharged by the gaseous exhaust material producing process 20 and also a previously detected concentration of carbon dioxide of the gaseous exhaust material 18 previously being discharged by the gaseous exhaust material producing process 20. In this respect, a flow sensor 78 is provided for detecting the flow rate of the gaseous exhaust material 18 being discharged by the gaseous exhaust material producing process 20, and transmitting a signal representative of the detected flow rate of the gaseous exhaust material 18 being discharged by the gaseous exhaust material producing process 20, to the controller. In this respect also, a carbon dioxide sensor 781 is provided for detecting the concentration of carbon dioxide of the gaseous exhaust material 18 being discharged by the gaseous exhaust material producing process 20, and transmitting a signal representative of the detected concentration of carbon dioxide of the gaseous exhaust material 18 being discharged by the gaseous exhaust material producing process 20, to the controller. In some embodiments, the carbon dioxide sensor is a gas analyzer such that the concentration detected is a molar concentration. Upon the controller receiving a flow sensor signal from the flow sensor 78, which is representative of a detected flow rate of the gaseous exhaust material 18 being discharged by the gaseous exhaust material producing process 20, and also receiving a carbon dioxide sensor signal from a carbon dioxide sensor 781, which is representative of a detected concentration of carbon dioxide of the gaseous exhaust material 18 being discharged by the gaseous exhaust material producing process 20, wherein the detecting of the detected concentration of carbon dioxide of the gaseous exhaust material 18 is contemporaneous, or substantially contemporaneous, with the detecting of the detected flow rate of the gaseous exhaust material 18 being discharged by the process 20, upon which the flow sensor signal is based, and calculating a rate (molar rate and/or volumetric rate) at which carbon dioxide is being discharged by the gaseous exhaust material producing process 20, based upon the received flow sensor signal and the received carbon dioxide sensor signal, and comparing the calculated rate at which carbon dioxide is being discharged by the gaseous exhaust material producing process 20 to a calculated rate at which carbon dioxide has previously been discharged by the gaseous exhaust material producing process 20, wherein the calculation of the rate at which carbon dioxide has previously been discharged by the gaseous exhaust material producing process 20, is based upon the combination of a previously received flow sensor signal, which is representative of a previously detected flow rate of the gaseous exhaust material 18 previously discharged by the gaseous exhaust material producing process 20, and a previously received carbon dioxide sensor signal, which is representative of a previously detected concentration of carbon dioxide of the gaseous exhaust material 18 previously discharged by the gaseous exhaust material producing process 20, wherein the detecting of the previously detected concentration of carbon dioxide has been effected contemporaneously, or substantially contemporaneously, with the detecting of the previously detected flow rate of the gaseous exhaust material 18 previously discharged by the process 20, upon which the previously received flow sensor signal is based, and determining that a decrease in the rate (molar rate and/or volumetric rate) at which carbon dioxide is being discharged by the gaseous exhaust material producing process 20 has been effected, the controller effects at least one of: (a) a decrease in the intensity, or termination of supply, of the photosynthetically active light radiation being supplied to the reaction zone 10, and (b) a decrease in the rate of supply (molar rate of supply and/or volumetric rate of supply), or termination of supply, of a supplemental nutrient supply 42 being supplied to the reaction zone 10.

In some embodiments, for example, any one of: (a) a decrease in the flow rate of the gaseous exhaust material 18 being discharged by the gaseous exhaust material producing process 20, (b) a decrease in the concentration of carbon dioxide of the gaseous exhaust material 18 being discharged by the gaseous exhaust material producing process 20, or (c) a decrease in the rate of carbon dioxide being discharged by the gaseous exhaust material producing process 20, is an indicator of a decrease in the rate of supply of the discharged carbon dioxide reaction zone supply being supplied to the reaction zone 10. Because there is provided a decrease in the rate of supply of the discharged carbon dioxide reaction zone supply to the reaction zone 10, the rate of supply of one or more other material inputs, which are relevant to phototrophic biomass growth, are correspondingly reduced or terminated to conserve such inputs.

In another aspect, while carbon dioxide is being discharged by the gaseous exhaust material producing process 20, and while at least a fraction of the discharged carbon dioxide is being supplied to the reaction zone 10, wherein the at least a fraction of the discharged carbon dioxide which is being supplied to the reaction zone 10 defines a discharged carbon dioxide reaction zone supply, when a decrease in the rate of supply (molar rate of supply and/or volumetric rate of supply) of the discharged carbon dioxide reaction zone supply being supplied to the reaction zone 10 is detected, or when an indication of a decrease in the rate of supply (molar rate of supply and/or volumetric rate of supply) of the discharged carbon dioxide reaction zone supply being supplied to the reaction zone 10 is detected, either the rate of supply (molar rate of supply and/or volumetric rate of supply) of a supplemental carbon dioxide supply 92 to the reaction zone 10 is increased, or supply of the supplemental carbon dioxide supply 92 to the reaction zone 10 is initiated. In this respect, the increase in the rate of supply of a supplemental carbon dioxide supply 92 to the reaction zone 10, or the initiation of the supply of the supplemental carbon dioxide supply 92 to the reaction zone 10 is effected in response to the detecting of a decrease, or an indication of a decrease in the rate of supply (molar rate of supply and/or volumetric rate of supply) of the discharged carbon dioxide reaction zone supply being supplied to the reaction zone 10. In some embodiments, for example, the source of the supplemental carbon dioxide supply 92 is a carbon dioxide cylinder. In some embodiments, for example, the source of the supplemental carbon dioxide supply 92 is a supply of air. In some embodiments, for example, the detected decrease is a detected termination of the supply of the discharged carbon dioxide reaction zone supply to the reaction zone 10. In some embodiments, for example the detected indication of a decrease is a detected indication of the termination of the supply of the discharged carbon dioxide reaction zone supply to the reaction zone 10. In some embodiments, for example, the indication of a decrease in the rate of supply of the discharged carbon dioxide reaction zone supply being supplied to the reaction zone 10 is any of the indications described above.

In some of these embodiments, the exposing of the phototrophic biomass disposed in the reaction zone 10 to photosynthetically active light radiation is effected while the increasing of the molar rate of supply, or the initiation of supply, of the supplemental carbon dioxide supply 92 to the reaction zone 10 is being effected.

In some embodiments, for example, the supplemental carbon dioxide supply 92 is supplied for compensating for the decrease in the rate of supply of carbon dioxide being supplied by the gaseous exhaust material producing process 20 to the reaction zone 10, with a view to sustaining a substantially constant growth rate of the phototrophic biomass, when it is believed that the decrease (for example, the termination) is only of a temporary nature (such as less than two weeks). In this respect, in some embodiments, the supply of supply 92 to the reaction zone 10 continues after its initiation for a period of less than two (2) weeks, for example, less than one week, and as a further example, less than five (5) days, and as a further example, less than three (3) days, and as a further example, less than one (1) day. In some embodiments, for example, the supply of supply 92 to the reaction zone 10 continues after its initiation for a period of greater than 15 minutes, for example, greater than 30 minutes, and as a further example, greater than one (1) hour, and as a further example, greater than six (6) hours, and as a further example, greater than 24 hours.

In those embodiments where the increasing of the rate of supply (molar rate of supply and/or volumetric rate of supply), or the initiation of supply, of a supplemental carbon dioxide supply 92 to the reaction zone 10 is effected in response to the detection of an indication of a decrease in the rate of supply (molar rate of supply and/or volumetric rate of supply) of the discharged carbon dioxide reaction zone supply being supplied to the reaction zone 10, and the indication of a decrease in the rate of supply (molar rate of supply and/or volumetric rate of supply) of the discharged carbon dioxide reaction zone supply being supplied to the reaction zone 10, which is detected, is a decrease in the flow rate of the gaseous exhaust material 18 being discharged by the gaseous exhaust material producing process 20, in some of these embodiments, for example, a flow sensor 78 is provided for detecting the flow rate of the gaseous exhaust material 18 being discharged by the gaseous exhaust material producing process 20, and transmitting a signal representative of the detected flow rate of the gaseous exhaust material 18, being discharged by the gaseous exhaust material producing process 20, to the controller. Where molar flow rate is being detected, a gas analyzer operates integrally with the flow sensor 78. Upon the controller comparing a received signal from the flow sensor 78 which is representative of a currently detected flow rate of the gaseous exhaust material 18, being discharged by the gaseous exhaust material producing process 20, to a previously received signal representative of a previously detected flow rate of the gaseous exhaust material 18 previously being discharged by the process 20, and determining that a decrease in the flow rate of the gaseous exhaust material 18, being discharged by the gaseous exhaust material producing process 20, has been effected, the controller actuates the opening of a flow control element, such as a valve 921, to initiate supply of the supplemental carbon dioxide supply 92 to the reaction zone 10 from a source of the supplemental carbon dioxide supply 92, or to effect increasing of the rate of supply (molar rate of supply and/or volumetric rate of supply) of the supplemental carbon dioxide supply being supplied to the reaction zone 10.

In those embodiments where the increasing of the rate of supply (molar rate of supply and/or volumetric rate of supply), or the initiation of supply, of a supplemental carbon dioxide supply 92 to the reaction zone 10 is effected in response to the detection of an indication of a decrease in the rate of supply (molar rate of supply and/or volumetric rate of supply) of the discharged carbon dioxide reaction zone supply being supplied to the reaction zone 10, and the indication of a decrease in the rate of supply (molar rate of supply and/or volumetric rate of supply) of the discharged carbon dioxide reaction zone supply being supplied to the reaction zone 10 which is detected is a decrease in the concentration of carbon dioxide of the gaseous exhaust material 18 being discharged by the gaseous exhaust material producing process 20, in some embodiments, for example, a carbon dioxide sensor 781 is provided for detecting the concentration of carbon dioxide of the gaseous exhaust material 18 being discharged by the gaseous exhaust material producing process 20, and transmitting a signal representative of the detected concentration of carbon dioxide of the gaseous exhaust material 18 being discharged by the gaseous exhaust material producing process 20, to the controller. In some embodiments, the carbon dioxide sensor is a gas analyzer such that the concentration detected is a molar concentration. Upon the controller comparing a received signal from the carbon dioxide sensor 781 which is representative of the detected concentration of carbon dioxide of the gaseous exhaust material 18 being discharged by the gaseous exhaust material producing process 20, to a previously received signal representative of a previously detected concentration of carbon dioxide of the gaseous exhaust material 18 previously being discharged by the gaseous exhaust material producing process 20, and determining that a decrease in the concentration of carbon dioxide of the gaseous exhaust material 18 being discharged by the gaseous exhaust material producing process 20, has been effected, the controller actuates the opening of a flow control element, such as a valve 921, to initiate supply of the supplemental carbon dioxide supply 92 to the reaction zone 10, or to effect increasing of the rate of supply (molar rate of supply and/or volumetric rate of supply) of the supplemental carbon dioxide supply being supplied to the reaction zone 10.

In those embodiments where the increasing of the rate of supply (molar rate of supply and/or volumetric rate of supply) of a supplemental carbon dioxide supply 92 being supplied to the reaction zone, or the initiation of supply of a supplemental carbon dioxide supply 92 to the reaction zone 10, is effected in response to the detection of an indication of a decrease in the rate of supply (molar rate of supply and/or volumetric rate of supply) of the discharged carbon dioxide reaction zone supply to the reaction zone 10, when the indication of a decrease in the rate of supply (molar rate of supply and/or volumetric rate of supply) of the discharged carbon dioxide reaction zone supply to the reaction zone 10, which is detected is a decrease in the rate (molar rate and/or volumetric rate) at which carbon dioxide is being discharged by the gaseous exhaust material producing process 20, in some of these embodiments, for example, the decrease in the rate (molar rate and/or volumetric rate) at which carbon dioxide is being discharged by the gaseous exhaust material producing process 20 is based on a comparison between (i) a calculated rate at which carbon dioxide is being discharged by the gaseous exhaust producing process 20, wherein the calculation is based on the combination of a detected flow rate of the gaseous exhaust material 18 being discharged by the gaseous exhaust material producing process 20 and also a detected concentration of carbon dioxide of the gaseous exhaust material 18 being discharged by the gaseous exhaust material producing process 20, and (ii) a calculated rate at which carbon dioxide has previously been discharged by the gaseous exhaust producing process 20, wherein the calculation is based on the combination of a previously detected flow rate of the gaseous exhaust material 18 previously being discharged by the gaseous exhaust material producing process 20 and also a previously detected concentration of carbon dioxide of the gaseous exhaust material 18 previously being discharged by the gaseous exhaust material producing process 20. In this respect, a flow sensor 78 is provided for detecting the flow rate of the gaseous exhaust material 18 being discharged by the gaseous exhaust material producing process 20, and transmitting a signal representative of the detected flow rate of the gaseous exhaust material 18 being discharged by the gaseous exhaust material producing process 20, to the controller. In this respect also, a carbon dioxide sensor 781 is provided for detecting the concentration of carbon dioxide of the gaseous exhaust material 18 being discharged by the gaseous exhaust material producing process 20, and transmitting a signal representative of the detected concentration of carbon dioxide of the gaseous exhaust material 18 being discharged by the gaseous exhaust material producing process 20, to the controller. In some embodiments, the carbon dioxide sensor is a gas analyzer such that the concentration detected is a molar concentration. Upon the controller receiving a flow sensor signal from the flow sensor 78, which is representative of a detected flow rate of the gaseous exhaust material 18 being discharged by the gaseous exhaust material producing process 20, and also receiving a carbon dioxide sensor signal from a carbon dioxide sensor 781, which is representative of a detected concentration of carbon dioxide of the gaseous exhaust material 18 being discharged by the gaseous exhaust material producing process 20, wherein the detecting of the detected concentration of carbon dioxide of the gaseous exhaust material 18 is contemporaneous, or substantially contemporaneous, with the detecting of the detected flow rate of the gaseous exhaust material 18 being discharged by the process 20, upon which the flow sensor signal is based, and calculating a rate at which carbon dioxide is being discharged by the gaseous exhaust material producing process 20, based upon the received flow sensor signal and the received carbon dioxide sensor signal, and comparing the calculated rate at which carbon dioxide is being discharged by the gaseous exhaust material producing process 20 to a calculated rate at which carbon dioxide has previously been discharged by the gaseous exhaust material producing process 20, wherein the calculated rate at which carbon dioxide has previously been discharged by the gaseous exhaust material producing process 20 is based upon the combination of a previously received flow sensor signal, which is representative of a previously detected flow rate of the gaseous exhaust material 18 previously discharged by the gaseous exhaust material producing process 20, and a previously received carbon dioxide sensor signal, which is representative of a previously detected concentration of carbon dioxide of the gaseous exhaust material 18 previously discharged by the gaseous exhaust material producing process 20, wherein the detecting of the previously detected concentration of carbon dioxide has been effected contemporaneously, or substantially contemporaneously, with the detecting of the previously detected flow rate of the gaseous exhaust material 18 previously discharged by the process 20, upon which the previously received flow sensor signal is based, and determining that a decrease in the rate at which carbon dioxide is being discharged by the gaseous exhaust material producing process 20 has been effected, the controller actuates the opening of a flow control element, such as a valve 921, to initiate supply of the supplemental carbon dioxide supply 92 to the reaction zone 10, or to effect increasing of the rate of supply (molar rate of supply and/or volumetric rate of supply) of the supplemental carbon dioxide supply being supplied to the reaction zone 10.

In those embodiments where a decrease (or termination) in the rate of supply (molar rate of supply and/or volumetric rate of supply) of the discharged carbon dioxide reaction zone supply being supplied to the reaction zone 10 is detected, or when an indication of a decrease (or termination) in the rate of supply (molar rate of supply and/or volumetric rate of supply) of the discharged carbon dioxide reaction zone supply being supplied to the reaction zone 10 is detected, and, in response, either the rate of supply (molar rate of supply and/or volumetric rate of supply) of a supplemental carbon dioxide supply 92 to the reaction zone 10 is increased, or supply of the supplemental carbon dioxide supply 92 to the reaction zone 10 is initiated, in some of these embodiments, the process further includes initiating the supply of a supplemental gas-comprising material 48, or increasing the rate of supply (molar rate of supply and/or volumetric rate of supply) of a supplemental gas-comprising material 48, to the reaction zone 10.

In some embodiments, for example, the initiation of the supply of the supplemental gas-comprising material 48 to the reaction zone 10, or the increasing of the rate of supply (molar rate of supply and/or volumetric rate of supply) of the supplemental gas-comprising material 48 being supplied to the reaction zone 10, at least partially compensates for the reduction in supply rate (molar supply rate and/or volumetric supply rate) of material (such as material of the reaction zone feed material 22), or the termination of supply of material (such as material of the reaction zone feed material 22), to the reaction zone 10 which is effected by the decrease in the rate of supply (molar rate of supply and/or volumetric rate of supply), or by the termination of supply, of the discharged carbon dioxide reaction zone supply being supplied to the reaction zone 10, notwithstanding the initiation of the supply of the supplemental carbon dioxide supply 92 to the reaction zone 10, or the increase to the rate of supply (molar rate of supply and/or volumetric rate of supply) of a supplemental carbon dioxide supply 92 to the reaction zone 10, which is effected in response to the reduction in the rate of supply (molar rate of supply and/or volumetric rate of supply), or to the termination of supply, of the discharged carbon dioxide reaction zone supply being supplied to the reaction zone 10.

In some embodiments, for example, the compensation for the reduction in supply rate (molar supply rate and/or volumetric supply rate) of material (reaction zone feed material 22), or for the termination of supply of material (reaction zone feed material 22), to the reaction zone 10 which is effected, effects substantially no change to the rate of supply (molar rate of supply and/or volumetric rate of supply) of material (reaction zone feed material 22) to the reaction zone 10.

In some embodiments, the compensation for the reduction in supply rate (molar supply rate and/or volumetric supply rate) of material (reaction zone feed material 22), or for the termination of supply of material (reaction zone feed material 22), to the reaction zone 10 which is effected, mitigates against the reduced agitation of the reaction zone 10 which would otherwise be attributable to the reduction in the rate of supply, or the termination of supply, of the gaseous exhaust material reaction zone supply 24 to the reaction zone 10, which is effected by the decrease in the rate of supply, or by the termination of supply, of the discharged carbon dioxide reaction zone supply being supplied to the reaction zone 10.

In some embodiments, for example, the combination of any gaseous exhaust material reaction zone supply 24, the supplemental carbon dioxide supply 92, and the supplemental gas-comprising material defines a combined operative material flow that is supplied to the reaction zone as at least a fraction of the reaction zone feed material 22, and the reaction zone feed material 22 is supplied to the reaction zone 10 and effects agitation of material in the reaction zone such that any difference in mass concentration of the phototrophic biomass between any two points in the reaction zone 10 is less than 20%. In some embodiments, for example, the effected agitation is such that any difference in the mass concentration of the phototrophic biomass between any two points in the reaction zone 10 is less than 10%. In this respect, the supply of the supplemental gas-comprising material 48 is provided to mitigate against the creation of a phototrophic biomass concentration gradient between any two points in the reaction zone above a desired maximum.

The molar concentration of carbon dioxide, if any, of the supplemental gas-comprising material 48 is lower than the molar concentration of carbon dioxide of the supplemental carbon dioxide supply 92 being supplied to the reaction zone 10. In some embodiments, for example, the molar concentration of carbon dioxide of the supplemental gas material 48 is less than 3 mole % based on the total moles of the supplemental gas material 48. In some embodiments, for example, the molar concentration of carbon dioxide of the supplemental gas material 48 is less than 1 (one) mole % based on the total moles of the supplemental gas material 48.

In some embodiments, for example, the supplemental gas-comprising material 48 is a gaseous material. In some of these embodiments, for example, the supplemental gas-comprising material 48 includes a dispersion of gaseous material in a liquid material. In some of these embodiments, for example, the supplemental gas-comprising material 48 includes air. In some of these embodiments, for example, the supplemental gas-comprising material 48 is provided as a flow. The supplemental gas-comprising material 48 is supplied to the reaction zone 10 as a fraction of the reaction zone feed material 22.

In some embodiments, for example, the initiating of the supply of a supplemental gas-comprising material 48 to the reaction zone 10, or the increasing of the rate of supply (molar rate of supply and/or volumetric rate of supply) of a supplemental gas-comprising material 48 being supplied to the reaction zone 10, is effected also in response to the detection of a decrease in (or termination of) the rate of supply (molar rate of supply and/or volumetric rate of supply) of the discharged carbon dioxide reaction zone supply being supplied to the reaction zone 10, or of an indication of a decrease in (or termination of) the rate of supply (molar rate of supply and/or volumetric rate of supply) of the discharged carbon dioxide reaction zone supply being supplied to the reaction zone 10. Examples of suitable indications, and suitable sensors and control schemes for detecting such indications, are described above, and, in some embodiments, the initiating of the supply of a supplemental gas-comprising material 48 to the reaction zone 10, or the increasing of the rate of supply (molar rate of supply and/or volumetric rate of supply) of a supplemental gas-comprising material 48 being supplied to the reaction zone 10, is effected by the controller actuating the opening, or an increase in the opening, of a flow control element (such as valve 50) for effecting fluid coupling to a source of the supplemental gas-comprising material 48.

In some embodiments, for example, the initiating of the supply of a supplemental gas-comprising material 48 to the reaction zone 10, or the increasing of the rate of supply (molar rate of supply and/or volumetric rate of supply) of a supplemental gas-comprising material 48 being supplied to the reaction zone 10 is effected in response to the detection of a decrease, or an indication of a decrease, in the rate of supply (molar rate of supply and/or volumetric rate of supply) of the reaction zone feed material 22 being supplied to the reaction zone 10, while the supplemental carbon dioxide supply 92 is being supplied to the reaction zone 10. In some embodiments, for example, a flow sensor is provided for detecting the flow rate of the reaction zone feed material 22, and transmitting a signal representative of the detected flow rate of the reaction zone feed material 22 to the controller. In some embodiments, the carbon dioxide sensor is a gas analyzer such that the concentration detected is a molar concentration. Upon the controller comparing a received signal from the flow sensor which is representative of a currently detected flow rate of the reaction zone feed material 22, to a previously received signal representative of a previously detected flow rate of the reaction zone feed material 22, and determining that a decrease in the flow rate of the reaction zone feed material 22 has been effected, the controller actuates the opening of a flow control element, such as a valve (for example, valve 50), to initiate supply of the supplemental gas-comprising material 48 to the reaction zone 10 from a source of the supplemental gas-comprising material 48, or to effect increasing of the rate of supply of the supplemental gas-comprising material 48 being supplied to the reaction zone 10 from a source of the supplemental gas-comprising material 48.

In another aspect, while the gaseous exhaust material 18 is being discharged by the gaseous exhaust material producing process 20, wherein any of the gaseous exhaust material 18 being supplied to the reaction zone 10 defines a gaseous exhaust material reaction zone supply 24, supply of the gaseous exhaust material reaction zone supply 24 to the reaction zone 10 is modulated based on detection of at least one carbon dioxide processing capacity indicator. In some embodiments, for example, the gaseous exhaust material 18 is discharged in the form of a gaseous flow. In some embodiments, for example, the gaseous exhaust material reaction zone supply 24 is provided in the form of a gaseous flow. In some embodiments, for example, the modulation of the supply of the gaseous exhaust material reaction zone supply 24 is the modulation of the molar rate of supply of the gaseous exhaust material reaction zone supply 24. In some embodiments, the modulation is the modulation of the volumetric rate of supply of the gaseous exhaust material reaction zone supply 24. In some embodiments, for example, the exposing of the phototrophic biomass disposed in the reaction zone 10 to photosynthetically active light radiation is effected while the modulating of the gaseous exhaust material reaction zone supply 24 is being effected.

When the supply of the gaseous exhaust material reaction zone supply 24 to the reaction zone 10 is modulated based on detection of at least one carbon dioxide processing capacity indicator, in some embodiments, for example, the process further includes modulating of a supply of a bypass fraction of the discharged gaseous exhaust material 18 to another unit operation. The supply of the bypass fraction of the discharged gaseous exhaust material 18 to another unit operation defines a bypass gaseous exhaust material 60. The bypass gaseous exhaust material 60 includes carbon dioxide. The another unit operation converts the bypass gaseous exhaust material 60 such that its environmental impact is reduced.

As suggested above, modulating of a supply of the gaseous exhaust material reaction zone supply 24 to the reaction zone 10 is any one of initiating, terminating, increasing, decreasing, or otherwise changing the supply of the gaseous exhaust material reaction zone supply 24 to the reaction zone 10. Such modulation includes increasing (or decreasing) the number of moles (and/or volume) of gaseous exhaust material reaction zone supply 24 that are supplied to the reaction zone 10 over a time interval of a duration "D", relative to number of moles (or, alternatively, as the case may be, volume) of gaseous exhaust material reaction zone supply 24 that are supplied to the reaction zone 10 over a previous time interval of equivalent duration "D". In some of these embodiments, the time intervals include a period when gaseous exhaust material reaction zone supply 24 is being supplied to reaction zone 10 ("active supply period"), and a period when reaction zone 10 is not being supplied by gaseous exhaust material reaction zone supply 24 ("quiet period"), and the increasing (or decreasing) is effected by changing the duration of the "active supply period" relative to the duration of the "quiet period(s)", as between the time intervals.

Also, modulating of a supply of the bypass fraction of the discharged gaseous exhaust material 18 (ie. the bypass gaseous exhaust material 60) to another unit operation. is any one of initiating, terminating, increasing, decreasing, or otherwise changing the supply of the bypass gaseous exhaust material 60 to another unit operation.

The carbon dioxide processing capacity indicator is any characteristic that is representative of the capacity of the reaction zone 10 for receiving carbon dioxide and having at least a fraction of the received carbon dioxide converted in a photosynthesis reaction effected by phototrophic biomass disposed within the reaction zone.

In some embodiments, for example, the carbon dioxide processing capacity indicator is any characteristic of the process that is representative of the capacity of the reaction zone 10 for receiving carbon dioxide and having at least a fraction of the received carbon dioxide converted in a photosynthesis reaction effected by phototrophic biomass disposed within the reaction zone, such that the photosynthesis effects growth of the phototrophic biomass within the reaction zone 10. In this respect, the detection of the carbon dioxide processing capacity indicator is material to determining whether modulation of the supply of the gaseous exhaust material reaction zone supply 24 is required to effect a predetermined rate of growth of mass of the phototrophic biomass within the reaction zone 10.

In some embodiments, for example, the carbon dioxide processing capacity indicator is any characteristic of the process that is representative of the capacity of the reaction zone 10 for receiving carbon dioxide and having at least a fraction of the received carbon dioxide converted in a photosynthesis reaction effected by phototrophic biomass disposed within the reaction zone 10, such that any discharge of carbon dioxide from the reaction zone 10 is effected below a predetermined molar rate. In this respect, the detection of the carbon dioxide processing capacity indicator is material to determining whether modulation of the supply of the gaseous exhaust material reaction zone supply 24 to the reaction zone 10 is required to effect a predetermined molar rate of discharge of the carbon dioxide from the reaction zone 10.

In some embodiments, for example, the carbon dioxide processing capacity indicator which is detected is a pH within the reaction zone 10. In some embodiments, for example, the carbon dioxide processing capacity indicator which is detected is a mass concentration of phototrophic biomass within the reaction zone 10. Because any of phototrophic biomass-comprising product 500 that is being discharged from the reaction zone 10 includes a portion of material from within the reaction zone 10 (ie. phototrophic biomass-comprising product 500 that is being discharged from the reaction zone 10 is supplied with material from within the reaction zone 10), the detecting of a carbon dioxide processing capacity indicator (such as the pH within the reaction zone, or the phototrophic biomass mass concentration within the reaction zone) includes detecting of the carbon dioxide processing capacity indicator within the phototrophic biomass-comprising product 500 that is being discharged from the reaction zone 10

In some embodiments for example, the modulating of the supply of the gaseous exhaust material reaction zone supply 24 to the reaction zone 10 is based on detection of two or more carbon dioxide processing capacity indicators within the reaction zone 10.

In some embodiments, for example, while the gaseous exhaust material 18 is being discharged by the gaseous exhaust material producing process 20, wherein any gaseous exhaust material 18 which is being supplied to the reaction zone 10 defines a gaseous exhaust material reaction zone supply 24, when a carbon dioxide processing capacity indicator is detected in the reaction zone 10 which is representative of a capacity of the reaction zone 10 for receiving an increased molar rate of supply of carbon dioxide, the modulating of the supply of the gaseous exhaust material reaction zone supply 24 to the reaction zone 10 includes initiating the supply of the gaseous exhaust material reaction zone supply 24 to the reaction zone 10, or increasing the molar rate of supply (and/or volumetric rate of supply) of the gaseous exhaust material reaction zone supply 24 being supplied to the reaction zone 10. In this respect, the modulating is effected in response to the detection of a carbon dioxide processing capacity indicator in the reaction zone 10 which is representative of a capacity of the reaction zone 10 for receiving an increased molar rate of supply of carbon dioxide. In those embodiments where the outlet of the gaseous exhaust material producing process 20 is co-operatively disposed with another unit operation to effect supply of the bypass gaseous exhaust material 60 to the another unit operation, and while the bypass gaseous exhaust material 60 is being supplied to the another unit operation, in some of these embodiments, the process further includes effecting a decrease to the molar rate of supply (and/or volumetric rate of supply) of, or terminating the supply of, the bypass gaseous exhaust material 60 being supplied to the another unit operation. It is understood that, in some embodiments, the detecting of a capacity indicator which is representative of a capacity of the reaction zone 10 for receiving an increased molar rate of supply of carbon dioxide occurs while the reaction zone 10 is being supplied with the gaseous exhaust material reaction zone supply 24. It is also understood that, in other embodiments, the detecting of a capacity indicator which is representative of a capacity of the reaction zone 10 for receiving an increased molar rate of supply of carbon dioxide occurs while the reaction zone 10 is not being supplied with the gaseous exhaust material reaction zone supply 24.

In some embodiments, for example, while the gaseous exhaust material 18 is being discharged by the gaseous exhaust material producing process 20, and while at least a fraction of the gaseous exhaust material 18 is being supplied to the reaction zone 10, wherein the at least a fraction of the gaseous exhaust material 18 which is being supplied to the reaction zone 10 defines a gaseous exhaust material reaction zone supply 24, when a carbon dioxide processing capacity indicator is detected in the reaction zone 10 which is representative of a capacity of the reaction zone 10 for receiving a decreased molar rate of supply of carbon dioxide, the modulating of the supply of the gaseous exhaust material reaction zone supply 24 to the reaction zone 10 includes reducing the molar rate of supply (and/or volumetric rate of supply) of, or terminating the supply of, the gaseous exhaust material reaction zone supply 24 being supplied to the reaction zone 10. In this respect, the modulating is effected in response to the detection of a carbon dioxide processing capacity indicator in the reaction zone 10 which is representative of a capacity of the reaction zone 10 for receiving a decreased molar rate of supply of carbon dioxide. In those embodiments where the outlet of the gaseous exhaust material producing process 20 is co-operatively disposed with another unit operation to effect supply of the bypass gaseous exhaust material 60 to the another unit operation, in some of these embodiments, the process further includes initiating the supply of the bypass gaseous exhaust material 60 to the another unit operation, or effecting an increase to the molar rate of supply (and/or volumetric rate of supply) of the bypass gaseous exhaust material 60 being supplied to the another unit operation.

In some embodiments, for example, the carbon dioxide processing capacity indicator is a pH within the reaction zone 10. Operating with a pH in the reaction zone 10 which is above the predetermined high pH (indicating an insufficient molar rate of supply of carbon dioxide to the reaction zone 20), or which is below the predetermined low pH (indicating an excessive molar rate of supply of carbon dioxide to the reaction zone 10), effects less than a desired growth rate of the phototrophic biomass, and, in the extreme, could effect death of the phototrophic biomass. In some embodiments, for example, the pH which is detected in the reaction zone is detected in the reaction zone 10 with a pH sensor 46. The pH sensor 46 is provided for detecting the pH within the reaction zone, and transmitting a signal representative of the detected pH within the reaction zone to the controller.

In some embodiments, for example, while the gaseous exhaust material 18 is being discharged by the gaseous exhaust material producing process 20, wherein any of the gaseous exhaust material 18 which is supplied to the reaction zone 10 defines a gaseous exhaust material reaction zone supply 24, when a pH is detected in the reaction zone 10 that is above a predetermined high pH value, the modulating of the supply of the gaseous exhaust material reaction zone supply 24 to the reaction zone 10 includes initiating the supply of the gaseous exhaust material reaction zone supply 24 to the reaction zone 10, or increasing the molar rate of supply (and/or volumetric rate of supply) of the gaseous exhaust material reaction zone supply 24 being supplied to the reaction zone 10. In those embodiments where the outlet of the gaseous exhaust material producing process 20 is co-operatively disposed with another unit operation to effect supply of the bypass gaseous exhaust material 60 to the another unit operation, and while the bypass gaseous exhaust material 60 is being supplied to the another unit operation, in some of these embodiments, the process further includes effecting a decrease to the molar rate of supply (and/or volumetric rate of supply), or terminating the supply, of the bypass gaseous exhaust material 60 being supplied to the another unit operation. It is understood that, in some embodiments, the detecting of a pH in the reaction zone 10 that is above a predetermined high pH value occurs when the reaction zone 10 is being supplied with the gaseous exhaust material reaction zone supply 24. It is also understood that, in other embodiments, the detecting of a pH in the reaction zone 10 that is above a predetermined high pH value occurs when the reaction zone 10 is not being supplied with the gaseous exhaust material reaction zone supply 24.

In those embodiments when the pH within the reaction zone is above a predetermined high pH value, in some of these embodiments, upon the controller comparing a received signal from the pH sensor 47 which is representative of the detected pH within the reaction zone 10 to a target value (ie. the predetermined high pH value), and determining that the detected pH within the reaction zone 10 is above the predetermined high pH value, the controller responds by effecting initiation of the supply of the gaseous exhaust material reaction zone supply 24 to the reaction zone 10, or effecting an increase to the molar rate of supply (and/or volumetric rate of supply) of the gaseous exhaust material reaction zone supply 24 being supplied to the reaction zone 10. In some embodiments, for example, the initiation of supply of the gaseous exhaust material reaction zone supply 24 to the reaction zone 10 is effected by actuating opening of the flow control element 50 with the controller. In some embodiments, for example, the effecting of an increase to the molar supply rate (and/or volumetric supply rate) of the gaseous exhaust material reaction zone supply 24 being supplied to the reaction zone 10 is effected by actuating an increase to the opening of the flow control element 50 with the controller. The flow control element 50 is provided and configured to selectively control the molar rate (and/or volumetric rate) of flow of the supply of the gaseous exhaust material reaction zone supply 24 to the reaction zone 10 by selectively interfering with the flow of the supply of the gaseous exhaust material reaction zone supply 24 to the reaction zone 10, including by effecting pressure losses to the flow of the supply of the gaseous exhaust material reaction zone supply 24 to the reaction zone 10. In this respect, the initiation of supply, or the increase to the molar rate of supply (and/or volumetric rate of supply), of the gaseous exhaust material reaction zone supply 24 to the reaction zone 10 is effected by actuation of the flow control element 50. The predetermined high pH value depends on the phototrophic organisms of the biomass. In some embodiments, for example, the predetermined high pH value can be as high as 10.

In those embodiments where the outlet of the gaseous exhaust material producing process 20 is co-operatively disposed with another unit operation to effect supply of the bypass gaseous exhaust material 60 to the another unit operation, and while the bypass gaseous exhaust material 60 is being supplied to the another unit operation, in some of these embodiments, for example, upon the controller determining that the pH within the reaction zone 10 is above the predetermined high pH value, the controller further responds by effecting a decrease to the molar rate of supply (and/or volumetric rate of supply), or by effecting termination of the supply, of the bypass gaseous exhaust material 60 being supplied to the another unit operation. In some embodiments, for example, the decrease to the molar rate of supply (and/or volumetric rate of supply) of the bypass gaseous exhaust material 60 being supplied to the another unit operation is effected by the controller by actuating a decrease to the opening of a valve disposed between the gaseous exhaust material producing process 20 and the another unit operation, wherein the valve is configured to interfere with fluid communication between the gaseous exhaust material producing process 20 and the another unit operation. In some embodiments, for example, the termination of the supply of the bypass gaseous exhaust material 60 being supplied to the another unit operation is effected by the controller by actuation closure of a valve disposed between the gaseous exhaust material producing process 20 and the another unit operation, wherein the valve is configured to interfere with fluid communication between the gaseous exhaust material producing process 20 and the another unit operation.

Also in those embodiments where the outlet of the gaseous exhaust material producing process 20 is co-operatively disposed with another unit operation to effect supply of bypass gaseous exhaust material 60 to the another unit operation, and while bypass gaseous exhaust material 60 is being supplied to the another unit operation, in other ones of these embodiments, for example, the decrease to the molar rate of supply (and/or volumetric rate of supply), or the termination of supply, of the bypass gaseous exhaust material 60 being supplied to the another unit operation is effected when the pressure of the gaseous exhaust material 18 upstream of the another unit operation is below a predetermined pressure, wherein the decrease in pressure is effected in response to an initiation of the supply of the gaseous exhaust material reaction zone supply 24 to the reaction zone 10, or an increase to the molar rate of supply (and/or volumetric rate of supply) of the gaseous exhaust material reaction zone supply 24 being supplied to the reaction zone 10, either of which is effected by the controller in response to the determination that the detected pH within the reaction zone is above a predetermined high pH value. In such embodiments, upon the controller determining that the detected pH within the reaction zone is above the predetermined high pH value, the controller effects an initiation of the supply of the gaseous exhaust material reaction zone supply 24 to the reaction zone 10, or an increase to the molar rate of supply (and/or volumetric rate of supply) of the gaseous exhaust material reaction zone supply 24 being supplied to the reaction zone 10, as described above. The initiation of supply of, or the increase to the molar rate of supply (and/or volumetric rate of supply) of, the gaseous exhaust material reaction zone supply 24 to the reaction zone 10 effects a corresponding decrease in pressure of the gaseous exhaust material 18 such that the pressure of the gaseous exhaust material 18 upstream of the another unit operation becomes disposed below the predetermined pressure. When the pressure of the gaseous exhaust material 18 upstream of the another unit operation is below the predetermined pressure, the forces biasing closure of a closure element 64 (such as a valve), disposed between the gaseous exhaust material producing process 20 and the another unit operation and configured for interfering with fluid communication between the gaseous exhaust material producing process 20 and the another unit operation, exceed the fluid pressure forces acting to open the closure element 64. In some implementations, there is effected a decrease of the opening of the closure element 64, thereby effecting the decrease to the molar rate of supply (and/or volumetric rate of supply) of the bypass gaseous exhaust material 60 being supplied to the another unit operation. In other implementations, there is effected closure of the closure element 64, thereby effecting the termination of supply of the bypass gaseous exhaust material 60 being supplied to the another unit operation.

Also in those embodiments where the outlet of the gaseous exhaust material producing process 20 is co-operatively disposed with another unit operation to effect supply of bypass gaseous exhaust material 60 to the another unit operation, and while bypass gaseous exhaust material 60 is being supplied to the another unit operation, in other ones of these embodiments, for example, the decrease to the molar rate of supply (and/or volumetric rate of supply) of the bypass gaseous exhaust material 60 being supplied to the another unit operation is effected when the pressure of the gaseous exhaust material 18 upstream of the another unit operation is decreased, wherein the decrease in pressure of the gaseous exhaust material 18 is effected in response to an initiation of the supply of the gaseous exhaust material reaction zone supply 24 to the reaction zone 10, or an increase to the molar rate of supply (and/or volumetric rate of supply) of the gaseous exhaust material reaction zone supply 24 being supplied to the reaction zone 10, either of which is effected by the controller in response to the determination that the detected pH within the reaction zone is above a predetermined high pH value. The decrease in pressure of the gaseous exhaust material 18 upstream of the another unit operation effects a decrease in the molar rate of supply (and/or volumetric rate of supply) of the bypass gaseous exhaust material 60 being supplied to the another unit operation.

In some embodiments, for example, while the gaseous exhaust material 18 is being discharged by the gaseous exhaust material producing process 20, and while at least a fraction of the gaseous exhaust material 18 is being supplied to the reaction zone 10, wherein the at least a fraction of the gaseous exhaust material 18 which is being supplied to the reaction zone 10 defines a gaseous exhaust material reaction zone supply 24, when a pH is detected in the reaction zone 10 that is below a predetermined low pH value, the modulating of the supply of the gaseous exhaust material reaction zone supply 24 to the reaction zone 10 includes reducing the molar rate of supply (and/or volumetric rate of supply), or terminating the supply, of the gaseous exhaust material reaction zone supply 24 being supplied to the reaction zone 10. In those embodiments where the outlet of the gaseous exhaust material producing process 20 is co-operatively disposed with another unit operation to effect supply of the bypass gaseous exhaust material 60 to the another unit operation, in some of these embodiments, for example, the process further includes initiating the supply of the bypass gaseous exhaust material 60 to the another unit operation, or effecting an increase to the molar rate of supply (and/or volumetric rate of supply) of the bypass gaseous exhaust material 60 being supplied to the another unit operation.

In those embodiments where the pH within the reaction zone is below a predetermined low pH value, in some of these embodiments, for example, upon the controller comparing a received signal from the pH sensor 46 which is representative of the detected pH within the reaction zone 10 to a target value (ie. the predetermined low pH value), and determining that the detected pH within the reaction zone 10 is below the predetermined low pH value, the controller responds by effecting reduction of the molar rate of supply (and/or volumetric rate of supply) of, or effecting termination of the supply of, the gaseous exhaust material reaction zone supply 24 being supplied to the reaction zone 10. In some embodiments, for example, the effected reduction of the molar rate of supply (and/or volumetric rate of supply) of the gaseous exhaust material reaction zone supply 24 being supplied to the reaction zone 10 is effected by actuating a decrease in the opening of the flow control element 50 (such as a valve) with the controller. In some embodiments, for example, the effected termination of supply of the gaseous exhaust material reaction zone supply 24 being supplied to the reaction zone 10 is effected by actuating the closure of a flow control element 50 (such as a valve) with the controller. The predetermined low pH value depends on the phototrophic organisms of the biomass. In some embodiments, for example, the predetermined low pH value can be as low as 4.0.

In those embodiments where the outlet of the gaseous exhaust material producing process 20 is co-operatively disposed with another unit operation to effect supply of the bypass gaseous exhaust material 60 to the another unit operation, in some of these embodiments, for example, upon the controller determining that the pH within the reaction zone 10 is below the predetermined low pH value, the controller further responds by effecting initiation of the supply of the bypass gaseous exhaust material 60 to the another unit operation, or effecting an increase to the molar rate of supply (and/or volumetric rate of supply) of the bypass gaseous exhaust material 60 being supplied to the another unit operation. In some embodiments, for example, the initiation of the supply of the bypass gaseous exhaust material 60 to the another unit operation, or the increase to the molar rate of supply (and/or volumetric rate of supply) of the bypass gaseous exhaust material 60 being supplied to the another unit operation is effected by the controller actuating a valve disposed between the gaseous exhaust material producing process 20 and the another unit operation, wherein the valve is configured for interfering with fluid flow between the process 20 and the another unit operation. In some implementations, for example, the initiation of the supply of the bypass gaseous exhaust material 60 to the another unit operation is effected by the controller by actuating the opening of a valve disposed between the gaseous exhaust material producing process 20 and the another unit operation. In some implementations, for example, the increase to the molar rate of supply (and/or volumetric rate of supply) of the bypass gaseous exhaust material 60 to the another unit operation is effected by the controller by actuation of an increase to the opening of a valve disposed between the gaseous exhaust material producing process 20 and the another unit operation.

Also in those embodiments where the outlet of the gaseous exhaust material producing process 20 is co-operatively disposed with another unit operation to effect supply of bypass gaseous exhaust material 60 to the another unit operation, in other ones of these embodiments, for example, the initiation of the supply of the bypass gaseous exhaust material 60 to the another unit operation, or an increase in the molar rate of supply (and/or volumetric rate of supply) of the bypass gaseous exhaust material 60 to the another unit operation, is effected when the pressure of the gaseous exhaust material 18 upstream of the another unit operation is above a predetermined pressure, wherein the increase in pressure of the gaseous exhaust material 18 upstream of the another unit operation to above the predetermined pressure is effected in response to the reduction of the molar rate of supply (and/or volumetric rate of supply), or the termination of the supply, of the gaseous exhaust material reaction zone supply 24 being supplied to the reaction zone 10, either of which is effected by the controller in response to the determination that the detected pH within the reaction zone is below a predetermined low pH value. In such embodiments, upon the controller determining that the detected pH within the reaction zone by the pH sensor 47 is below a predetermined low pH value, the controller effects a reduction of the molar rate of supply (and/or volumetric rate of supply), or effects termination of the supply, of the gaseous exhaust material reaction zone supply 24 being supplied to the reaction zone 10, as described above. The reduction of the molar rate of supply (and/or volumetric rate of supply), or the termination of the supply, of the gaseous exhaust material reaction zone supply 24 being supplied to the reaction zone 10 effects a corresponding increase in pressure of the gaseous exhaust material 18 upstream of the another unit operation such that the pressure of the gaseous exhaust material 18 upstream of the another unit operation becomes disposed above a predetermined pressure. When the pressure of the gaseous exhaust material 18 upstream of the another unit operation is above the predetermined pressure, the forces biasing closure of a closure element 64 (such as a valve), disposed between the gaseous exhaust material producing process 20 and the another unit operation and configured for interfering with fluid communication between the gaseous exhaust material producing process 20 and the another unit operation, are exceeded by the fluid pressure forces of the gaseous exhaust material 18 acting to open the closure element 64. In some implementations, there is effected initiation of the opening of the closure element 64, which effects the initiation of supply of the bypass gaseous exhaust material 60 being supplied to the another unit operation, in response to the fluid pressure increase. In other implementations, there is effected an increase to the opening of the closure element 64, which effects the increase to the molar rate of supply (and/or volumetric rate of supply) of the bypass gaseous exhaust material 60 being supplied to the another unit operation, in response to the fluid pressure increase.

Also in those embodiments where the outlet of the gaseous exhaust material producing process 20 is co-operatively disposed with another unit operation to effect supply of bypass gaseous exhaust material 60 to the another unit operation, in other ones of these embodiments, for example, the increase in the molar rate of supply (and/or volumetric rate of supply) of the bypass gaseous exhaust material 60 being supplied to the another unit operation is effected in response to the increase in pressure of the gaseous exhaust material 18 upstream of the another unit operation, which is effected in response to the reduction of the molar rate of supply (and/or volumetric rate of supply), or the termination of the supply, of the gaseous exhaust material reaction zone supply 24 being supplied to the reaction zone 10, either of which is effected by the controller in response to the determination that the detected pH within the reaction zone is below a predetermined low pH value. In such embodiments, upon the controller determining that the detected pH within the reaction zone by the pH sensor 47 is below a predetermined low pH value, the controller effects a reduction of the molar rate of supply (and/or volumetric rate of supply), or effects termination of the supply, of the gaseous exhaust material reaction zone supply 24 being supplied to the reaction zone 10, as described above. The reduction of the molar rate of supply (and/or volumetric rate of supply) of, or the termination of the supply of, the gaseous exhaust material reaction zone supply 24 being supplied to the reaction zone 10 effects a corresponding increase in pressure of the gaseous exhaust material 18 upstream of the another unit operation. The increase in pressure of the gaseous exhaust material 18 upstream of the another unit operation effects the increase in the molar rate of supply (and/or volumetric rate of supply) of the bypass gaseous exhaust material 60 being supplied to the another unit operation.

In some embodiments, for example, the carbon dioxide processing capacity indicator is a mass concentration of phototrophic biomass within the reaction zone 10. In some embodiments, for example, it is desirable to control the mass concentration of the phototrophic biomass within the reaction zone 10, as, for example, higher overall yield of the harvested phototrophic biomass is effected when the mass concentration of the phototrophic biomass within the reaction zone 10 is maintained at a predetermined concentration or within a predetermined concentration range. In some embodiments, the detecting of the mass concentration of phototrophic biomass in the reaction zone 10 is effected with a cell counter 47. For example, a suitable cell counter is an AS-16F Single Channel Absorption Probe supplied by optek-Danulat, Inc. of Germantown, Wis., U.S.A. Other suitable devices for detecting mass concentration of phototrophic biomass include other light scattering sensors, such as a spectrophotometer. As well, the mass concentration of phototrophic biomass can be detected manually, and then input manually into the controller for effecting the desired response.

In some embodiments, the mass concentration of phototrophic biomass is detected using a sensor 300 that, in general, combines an absorbence sensor with a turbidity sensor. In this respect, the sensor 300 includes two different light emitters 302, 304 (small light emitting diodes (LEDs)), each configured to emit light of a different wavelength than the other, and an optical sensor 306 to detect light while the light is being emitted by the light emitters.

The two light emitters 303, 304 are provided for different purposes. The light emitter 302 is configured to emit light of a wavelength that would be absorbed by the phototrophic biomass. Where the phototrophic biomass is that of algae, in some embodiments, the light being emitted by the light emitter 302 is blue light and/or red light. In those embodiments where the algae is being grown in a photobioreactor 12 in the presence of red light, then the light emitter 302 is configured to emit blue light so as to obtain more accurate measurements. The other light emitter 304 is configured to emit light of a wavelength that would be reflected or scattered by the phototrophic biomass, or at least which is characterized such that there is a greater likelihood that such emitted light would be reflected or scattered by the phototrophic biomass relative to the light emitted by light emitter 302. Where the phototrophic biomass is that of algae, in some embodiments, the light being emitted by the light emitter 304 is green light. The two light emitters 302 and 304 are disposed in spaced-apart relationship relative to the optical sensor 306 (about 1 cm, but this could vary depending on the emitted light intensity and expected mass concentration of the phototrophic biomass). In operation, light emission, from light emitter 302 and light emitter 304, alternates between the two. In some embodiments, the light emissions from the sensor are characterized by alternating pulses of light from the light emitters 302 and 304. In some of these embodiments, for example, light emitter 302 emits a pulse of light for a defined time interval T1 while light emitter 304 emits substantially no light during this time interval T1, and then, at the completion of time interval T1, light emitter 304 emits a pulse of light for a defined time interval T2 while light emitter 304 emits substantially no light during this time interval T2, and this cycle is then repeated for as many cycles as is desired for effecting the desired detection of mass concentration of phototrophic biomass. By alternating light emissions between the light emitter 302 and 304, interference of the detection of light, being emitted from one of the light emitters 302, 304, by light being emitted from the other one of the light emitters 302, 304, is avoided or mitigated. The duration of each light pulse is not so critical, but typically about 1 sec would be used for each light emitter so that the optical sensor 306 has time to adjust to the new wavelength and record a value that is not affected by scattering of the other light emitter that just turned off.

When light is being emitted by light emitter 302, the optical sensor 306 detects light than has not been absorbed by the phototrophic biomass, and transmits, to a controller, a signal representative of the quantity of light that has not been absorbed by the phototrophic biomass, which is then compared by the controller to a signal representative of the intensity of light being emitted by light emitter 302, and converted into a signal representative of the quantity of light absorbed by the phototrophic biomass. When light is being emitted by light emitter 304, the optical sensor 306 detects light than has been scattered or reflected by the phototrophic biomass, and transmits, to a controller, a signal representative of the quantity of light that has been scattered or reflected by the phototrophic biomass. These signals are combined by the controller into a signal that is representative of a density measurement (ie. mass concentration of phototrophic biomass). The controller is calibrated based on predetermined correlation between algae mass concentration within an aqueous medium and the absorption of light, being emitted by the light emitter 302, by the phototrophic biomass, and the reflection (or scattering) of light, being emitted by the light emitter 304, by the phototrophic biomass. This correlation is predetermined based on calibration measurements to known mass concentrations of the phototrophic biomass which is to be grown within the aqueous medium disposed in the photobioreactor 12 (ie. defining the mass concentration of phototrophic biomass within the aqueous medium as a function of: (i) the absorption of light, being emitted by the light emitter 302, by the phototrophic biomass, and (ii) the reflection (or scattering) of light, being emitted by the light emitter 304, by the phototrophic biomass.

Referring to FIG. 4A, 4B and FIGS. 5A, 5B, in some embodiments, the light emitters 302, 304 and the optical sensor 306 are mounted within a common housing 308 and are configured for electrical connection to a power source and a control transmitter for measuring an electrical signal (current or voltage, depending on the control set-up) with wiring 310. For example, as illustrated in FIGS. 4A, 4B and FIGS. 5A, 5B, this configuration would be useful for effecting detection of mass concentration of phototrophic biomass within a vessel of a photobioreactor 12 In other embodiments, such as that illustrated in FIG. 6, for example, the light emitters 302, 304 and the optical sensor 306 do not necessarily require to be mounted within a common housing. In the embodiment illustrated in FIG. 6, this configuration of sensor 300 is co-operatively mounted to a conduit (such as a conduit 312 which is effecting the discharge of phototrophic biomass from the photobioreactor 12) for measuring mass concentration of phototrophic biomass within a slurry flowing through the conduit 312.

In this respect, in some embodiments, for example, while the gaseous exhaust material 18 is being discharged by the gaseous exhaust material producing process 20, and while at least a fraction of the gaseous exhaust material 18 is being supplied to the reaction zone 10, wherein the at least a fraction of the gaseous exhaust material 18 which is being supplied to the reaction zone 10 defines a gaseous exhaust material reaction zone supply 24, when a phototrophic biomass concentration is detected in the reaction zone 10 that is above a predetermined high mass concentration of phototrophic biomass (the "predetermined high target concentration value"), the modulating of the supply of the gaseous exhaust material reaction zone supply 24 to the reaction zone 10 includes reducing the molar rate of supply (and/or volumetric rate of supply), or terminating the supply, of the gaseous exhaust material reaction zone supply 24 being supplied to the reaction zone 10. In those embodiments where the outlet of the gaseous exhaust material producing process 20 is co-operatively disposed with another unit operation to effect supply of the bypass gaseous exhaust material 60 to the another unit operation, the process further includes initiating the supply of the bypass gaseous exhaust material 60 to the another unit operation, or effecting an increase to the molar rate of supply (and/or volumetric rate of supply) of the bypass gaseous exhaust material 60 being supplied to the another unit operation.

In those embodiments where the phototrophic biomass concentration within the reaction zone is above the predetermined high concentration target value, in some of these embodiments, upon the controller comparing a received signal from the cell counter 47, which is representative of the detected mass concentration of phototrophic biomass within the reaction zone 10, to the predetermined high concentration target value, and determining that the mass concentration of phototrophic biomass within the reaction zone 10 is above the predetermined high concentration target value, the controller responds by effecting reduction of the molar rate of supply (and/or volumetric rate of supply) of, or termination of the supply of, the gaseous exhaust material reaction zone supply 24 being supplied to the reaction zone 10. In some implementations, for example, the reduction of the molar rate of supply (and/or volumetric rate of supply) of the gaseous exhaust material reaction zone supply 24 being supplied to the reaction zone 10 is effected by actuating a decrease to the opening the flow control element 50 with the controller. In some implementations, for example, the termination of the supply of the gaseous exhaust material reaction zone supply 24 being supplied to the reaction zone 10 is effected by actuating closure of the flow control element 50 with the controller.

In those embodiments where the outlet of the gaseous exhaust material producing process 20 is co-operatively disposed with another unit operation to effect supply of bypass gaseous exhaust material 60 to the another unit operation, in some of these embodiments, for example, upon the controller comparing a received signal from the cell counter 47, which is representative of the mass concentration of phototrophic biomass within the reaction zone 10, to the predetermined high concentration target value, and determining that the mass concentration of phototrophic biomass within the reaction zone 10 is above the predetermined high concentration target value, the controller further responds by effecting initiation of the supply of the bypass gaseous exhaust material 60 to the another unit operation, or effecting an increase to the molar rate of supply (and/or volumetric rate of supply) of the bypass gaseous exhaust material 60 being supplied to the another unit operation. In some embodiments, for example, the initiation of the supply of the bypass gaseous exhaust material 60 to the another unit operation, or the increase to the molar rate of supply (and/or volumetric rate of supply) of the bypass gaseous exhaust material 60 being supplied to the another unit operation is effected by the controller actuating a valve disposed between the gaseous exhaust material producing process 20 and the another unit operation, wherein the valve is configured for interfering with fluid flow between the process 20 and the another unit operation. In some implementations, for example, the initiation of the supply the bypass gaseous exhaust material 60 to the another unit operation is effected by the controller by actuation of the opening of the valve disposed between the gaseous exhaust material producing process 20 and the another unit operation. In some implementations, for example, the increase to the molar rate of supply (and/or volumetric rate of supply) of the bypass gaseous exhaust material 60 being supplied to the another unit operation is effected by the controller by actuation of an increase in the opening of the valve disposed between the gaseous exhaust material producing process 20 and the another unit operation.

Also in those embodiments where the outlet of the gaseous exhaust material producing process 20 is co-operatively disposed with another unit operation to effect supply of bypass gaseous exhaust material 60 to the another unit operation, in other ones of these embodiments, for example, the initiation of the supply of the bypass gaseous exhaust material 60 to the another unit operation, or an increase in the molar rate of supply (and/or volumetric rate of supply) of the bypass gaseous exhaust material 60 being supplied to the another unit operation, is effected when the pressure of the gaseous exhaust material 18 upstream of the another unit operation is above a predetermined pressure, wherein the increase in pressure of the gaseous exhaust material 18 upstream of the another unit operation to above the predetermined pressure is effected in response to the reduction of the molar rate of supply (and/or volumetric rate of supply), or the termination of the supply, of the gaseous exhaust material reaction zone supply 24 being supplied to the reaction zone 10, either of which is effected by the controller in response to the determination that the detected mass concentration of phototrophic biomass within the reaction zone is above the predetermined high concentration target value. In such embodiments, upon the controller determining that the detected mass concentration of phototrophic biomass within the reaction zone by the cell counter 47 is above the predetermined high concentration target value, the controller effects a reduction of the molar rate of supply (and/or volumetric rate of supply), or termination of the supply, of the gaseous exhaust material reaction zone supply 24 being supplied to the reaction zone 10, as described above. The reduction of the molar rate of supply (and/or volumetric rate of supply) of, or the termination of the supply of, the gaseous exhaust material reaction zone supply 24 being supplied to the reaction zone 10 effects a corresponding increase in pressure of the gaseous exhaust material 18 upstream of the another unit operation such that the pressure of the gaseous exhaust material 18 becomes disposed above a predetermined pressure. When the pressure of the gaseous exhaust material 18 is above the predetermined pressure, the forces biasing closure of a closure element 64 (such as a valve), disposed between the gaseous exhaust material producing process 20 and the another unit operation and configured for interfering with fluid communication between the gaseous exhaust material producing process 20 and the another unit operation, are exceeded by the fluid pressure forces acting to open the closure element 64. In some implementations, there is effected an initiation of the opening of the closure element 64, thereby effecting the initiation of the supply of the bypass gaseous exhaust material 60 to the another unit operation. In some implementations, there is effected an increase in the opening of the closure element 64, thereby effecting the increase in the molar rate of supply (and/or volumetric rate of supply) of the bypass gaseous exhaust material 60 being supplied to the another unit operation.

Also in those embodiments where the outlet of the gaseous exhaust material producing process 20 is co-operatively disposed with another unit operation to effect supply of bypass gaseous exhaust material 60 to the another unit operation, in other ones of these embodiments, for example, the increase in the molar rate of supply (and/or volumetric rate of supply) of the bypass gaseous exhaust material 60 being supplied to the another unit operation is effected in response to the increase in pressure of the gaseous exhaust material 18 upstream of the another unit operation, which is effected in response to the reduction of the molar rate of supply (and/or volumetric rate of supply), or the termination of the supply, of the gaseous exhaust material reaction zone supply 24 being supplied to the reaction zone 10, either of which is effected by the controller in response to the determination that the detected mass concentration of phototrophic biomass within the reaction zone is above the predetermined high concentration target value. In such embodiments, upon the controller determining that the detected mass concentration of phototrophic biomass within the reaction zone by the cell counter 47 is above the predetermined high concentration target value, the controller effects a reduction of the molar rate of supply (and/or volumetric rate of supply), or effects termination of the supply, of the gaseous exhaust material reaction zone supply 24 being supplied to the reaction zone 10, as described above. The reduction of the molar rate of supply of (and/or volumetric rate of supply), or the termination of the supply of, the gaseous exhaust material reaction zone supply 24 to the reaction zone 10 effects a corresponding increase in pressure of the gaseous exhaust material 18 upstream of the another unit operation. The increase in pressure of the gaseous exhaust material 18 upstream of the another unit operation effects the increase in the molar rate of supply (and/or volumetric rate of supply) of the bypass gaseous exhaust material 60 being supplied to the another unit operation.

In some embodiments, for example, while the gaseous exhaust material 18 is being discharged by the gaseous exhaust material producing process 20, wherein any of the gaseous exhaust material 18 which is being supplied to the reaction zone 10 defines a gaseous exhaust material reaction zone supply 24, when a mass concentration of phototrophic biomass is detected in the reaction zone 10 that is below a predetermined low mass concentration of phototrophic biomass (a "predetermined low concentration target value"), the modulating of the supply of the gaseous exhaust material reaction zone supply 24 to the reaction zone 10 includes initiating the supply of the gaseous exhaust material reaction zone supply 24 to the reaction zone 10, or increasing the molar rate of supply (and/or volumetric rate of supply) of the gaseous exhaust material reaction zone supply 24 being supplied to the reaction zone 10. In those embodiments where the outlet of the gaseous exhaust material producing process 20 is co-operatively disposed with another unit operation to effect supply of the bypass gaseous exhaust material 60 to the another unit operation, and while the bypass gaseous exhaust material 60 is being supplied to the another unit operation, in some of these embodiments, the process further includes effecting a decrease to the molar rate of supply (and/or volumetric rate of supply) of, or terminating the supply of, the bypass gaseous exhaust material 60 to the another unit operation.

In those embodiments where the mass concentration of phototrophic biomass within the reaction zone is below the predetermined low concentration target value, in some of these embodiments, upon the controller comparing a received signal from the cell counter 47, which is representative of the detected mass concentration of phototrophic biomass within the reaction zone 10, to the predetermined low concentration target value, and determining that the detected mass concentration of phototrophic biomass within the reaction zone 10 is below the predetermined low concentration target value, the controller responds by effecting initiation of the supply of the gaseous exhaust material reaction zone supply 24 to the reaction zone 10, or effecting an increase to the molar rate of supply (and/or volumetric rate of supply) of the gaseous exhaust material reaction zone supply 24 being supplied to the reaction zone 10. In some embodiments, for example, this is effected by actuating the flow control element 50 with the controller. In some implementations, the initiation of supply of the gaseous exhaust material reaction zone supply 24 to the reaction zone 10 is effected by actuating opening of the flow control element 50 with the controller. In some implementations, the effecting of an increase to the molar supply rate (and/or volumetric supply rate) of the gaseous exhaust material reaction zone supply 24 being supplied to the reaction zone 10 is effected by actuating an increase to the opening of the flow control element 50 with the controller.

In those embodiments where the outlet of the gaseous exhaust material producing process 20 is co-operatively disposed with another unit operation to effect supply of the bypass gaseous exhaust material 60 to the another unit operation, and while the bypass gaseous exhaust material 60 is being supplied to the another unit operation, in some of these embodiments, for example, upon the controller comparing a received signal from the cell counter 47, which is representative of the mass concentration of phototrophic biomass within the reaction zone 10, to the low concentration target value, and determining that the mass concentration of phototrophic biomass within the reaction zone 10 is below the predetermined low concentration target value, the controller further responds by effecting a decrease to the molar rate of supply (and/or volumetric rate of supply), or by effecting the termination of the supply, of the bypass gaseous exhaust material 60 to the another unit operation. In some embodiments, for example, the decrease to the molar rate of supply (and/or volumetric rate of supply), or the termination of the supply, of the bypass gaseous exhaust material 60 to the another unit operation is effected by the controller by actuation of a valve disposed between the gaseous exhaust material producing process 20 and the another unit operation, wherein the valve is configured to interfere with fluid communication between the gaseous exhaust material producing process 20 and the another unit operation. In some implementations, for example, the decrease to the molar rate of supply (and/or volumetric rate of supply) of the bypass gaseous exhaust material 60 being supplied to the another unit operation is effected by the controller by actuating a decrease to the opening of a valve disposed between the gaseous exhaust material producing process 20 and the another unit operation. In some implementations, for example, the termination of the supply of the bypass gaseous exhaust material 60 being supplied to the another unit operation is effected by the controller by actuating closure of a valve disposed between the gaseous exhaust material producing process 20 and the another unit operation.

Also in those embodiments where the outlet of the gaseous exhaust material producing process 20 is co-operatively disposed with another unit operation to effect supply of bypass gaseous exhaust material 60 to the another unit operation, and while bypass gaseous exhaust material 60 is being supplied to the another unit operation, in other ones of these embodiments, for example, the decrease to the molar rate of supply (and/or volumetric rate of supply) of the bypass gaseous exhaust material 60 being supplied to the another unit operation, or the termination of the supply of the bypass gaseous exhaust material 60 being supplied to the another unit operation, is effected in response to a decrease in pressure of the gaseous exhaust material 18 upstream of the another unit operation, wherein the decrease in pressure is effected in response to an initiation of the supply of the gaseous exhaust material reaction zone supply 24 to the reaction zone 10, or an increase to the molar rate of supply (and/or volumetric rate of supply) of the gaseous exhaust material reaction zone supply 24 being supplied to the reaction zone 10, either of which is effected by the controller in response to the determination that the detected mass concentration of phototrophic biomass within the reaction zone is below the predetermined low concentration target value. The pressure decrease is such that the pressure of the gaseous exhaust material 18 upstream of the another unit operation is below a predetermined minimum pressure, and the forces biasing closure of a closure element 64 (such as a valve), disposed between the gaseous exhaust material producing process 20 and the another unit operation and configured for interfering with fluid communication between the gaseous exhaust material producing process 20 and the another unit operation, exceed the fluid pressure forces of the gaseous exhaust material 18 acting to open the closure element 64. In some implementations, there is effected a decrease in the opening of the closure element 64, which effects the decrease to the molar rate of supply (and/or volumetric rate of supply) of the bypass gaseous exhaust material 60 to the another unit operation, in response to the decrease in the pressure of the gaseous exhaust material 18 upstream of the another unit operation. In other implementations, there is effected a closure of the closure element 64, which effects the termination of the supply of the bypass gaseous exhaust material 60 to the another unit operation, in response to the decrease in the pressure of the gaseous exhaust material 18 upstream of the another unit operation.

Also in those embodiments where the outlet of the gaseous exhaust material producing process 20 is co-operatively disposed with another unit operation to effect supply of bypass gaseous exhaust material 60 to the another unit operation, and while bypass gaseous exhaust material 60 is being supplied to the another unit operation, in other ones of these embodiments, for example, the decrease to the molar rate of supply (and/or volumetric rate of supply) of the bypass gaseous exhaust material 60 being supplied to the another unit operation is effected in response to a decrease in pressure of the gaseous exhaust material 18 upstream of the another unit operation, wherein the decrease in pressure is effected in response to an initiation of the supply of the gaseous exhaust material reaction zone supply 24 to the reaction zone 10, or an increase to the molar rate of supply (and/or volumetric rate of supply) of the gaseous exhaust material reaction zone supply 24 being supplied to the reaction zone 10, either of which is effected by the controller in response to the determination that the detected mass concentration of phototrophic biomass within the reaction zone is below the predetermined low concentration target value. The decrease in pressure of the gaseous exhaust material 18 upstream of the another unit operation effects a decrease in the molar rate of supply (and/or volumetric rate of supply) of the bypass gaseous exhaust material 60 being supplied to the another unit operation.

In some embodiments, for example, the modulating of the bypass gaseous exhaust material 60 to the another unit operation is effected while the modulating of the supply of the gaseous exhaust material reaction zone supply 24 to the reaction zone 10 is being effected. In this respect, in some embodiments, for example, the initiation of the supply of the bypass gaseous exhaust material 60 to the another unit operation, or the increase to the molar rate of supply (and/or volumetric rate of supply) of the bypass gaseous exhaust material 60 being supplied to the another unit operation, is effected while the decrease in the molar rate of supply (and/or volumetric rate of supply), or the termination of the supply, of the gaseous exhaust material reaction zone supply 24 being supplied to the reaction zone 10 is being effected. Also in this respect, the decrease to the molar rate of supply (and/or volumetric rate of supply), or the termination of the supply, of the bypass gaseous exhaust material 60 being supplied to the another unit operation is effected while the initiation of the supply of the gaseous exhaust material reaction zone supply 24, or the increase in the molar rate of supply (and/or volumetric rate of supply), of the gaseous exhaust material reaction zone supply 24 being supplied to the reaction zone 10, is being effected.

In some embodiments, for example, the flow control element 50 is a flow control valve. In some embodiments, for example, the flow control element 50 is a three-way valve which also regulates the supply of a supplemental gas-comprising material 48, which is further described below.

In some embodiments, for example, the closure element 64 is any one of a valve, a damper, or a stack cap.

In some embodiments, for example, when the gaseous exhaust material reaction zone supply 24 is supplied to the reaction zone 10 as a flow, the flowing of the gaseous exhaust material reaction zone supply 24 is at least partially effected by a prime mover 38. For such embodiments, examples of a suitable prime mover 38 include a blower, a compressor, a pump (for pressurizing liquids including the gaseous exhaust material reaction zone supply 24), and an air pump. In some embodiments, for example, the prime mover 38 is a variable speed blower and the prime mover 38 also functions as the flow control element 50 which is configured to selectively control the flow rate of the reaction zone feed material 22 and define such flow rate.

In some embodiments, for example, the another unit operation is a smokestack 62. The smokestack 62 is configured to receive the bypass gaseous exhaust material 60 supplied from the outlet of the gaseous exhaust material producing process 20. When operational, the bypass gaseous exhaust material 60 is disposed at a pressure that is sufficiently high so as to effect flow through the smokestack 62. In some of these embodiments, for example, the flow of the bypass gaseous exhaust material 60 through the smokestack 62 is directed to a space remote from the outlet of the gaseous exhaust material producing process 20. Also in some of these embodiments, for example, the bypass gaseous exhaust material 60 is supplied from the outlet when the pressure of the gaseous exhaust material 18 exceeds a predetermined maximum pressure. In such embodiments, for example, the exceeding of the predetermined maximum pressure by the gaseous exhaust material 18 effects an opening of the closure element 64, to thereby effect supply of the bypass gaseous exhaust material 60.

In some embodiments, for example, the smokestack 62 is provided to direct the bypass fraction of the gaseous exhaust material 18 to a space remote from the outlet which discharges the gaseous exhaust material 18 from the gaseous exhaust material producing process 20, in response to a detected carbon dioxide processing capacity indicator which is representative of a capacity of the reaction zone 10 for receiving a decreased molar rate of supply of carbon dioxide from the gaseous exhaust material reaction zone supply 24, so as to mitigate against a gaseous discharge of an unacceptable carbon dioxide concentration to the environment.

In some embodiments, for example, the smokestack 62 is an existing smokestack 62 which has been modified to accommodate lower throughput of gaseous flow as provided by the bypass gaseous exhaust material 60. In this respect, in some embodiments, for example, an inner liner is inserted within the smokestack 62 to accommodate the lower throughput.

In some embodiments, for example, the another unit operation is a separator which effects removal of carbon dioxide from the bypass gaseous exhaust material 60. In some embodiments, for example, the separator is a gas absorber.

In some embodiments, for example, while the gaseous exhaust material 18 is being discharged by the gaseous exhaust material producing process 20, and while at least a fraction of the gaseous exhaust material 18 is being supplied to the reaction zone 10, wherein the at least a fraction of the gaseous exhaust material 18 which is being supplied to the reaction zone 10 defines a gaseous exhaust material reaction zone supply 24, when a carbon dioxide processing capacity indicator is detected in the reaction zone 10 which is representative of a capacity of the reaction zone 10 for receiving a decreased molar rate of supply of carbon dioxide, (for example, a detected pH within the reaction zone that is below a predetermined low pH value, or a detected mass concentration of phototrophic biomass within the reaction zone that is above a predetermined high mass concentration of phototrophic biomass), and the modulating of the gaseous exhaust material reaction zone supply 24, in response to the detecting of the carbon dioxide processing capacity indicator which is representative of a capacity of the reaction zone 10 for receiving a decreased molar rate of supply of carbon dioxide, includes reducing the molar rate of supply (and/or volumetric rate of supply), or terminating the supply, of the gaseous exhaust material reaction zone supply 24 being supplied to the reaction zone 10, the process further includes initiating the supply of a supplemental gas-comprising material 48 to the reaction zone 10, or increasing the molar rate of supply (and/or volumetric rate of supply) of a supplemental gas-comprising material 48 being supplied to the reaction zone 10.

The molar concentration of carbon dioxide, if any, of the supplemental gas-comprising material 48 is lower than the molar concentration of carbon dioxide of the at least a fraction of the gaseous exhaust material 18 being supplied to the reaction zone 10 from the gaseous exhaust material producing process 20. In some embodiments, for example, the molar concentration of carbon dioxide of the supplemental gas material 48 is less than 3 mole % based on the total moles of the supplemental gas material 48. In some embodiments, for example, the molar concentration of carbon dioxide of the supplemental gas material 48 is less than 1 (one) mole % based on the total moles of the supplemental gas material 48. In some embodiments, for example, the supplemental gas-comprising material 48 is supplied to the reaction zone 10 as a fraction of the reaction zone feed material 22. In some embodiments, for example, the reaction zone feed material 22 is a gaseous material. In some embodiments, for example, the reaction zone feed material 22 includes a dispersion of gaseous material in a liquid material.

In some embodiments, for example, the molar supply rate reduction (and/or volumetric supply rate reduction), or the termination of the supply, of the gaseous exhaust material reaction zone supply 24, being supplied to the reaction zone 10, effected by the modulating of the supply of the gaseous exhaust material reaction zone supply 24 to the reaction zone, co-operates with the supplying of the supplemental gas-comprising material 48 to the reaction zone 10 to effect a reduction in the molar rate of supply, or the termination of supply, of carbon dioxide being supplied to the reaction zone 10. In some embodiments, for example, the initiation of the supply, or the increase to the molar rate of supply (and/or volumetric rate of supply), of the bypass gaseous exhaust material 60 to the another unit operation is effected while the decrease in the molar rate of supply (and/or volumetric rate of supply), or the termination of the supply, of the gaseous exhaust material reaction zone supply 24 being supplied to the reaction zone 10 is being effected, and while the initiating of the supply of the supplemental gas-comprising material 48 to the reaction zone 10, or the increasing of the molar rate of supply (and/or volumetric rate of supply), of the supplemental gas-comprising material 48 being supplied to the reaction zone 10, is being effected.

In some of these embodiments, and as described above, the flow control element 50 is a three-way valve, and is operative to modulate supply of the supplemental gas-comprising material 48 to the reaction zone, in combination with the modulation of the supply of the gaseous exhaust material reaction zone supply 24 to the reaction zone 10, in response to the carbon dioxide processing capacity indicator. In this respect, when a carbon dioxide processing capacity indicator is detected in the reaction zone 10 which is representative of a capacity of the reaction zone for receiving a decreased molar rate of supply of carbon dioxide, (for example, a detected pH within the reaction zone that is below a predetermined low pH value, or a detected mass concentration of phototrophic biomass within the reaction zone that is above a predetermined high mass concentration of phototrophic biomass), the controller responds by actuating the valve 50 to initiate the supply of the supplemental gas-comprising material 48 to the reaction zone 10, or increase the molar rate of supply (and/or volumetric rate of supply) of the supplemental gas-comprising material 48 being supplied to the reaction zone 10. In some embodiments, while the supplemental gas-comprising material 48 is being supplied to the reaction zone 10, when a carbon dioxide processing capacity indicator is detected in the reaction zone 10 which is representative of a capacity of the reaction zone for receiving an increased molar rate of supply of carbon dioxide (for example, a detected pH within the reaction zone that is above a predetermined high pH value, or a detected mass concentration of phototrophic biomass within the reaction zone that is below a predetermined low mass concentration of phototrophic biomass), the controller responds by actuating the valve 50 to reduce the molar rate of supply (and/or volumetric rate of supply), or terminate the supply, of the supplemental gas-comprising material 48 being supplied to the reaction zone 10.

In another aspect, while the gaseous exhaust material 18 is being discharged by the gaseous exhaust material producing process 20, and while at least a fraction of the gaseous exhaust material 18 is being supplied to the reaction zone 10, wherein the at least a fraction of the gaseous exhaust material 18 which is being supplied to the reaction zone 10 defines a gaseous exhaust material reaction zone supply 24, and there is effected a reduction in the molar rate of supply (and/or volumetric rate of supply), or the termination of the supply, of the gaseous exhaust material reaction zone supply 24 being supplied to the reaction zone 10, the process further includes initiating the supply of a supplemental gas-comprising material 48, or increasing the molar rate of supply (and/or volumetric rate of supply) of a supplemental gas-comprising material 48, to the reaction zone 10.

In some embodiments, for example, the initiating of the supply of a supplemental gas-comprising material 48 to the reaction zone 10, or the increasing of the molar rate of supply (and/or volumetric rate of supply) of a supplemental gas-comprising material 48 being supplied to the reaction zone 10 is effected in response to the detection of the reduction in the molar rate of supply (and/or volumetric rate of supply) of, or the termination of the supply of, the gaseous exhaust material reaction zone supply 24 being supplied to the reaction zone 10, or of an indication of the reduction in the molar rate of supply of (and/or volumetric rate of supply), or the termination of the supply of, the gaseous exhaust material reaction zone supply 24 being supplied to the reaction zone 10. For example, the reduction in the molar rate of supply (and/or volumetric rate of supply) of, or the termination of the supply of, the gaseous exhaust material reaction zone supply 24 being supplied to the reaction zone 10 being effected in response to the detecting of the carbon dioxide processing capacity indicator which is representative of a capacity of the reaction zone 10 for receiving a decreased molar rate of supply of carbon dioxide, is described above. In some embodiments, for example, a flow sensor is provided for detecting the molar flow rate (in which case, a gas analyzer would also be used) or volumetric flow rate of the gaseous exhaust material reaction zone supply 24, and transmitting a signal representative of the detected molar flow rate (or volumetric flow rate, as the case may be) of the gaseous exhaust material reaction zone supply 24 to the controller. Upon the controller comparing a received signal from the flow sensor which is representative of a currently detected molar flow rate (or volumetric flow rate, as the case may be) of the gaseous exhaust material reaction zone supply 24, to a previously received signal representative of a previously detected molar flow rate (or volumetric flow rate, as the case may be) of the gaseous exhaust material reaction zone supply 24, and determining that a decrease in the molar flow rate (or volumetric flow rate, as the case may be) of the gaseous exhaust material reaction zone supply 24 has been effected, the controller actuates the opening of a flow control element, such as a valve (for example, valve 50), to initiate supply of the supplemental gas-comprising material 48 to the reaction zone 10 from a source of the supplemental gas-comprising material 48, or to effect increasing of the molar rate of supply (and/or volumetric rate of supply) of the supplemental gas-comprising material 48 being supplied to the reaction zone 10 from a source of the supplemental gas-comprising material 48.

In other ones of these embodiments, the reduction in the molar rate of supply (and/or volumetric rate of supply), or the termination of the supply, of the gaseous exhaust material reaction zone supply 24 to the reaction zone 10 is effected by a reduction in the molar rate (and/or volumetric rate) at which the gaseous exhaust material 18 is being discharged by the gaseous exhaust material producing process 20. In some of these embodiments, for example, the corresponding initiating of the supply of a supplemental gas-comprising material 48 to the reaction zone 10, or the corresponding increasing of the molar rate of supply (and/or volumetric rate of supply) of a supplemental gas-comprising material 48 being supplied to the reaction zone 10 is effected in response to the detection of the reduction in the molar rate (and/or volumetric rate) at which the gaseous exhaust material 18 is being discharged by the gaseous exhaust material producing process 20, or of an indication of the reduction in the molar rate (and/or volumetric rate) at which the gaseous exhaust material 18 is being discharged by the gaseous exhaust material producing process 20. In some embodiments, for example, a flow sensor is provided for detecting the molar flow rate (in which case, a gas analyzer would also be used) or volumetric flow rate of the gaseous exhaust material 18, and transmitting a signal representative of the detected molar flow rate (or volumetric flow rate, as the case may be) of the gaseous exhaust material 18 to the controller. Upon the controller comparing a received signal from the flow sensor which is representative of a currently detected molar flow rate (or volumetric flow rate, as the case may be) of the gaseous exhaust material 18, to a previously received signal representative of a previously detected molar flow rate (or volumetric flow rate, as the case may be) of the gaseous exhaust material 18, and determining that a decrease in the molar flow rate (or volumetric flow rate, as the case may be) of the gaseous exhaust material 18 has been effected, the controller actuates the opening of a flow control element, such as a valve (for example, valve 50), to initiate supply of the supplemental gas-comprising material 48 to the reaction zone 10 from a source of the supplemental gas-comprising material 48, or to effect increasing of the molar rate of supply (and/or volumetric rate of supply) of the supplemental gas-comprising material 48 being supplied to the reaction zone 10 from a source of the supplemental gas-comprising material 48.

In some embodiments, for example, the exposing of the phototrophic biomass disposed in the reaction zone 10 to photosynthetically active light radiation is effected while the initiation of the supply of the supplemental gas-comprising material 48 to the reaction zone 10, or the increasing of the molar rate of supply (and/or volumetric rate of supply) of the supplemental gas-comprising material 48 to the reaction zone 10, is being effected. In some embodiments, for example, the modulation of the supply of the supplemental gas-comprising material 48 to the reaction zone 10 is effected by the flow control element 50, for example, upon actuation by the controller. In some embodiments, the actuation by the controller is effected when a detected molar flow rate (or volumetric flow rate) of the gaseous exhaust material 18 being discharged by the gaseous exhaust material producing process 20, is compared to a previously detected molar flow rate (or volumetric flow rate) of the gaseous exhaust material 18 being discharged by the gaseous exhaust material producing process 20, and it is determined that there has been a decrease in the molar flow rate (or volumetric flow rate) of the gaseous exhaust material 18 being discharged by the gaseous exhaust material producing process 20.

With respect to any of the above-described embodiments of the process where there is the reduction in the molar rate of supply (and/or volumetric rate of supply), or the termination of supply, of the gaseous exhaust material reaction zone supply 24 to the reaction zone 10, and where there is initiated the supply of the supplemental gas-comprising material 48 to the reaction zone 10, or the increase to the molar rate of supply (and/or volumetric rate of supply) of the supplemental gas-comprising material 48 to the reaction zone 10, in some of these embodiments, for example, the initiation of the supply of the supplemental gas-comprising material 48 to the reaction zone 10, or the increasing of the molar rate of supply (and/or volumetric rate of supply) of the supplemental gas-comprising material 48 being supplied to the reaction zone 10, at least partially compensates for the reduction in molar supply rate (and/or volumetric supply rate) of material (such as material of the reaction zone feed material 22), or the termination of supply of material (such as material of the reaction zone feed material 22), to the reaction zone 10 which is effected by the reduction in the molar rate of supply (and/or volumetric rate of supply), or by the termination of supply, of the gaseous exhaust material reaction zone supply 24 to the reaction zone 10. In some embodiments, for example, the compensation for the reduction in molar supply rate (and/or volumetric supply rate) of material (such as material of the reaction zone feed material 22), or for the termination of supply of material (such as material of the reaction zone feed material 22), to the reaction zone 10 which is effected by the reduction in the molar rate of supply (and/or volumetric rate of supply), or by the termination of supply, of the gaseous exhaust material reaction zone supply 24 to the reaction zone 10, as effected by the initiation of the supply, or the increasing of the molar rate of supply (and/or volumetric rate of supply), of the supplemental gas-comprising material 48, effects substantially no change to the molar rate of supply (and/or volumetric rate of supply) of material (such as material of the reaction zone feed material 22) to the reaction zone 10.

In some embodiments, the combination of: (a) the reduction of the molar rate of supply (and/or volumetric rate of supply), or the termination of supply, of the gaseous exhaust material reaction zone supply 24 to the reaction zone 10, and (b) the initiation of the supply, or the increase to the molar rate of supply (and/or volumetric rate of supply), of the supplemental gas-comprising material 48 to the reaction zone 10, mitigates against the reduced agitation of the reaction zone 10 attributable to the reduction in the molar rate of supply (and/or volumetric rate of supply), or the termination of supply, of the gaseous exhaust material reaction zone supply 24 to the reaction zone 10. In some embodiments, for example, the combination of the supplemental gas-comprising material and any of the gaseous exhaust material reaction zone supply 24 is supplied to the reaction zone as at least a fraction of the reaction zone feed material 22, and the reaction zone feed material 22 is supplied to the reaction zone 10 and effects agitation of material in the reaction zone such that any difference in the mass concentration of the phototrophic biomass between any two points in the reaction zone 10 is less than 20%. In some embodiments, for example, the effected agitation is such that any difference in the mass concentration of the phototrophic biomass between any two points in the reaction zone 10 is less than 10%. The supply of the supplemental gas-comprising material 48 is provided to mitigate against the creation of a phototrophic biomass concentration gradient between any two points in the reaction zone above a desired maximum.

In some embodiments, for example, the supplemental gas-comprising material 48 is a gaseous material. In some of these embodiments, for example, the supplemental gas-comprising material 48 includes a dispersion of gaseous material in a liquid material. In some of these embodiments, for example, the supplemental gas-comprising material 48 includes air. In some of these embodiments, for example, the supplemental gas-comprising material 48 is provided as a flow.

In some circumstances, it is desirable to grow phototrophic biomass using carbon dioxide of the gaseous exhaust material 18 being discharged from the gaseous exhaust material producing process 20, but the molar concentration of carbon dioxide in the discharged gaseous exhaust material 18 is excessive for effecting a desired growth rate of the phototrophic biomass. In this respect, when a reaction zone feed material 22 is supplied to the reaction zone 10, and the reaction zone feed material 22 is supplied by the gaseous exhaust material reaction zone supply 24 being discharged by the gaseous exhaust material producing process 20, such that the gaseous exhaust material reaction zone supply 24 defines at least a fraction of the reaction zone feed material 22, the phototrophic biomass may respond adversely when exposed to the reaction zone feed material 22, if the carbon dioxide concentration of the reaction zone feed material 22 is excessive, such carbon dioxide concentration being at least partly attributable to the molar concentration of carbon dioxide of the gaseous exhaust material 18 from which the gaseous exhaust material reaction zone supply 24 is derived.

In other circumstances, when a reaction zone feed material 22 is supplied to the reaction zone 10, and the reaction zone feed material 22 is supplied by the supplemental carbon dioxide supply 92, such that the supplemental carbon dioxide supply 92 defines at least a fraction of the reaction zone feed material 22, the supplemental carbon dioxide supply 92 may include a relatively high concentration of carbon dioxide (such as greater than 90 mol % carbon dioxide based on the total moles of supplemental carbon dioxide supply 92), such that the phototrophic biomass may respond adversely when exposed to the reaction zone feed material 22.

In this respect, in another aspect, carbon dioxide is supplied to the reaction zone 10, and the supplied carbon dioxide defines the reaction zone carbon dioxide supply. A carbon dioxide concentrated supply 25A is provided, wherein the carbon dioxide concentrated supply 25A includes the reaction zone carbon dioxide supply. The carbon dioxide concentrated supply 25A is admixed with a supplemental gaseous dilution agent 90. The admixing effects production of a diluted carbon dioxide supply 25B, wherein the molar concentration of carbon dioxide of the diluted carbon dioxide supply 25B is less than the molar concentration of carbon dioxide of the carbon dioxide concentrate supply 25A. At least a fraction of the diluted carbon dioxide zone supply 25B is supplied to the reaction zone 10. The molar concentration of carbon dioxide of the supplemental gaseous dilution agent 90 is less than the molar concentration of carbon dioxide of the carbon dioxide concentrated supply 25A. In some embodiments, for example, the reaction zone carbon dioxide supply includes, or is defined by, carbon dioxide discharged by the gaseous exhaust material producing process 20. In some embodiments, for example, the reaction zone carbon dioxide supply includes, or is defined by, the supplemental carbon dioxide supply 92.

In another aspect, while the gaseous exhaust material 18 is being discharged by the gaseous exhaust material producing process 20, a carbon dioxide concentrated supply 25A is admixed with the supplemental gaseous dilution agent 90, wherein the carbon dioxide concentrated supply 25A includes a gaseous exhaust material-derived supply 24A, wherein the gaseous exhaust material-derived supply 24A is defined by at least a fraction of the gaseous exhaust material 18 which is being discharged by the gaseous exhaust material producing process 20. The admixing effects production of a diluted carbon dioxide supply 25B, wherein the molar concentration of carbon dioxide of the diluted carbon dioxide zone supply 25B is less than the molar concentration of carbon dioxide of the carbon dioxide concentrated supply 25A. At least a fraction of the diluted carbon dioxide supply 25B is supplied to the reaction zone 10. The molar concentration of carbon dioxide of the supplemental gaseous dilution agent 90 is less than the molar concentration of carbon dioxide of the carbon dioxide concentrated supply 25A. In some of these embodiments, for example, the exposing of the phototrophic biomass disposed in the reaction zone 10 to photosynthetically active light radiation is effected while the admixing of the carbon dioxide concentrated supply 25A with the supplemental gaseous dilution agent 90 is being effected. In some embodiments, for example, the carbon dioxide concentrated supply 25A is defined by the gaseous exhaust material-derived supply 24A. In some embodiments, for example, the carbon dioxide concentrated supply 25A includes the supplemental carbon dioxide supply 92. In some of these embodiments, for example. the supplying of the supplemental carbon dioxide supply 92 to the carbon dioxide concentrated supply 25A is being effected while the admixing is being effected.

In some embodiments, for example, the diluted carbon dioxide supply 25B includes a molar concentration of carbon dioxide that is below a predetermined maximum molar concentration of carbon dioxide. In some embodiments, for example, the predetermined maximum molar concentration of carbon dioxide is at least 30 mol % based on the total moles of the diluted carbon dioxide supply 25B. In some embodiments, for example, the predetermined maximum molar concentration of carbon dioxide is at least 20 mol % based on the total moles of the diluted carbon dioxide supply 25B. In some embodiments, for example, the predetermined maximum molar concentration of carbon dioxide is at least 10 mol % based on the total moles of the diluted carbon dioxide supply 25B.

In some embodiments, for example, the admixing of the supplemental gaseous dilution agent 90 with the carbon dioxide concentrated supply 25A is effected in response to detection of a molar concentration of carbon dioxide in the gaseous exhaust material 18 being discharged from the carbon dioxide producing process 20 that is greater than a predetermined maximum molar concentration of carbon dioxide. In some embodiments, for example, the predetermined maximum molar concentration of carbon dioxide is at least 10 mole % based on the total moles of the gaseous exhaust material 18. In some embodiments, for example, the predetermined maximum molar concentration of carbon dioxide is at least 20 mole % based on the total moles of the gaseous exhaust material 18. In some embodiments, for example, the predetermined maximum molar concentration of carbon dioxide is at least 30 mole % based on the total moles of the gaseous exhaust material 18. In this respect, in some embodiments, for example, a carbon dioxide sensor 781 is provided for detecting the molar concentration of carbon dioxide of the gaseous exhaust material 18 being discharged, and transmitting a signal representative of the molar concentration of carbon dioxide of the gaseous exhaust material 18 being discharged by the gaseous exhaust material producing process 20, to the controller. In some embodiments, the carbon dioxide sensor is a gas analyzer such that the concentration detected is a molar concentration. Upon the controller comparing a received signal from the carbon dioxide sensor 781, which is representative of a detected molar concentration of carbon dioxide of the gaseous exhaust material 18, to a predetermined maximum molar concentration of carbon dioxide, and determining that the molar concentration of carbon dioxide of the gaseous exhaust material 18 is greater than the predetermined maximum molar concentration of carbon dioxide, the controller actuates opening of, or an increase to the opening of, a control valve 901 which effects supply of the supplemental gaseous dilution agent 90 for admixing with the carbon dioxide concentrated supply 25A.

In some embodiments, for example, while carbon dioxide is being discharged by the gaseous exhaust material producing process 20, and while at least a fraction of the discharged carbon dioxide is being supplied to the reaction zone 10, wherein the at least a fraction of the discharged carbon dioxide which is being supplied to the reaction zone 10 defines a discharged carbon dioxide reaction zone supply, when an indication of a decrease in the molar rate of supply of the discharged carbon dioxide reaction zone supply to the reaction zone 10 is detected, either the molar rate of supply of a supplemental carbon dioxide supply 92 being supplied to the reaction zone 10 is increased, or supply of the supplemental carbon dioxide supply 92 to the reaction zone 10 is initiated. While the supplemental carbon dioxide supply 92 is being supplied to a carbon dioxide concentrated supply 25A, in response to the detection of the indication of a decrease in the molar rate of supply of the discharged carbon dioxide reaction zone supply to the reaction zone 10, such that at least a fraction of the carbon dioxide concentrated supply 25A is defined by the supplemental carbon dioxide supply 92, and while at least a fraction of the carbon dioxide concentrated supply 25A is being supplied to the reaction zone 10, the carbon dioxide concentrated supply 25A is admixed with the supplemental gaseous dilution agent 90 to effect production of the diluted carbon dioxide supply 25B. In some embodiments, for example, the source of the supplemental carbon dioxide supply 92 is a carbon dioxide cylinder. In some embodiments, for example, the source of the supplemental carbon dioxide supply 92 is a supply of air. In some of these embodiments, the exposing of the phototrophic biomass disposed in the reaction zone 10 to photosynthetically active light radiation is effected while the carbon dioxide concentrated supply 25A is admixed with the supplemental carbon dioxide supply 92 to effect production of the diluted carbon dioxide supply 25B, and while at least a fraction of the diluted carbon dioxide supply 25B is being supplied to the reaction zone 10. In some embodiments, for example, the carbon dioxide concentrated supply 25A is admixed with the supplemental carbon dioxide supply 92 to effect production of the diluted carbon dioxide supply 25B such that the diluted carbon dioxide supply 25B includes a molar concentration of carbon dioxide below the predetermined maximum concentration of carbon dioxide. In some embodiments, for example, the admixing is effect in response to the detection of a molar concentration of carbon dioxide in the carbon dioxide concentrated supply 25A (which includes the supplemental carbon dioxide supply 92) that is above the predetermined maximum molar concentration of carbon dioxide. In some embodiments, for example, the indication of a decrease in the molar rate of supply of the discharged carbon dioxide reaction zone supply to the reaction zone 10 is any of the indications described above. In some embodiments, for example, the supplemental carbon dioxide supply 92 is provided for compensating for the decrease in the molar rate of supply of the gaseous exhaust material reaction zone supply 24 being supplied to the reaction zone 10, with a view to sustaining a constant growth rate of the phototrophic biomass, when it is believed that the decrease is only of a temporary nature (such as less than two weeks).

In those embodiments where the carbon dioxide concentrated supply 25A includes the supplemental carbon dioxide supply 92, and the carbon dioxide concentrated supply 25A is being admixed with the supplemental gaseous dilution agent 90 to produce the diluted carbon dioxide supply 25B, and at least a fraction of the diluted carbon dioxide supply 25B is supplied to the reaction zone, the admixing of the carbon dioxide concentrated supply 25A with the supplemental gaseous dilution agent 90 is configured to produce the diluted carbon dioxide supply 25B including a predetermined molar concentration of carbon dioxide.

In some embodiments, for example, the supplemental gaseous dilution agent 90 is gaseous material. In some embodiments, for example, the supplemental gaseous dilution agent 90 includes air. In some embodiments, for example, the supplemental gaseous dilution agent 90 is being supplied to the carbon dioxide concentrated supply 25A as a flow.

The reaction mixture disposed in the reaction zone 10 is exposed to photosynthetically active light radiation so as to effect photosynthesis. The photosynthesis effects growth of the phototrophic biomass. In some embodiments, for example, there is provided the carbon dioxide-enriched phototrophic biomass disposed in the aqueous medium, and the carbon dioxide-enriched phototrophic biomass disposed in the aqueous medium is exposed to photosynthetically active light radiation so as to effect photosynthesis.

In some embodiments, for example, the light radiation is characterized by a wavelength of between 400-700 nm. In some embodiments, for example, the light radiation is in the form of natural sunlight. In some embodiments, for example, the light radiation is provided by an artificial light source 14. In some embodiments, for example, light radiation includes natural sunlight and artificial light.

In some embodiments, for example, the intensity of the provided light is controlled so as to align with the desired growth rate of the phototrophic biomass in the reaction zone 10. In some embodiments, regulation of the intensity of the provided light is based on measurements of the growth rate of the phototrophic biomass in the reaction zone 10. In some embodiments, regulation of the intensity of the provided light is based on the molar rate of supply of carbon dioxide to the reaction zone feed material 22.

In some embodiments, for example, the light is provided at pre-determined wavelengths, depending on the conditions of the reaction zone 10. Having said that, generally, the light is provided in a blue light source to red light source ratio of 1:4. This ratio varies depending on the phototrophic organism being used. As well, this ratio may vary when attempting to simulate daily cycles. For example, to simulate dawn or dusk, more red light is provided, and to simulate mid-day condition, more blue light is provided. Further, this ratio may be varied to simulate artificial recovery cycles by providing more blue light.

It has been found that blue light stimulates algae cells to rebuild internal structures that may become damaged after a period of significant growth, while red light promotes algae growth. Also, it has been found that omitting green light from the spectrum allows algae to continue growing in the reaction zone 10 even beyond what has previously been identified as its "saturation point" in water, so long as sufficient carbon dioxide and, in some embodiments, other nutrients, are supplied.

With respect to artificial light sources, for example, suitable artificial light source 14 include submersible fiber optics, light-emitting diodes, LED strips and fluorescent lights. Any LED strips known in the art can be adapted for use in the process. In the case of the submersible LEDs, the design includes the use of solar powered batteries to supply the electricity. In the case of the submersible LEDs, in some embodiments, for example, energy sources include alternative energy sources, such as wind, photovoltaic cells, fuel cells, etc. to supply electricity to the LEDs.

With respect to those embodiments where the reaction zone 10 is disposed in a photobioreactor 12 which includes a tank, in some of these embodiments, for example, the light energy is provided from a combination of sources, as follows. Natural light source 16 in the form of solar light is captured though solar collectors and filtered with custom mirrors that effect the provision of light of desired wavelengths to the reaction zone 10. The filtered light from the solar collectors is then transmitted through light guides or fiber optic materials into the photobioreactor 12, where it becomes dispersed within the reaction zone 10. In some embodiments, in addition to solar light, the light tubes in the photobioreactor 12 contains high power LED arrays that can provide light at specific wavelengths to either complement solar light, as necessary, or to provide all of the necessary light to the reaction zone 10 during periods of darkness (for example, at night). In some embodiments, with respect to the light guides, for example, a transparent heat transfer medium (such as a glycol solution) is circulated through light guides within the photobioreactor 12 so as to regulate the temperature in the light guides and, in some circumstances, provide for the controlled dissipation of heat from the light guides and into the reaction zone 10. In some embodiments, for example, the LED power requirements can be predicted and, therefore, controlled, based on trends observed with respect to the gaseous exhaust material 18, as these observed trends assist in predicting future growth rate of the phototrophic biomass.

In some embodiments, the exposing of the reaction mixture to photosynthetically active light radiation is effected while the supplying of the reaction feed material 22 is being effected.

In some embodiments, for example, the growth rate of the phototrophic biomass is dictated by the available gaseous exhaust material reaction zone supply 24 (defining the at least a fraction of the gaseous exhaust material 18 discharged by the gaseous exhaust material producing process 20 and being supplied to the reaction zone 10). In turn, this defines the nutrient, water, and light intensity requirements to maximize phototrophic biomass growth rate. In some embodiments, for example, a controller, e.g. a computer-implemented system, is provided to be used to monitor and control the operation of the various components of the process disclosed herein, including lights, valves, sensors, blowers, fans, dampers, pumps, etc.

Reaction zone product 500 is discharged from the reaction zone. The reaction zone product 500 includes phototrophic biomass 58. In some embodiments, for example, the reaction zone product 500 includes at least a fraction of the contents of the reaction zone 10. In this respect, the discharge of the reaction zone product 500 effects harvesting of the phototrophic biomass. In some embodiments, for example, a reaction zone gaseous effluent product 80 is also discharged from the reaction zone 10.

In another aspect, there is provided a process for growing a phototrophic biomass in a reaction zone 10 that includes modulating of the rate of discharge of phototrophic biomass based on the detection of a phototrophic biomass growth indicator. In some embodiments, for example, the rate of discharge of phototrophic biomass being modulated is a rate of discharge of mass of the phototrophic biomass.

The reaction mixture, in the form of a production purpose reaction mixture that is operative for effecting photosynthesis upon exposure to photosynthetically active light radiation, is disposed within the reaction zone 10. The production purpose reaction mixture includes phototrophic biomass in the form of production purpose phototrophic biomass that is operative for growth within the reaction zone 10. In this respect, a reaction zone concentration of mass of production purpose phototrophic biomass is provided in the reaction zone 10.

It is understood that the term "production purpose" has been introduced to differentiate the reaction mixture and the phototrophic biomass, of a process for growing phototrophic biomass, from "evaluation purpose reaction mixture" and "evaluation purpose phototrophic biomass", which are in some embodiments, integral to the predetermination of a phototrophic biomass growth indicator target value, as further explained below.

While the reaction mixture disposed in the reaction zone 10 is exposed to photosynthetically active light radiation and growth of the production purpose phototrophic biomass is being effected within the reaction mixture, and while production purpose phototrophic biomass is discharging from the reaction zone 10, when a difference between a phototrophic biomass growth indicator from within the reaction zone and a predetermined phototrophic biomass growth indicator target value is detected, the process includes modulating the rate of discharge of mass of the production purposes phototrophic biomass from the reaction zone 10, wherein the predetermined phototrophic biomass growth indicator target value is correlated with a predetermined growth rate of the production purpose phototrophic biomass within the reaction mixture which is disposed within the reaction zone 10 and is being exposed to the photosynthetically active light radiation. In some embodiments, for example, the predetermined growth rate of the production purpose phototrophic biomass is a growth rate of mass (or mass concentration) of production purpose phototrophic biomass. The effected growth of the production purpose phototrophic biomass includes growth effected by photosynthesis. In some embodiments, for example, the growth includes that effected by metabolic processes that consume supplemental nutrients disposed within the reaction mixture.

The predetermined phototrophic biomass growth indicator target value corresponds to the phototrophic biomass growth indicator target value at which the growth rate of the production purpose phototrophic biomass, within the reaction mixture which is disposed within the reaction zone 10 and is being exposed to the photosynthetically active light radiation, is the predetermined growth rate.

In some embodiments, for example, the effected growth of the production purpose phototrophic biomass is being effected within 10% of the predetermined growth rate of the production purpose phototrophic biomass within the reaction mixture which is disposed within the reaction zone 10 and is being exposed to photosynthetically active light radiation. In some embodiments, the effected growth of the production purpose phototrophic biomass is being effected within 5% of the predetermined growth rate of the production purpose phototrophic biomass within the reaction mixture which is disposed within the reaction zone 10 and is being exposed to the photosynthetically active light radiation. In some embodiments, the effected growth of the production purpose phototrophic biomass is being effected within 1% of the predetermined growth rate of the production purpose phototrophic biomass within the reaction mixture which is disposed within the reaction zone 10 and is being exposed to the photosynthetically active light radiation.

In some embodiments, for example, the modulating is effected in response to comparing of a detected phototrophic biomass growth indicator to the predetermined phototrophic biomass growth indicator target value.

In some embodiments, for example, the process further includes detecting a phototrophic biomass growth indicator to provide the detected phototrophic biomass growth indicator.

In some embodiments, for example, the phototrophic biomass growth indicator is a mass concentration of the phototrophic biomass within the reaction mixture disposed within the reaction zone 10.

In some embodiments, for example, the detected phototrophic biomass growth indicator is representative of the mass concentration of the production purpose phototrophic biomass within the reaction mixture disposed within the reaction zone 10. In this respect, in some of these embodiments, for example, the detected phototrophic biomass growth indicator is the mass concentration of the production purpose phototrophic biomass within the reaction mixture disposed within the reaction zone 10. In other ones of these embodiments, for example, the detected phototrophic biomass growth indicator is the mass concentration of the production purpose phototrophic biomass within the reaction zone product 500. In some embodiments, for example, the detecting of the concentration is effected by a cell counter 47. For example, a suitable cell counter is an AS-16F Single Channel Absorption Probe supplied by optek-Danulat, Inc. of Germantown, Wis., U.S.A. Other suitable devices for detecting a mass concentration of phototrophic biomass indication include other light scattering sensors, such as a spectrophotometer. As well, the mass concentration of phototrophic biomass can be detected manually, and then input manually into a controller for effecting the desired response.

In some embodiments, the mass concentration of phototrophic biomass is detected using a sensor 300 that, in general, combines an absorbence sensor with a turbidity sensor. In this respect, the sensor 300 includes two different light emitters 302, 304 (small light emitting diodes (LEDs)), each configured to emit light of a different wavelength than the other, and an optical sensor 306 to detect light while the light is being emitted by the light emitters.

The two light emitters 303, 304 are provided for different purposes. The light emitter 302 is configured to emit light of a wavelength that would be absorbed by the phototrophic biomass. Where the phototrophic biomass is that of algae, in some embodiments, the light being emitted by the light emitter 302 is blue light and/or red light. In those embodiments where the algae is being grown in a photobioreactor 12 in the presence of red light, then the light emitter 302 is configured to emit blue light so as to obtain more accurate measurements. The other light emitter 304 is configured to emit light of a wavelength that would be reflected or scattered by the phototrophic biomass, or at least which is characterized such that there is a greater likelihood that such emitted light would be reflected or scattered by the phototrophic biomass relative to the light emitted by light emitter 302. Where the phototrophic biomass is that of algae, in some embodiments, the light being emitted by the light emitter 304 is green light. The two light emitters 302 and 304 are disposed in spaced-apart relationship relative to the optical sensor 306 (about 1 cm, but this could vary depending on the emitted light intensity and expected mass concentration of the phototrophic biomass). In operation, light emission, from light emitter 302 and light emitter 304, alternates between the two. In some embodiments, the light emissions from the sensor are characterized by alternating pulses of light from the light emitters 302 and 304. In some of these embodiments, for example, light emitter 302 emits a pulse of light for a defined time interval T1 while light emitter 304 emits substantially no light during this time interval T1, and then, at the completion of time interval T1, light emitter 304 emits a pulse of light for a defined time interval T2 while light emitter 304 emits substantially no light during this time interval T2, and this cycle is then repeated for as many cycles as is desired for effecting the desired detection of mass concentration of phototrophic biomass. By alternating light emissions between the light emitter 302 and 304, interference of the detection of light, being emitted from one of the light emitters 302, 304, by light being emitted from the other one of the light emitters 302, 304, is avoided or mitigated. The duration of each light pulse is not so critical, but typically about 1 sec would be used for each light emitter so that the optical sensor 306 has time to adjust to the new wavelength and record a value that is not affected by scattering of the other light emitter that just turned off.

When light is being emitted by light emitter 302, the optical sensor 306 detects light than has not been absorbed by the phototrophic biomass, and transmits, to a controller, a signal representative of the quantity of light that has not been absorbed by the phototrophic biomass, which is then compared by the controller to a signal representative of the intensity of light being emitted by light emitter 302, and converted into a signal representative of the quantity of light absorbed by the phototrophic biomass. When light is being emitted by light emitter 304, the optical sensor 306 detects light than has been scattered or reflected by the phototrophic biomass, and transmits, to a controller, a signal representative of the quantity of light that has been scattered or reflected by the phototrophic biomass. These signals are combined by the controller into a signal that is representative of a density measurement (ie. mass concentration of phototrophic biomass). The controller is calibrated based on predetermined correlation between algae mass concentration within an aqueous medium and the absorption of light, being emitted by the light emitter 302, by the phototrophic biomass, and the reflection (or scattering) of light, being emitted by the light emitter 304, by the phototrophic biomass. This correlation is predetermined based on calibration measurements to known mass concentrations of the phototrophic biomass which is to be grown within the aqueous medium disposed in the photobioreactor 12 (ie. defining the mass concentration of phototrophic biomass within the aqueous medium as a function of: (i) the absorption of light, being emitted by the light emitter 302, by the phototrophic biomass, and (ii) the reflection (or scattering) of light, being emitted by the light emitter 304, by the phototrophic biomass.

Referring to FIG. 4A, 4B and FIGS. 5A, 5B, in some embodiments, the light emitters 302, 304 and the optical sensor 306 are mounted within a common housing 308 and are configured for electrical connection to a power source and a control transmitter for measuring an electrical signal (current or voltage, depending on the control set-up) with wiring 310. For example, as illustrated in FIGS. 4A, 4B and FIGS. 5A, 5B, this configuration would be useful for effecting detection of mass concentration of phototrophic biomass within a vessel of a photobioreactor 12 In other embodiments, such as that illustrated in FIG. 6, for example, the light emitters 302, 304 and the optical sensor 306 do not necessarily require to be mounted within a common housing. In the embodiment illustrated in FIG. 6, this configuration of sensor 300 is co-operatively mounted to a conduit (such as a conduit 312 which is effecting the discharge of phototrophic biomass from the photobioreactor 12) for measuring mass concentration of phototrophic biomass within a slurry flowing through the conduit 312.

Aside from measuring phototrophic biomass concentration within the photobioreactor 12, or within the fluid passage that is discharging slurry including harvested phototrophic biomass, the sensor 300 could be used to measure the mass concentration of phototrophic biomass within the return water 72 recovered from dewatering operations, compared with the mass concentration of phototrophic biomass being discharged from the photobioreactor 12, to determine separation efficiency of the dewatering operation.

In some embodiments, for example, the effecting of the growth of the phototrophic biomass includes supplying carbon dioxide to the reaction zone 10 and exposing the production purpose reaction mixture to photosynthetically active light radiation. In some embodiments, for example, the supplied carbon dioxide is supplied from the gaseous exhaust material 18 of the gaseous exhaust material producing process 20. In some embodiments, for example, the supplied carbon dioxide is supplied from the gaseous exhaust material 18 of the gaseous exhaust material producing process 20 while the gaseous exhaust material 18 is being discharged by the gaseous exhaust material producing process 20, and while at least a fraction of the gaseous exhaust material 18 is being supplied to the reaction zone feed material 22 (as the gaseous exhaust material reaction zone supply 24), and while the reaction zone feed material 22 is being supplied to the reaction zone 10. In this respect, in some embodiments, for example, the carbon dioxide is supplied to the reaction zone 10 while the growth is being effected, wherein at least a fraction of the carbon dioxide being supplied to the reaction zone 10 is supplied from a gaseous exhaust material 18 while the gaseous exhaust material 18 is being discharged from a gaseous exhaust material producing process 20.

In some embodiments, for example, the production purpose reaction mixture further includes water and carbon dioxide.

In some of these embodiments, for example, the predetermined rate of growth of the phototrophic biomass is based upon the maximum rate of growth of the phototrophic biomass within the reaction mixture which is disposed within the reaction zone 10 and is being exposed to the photosynthetically active light radiation, as described above. In this respect, when the predetermined rate of growth of the phototrophic biomass is a rate of growth of mass (or mass concentration) of the phototrophic biomass, the predetermined rate of growth of mass (or mass concentration) of the phototrophic biomass is based upon the maximum rate of growth of mass (or mass concentration) of the phototrophic biomass within the reaction mixture which is disposed within the reaction zone 10 and is being exposed to photosynthetically active light radiation.

In some embodiments, for example, the predetermined growth rate of the production purpose phototrophic biomass is at least 90% of the maximum growth rate of the production purpose phototrophic biomass within the reaction mixture which is disposed within the reaction zone 10 and is being exposed to the photosynthetically active light radiation. In some embodiments, for example, the predetermined growth rate is at least 95% of the maximum growth rate of the production purpose phototrophic biomass within the reaction mixture which is disposed within the reaction zone 10 and is being exposed to the photosynthetically active light radiation. In some embodiments, for example, the predetermined growth rate is at least 99% of the maximum growth rate of the production purpose phototrophic biomass within the reaction mixture which is disposed within the reaction zone 10 and is being exposed to the photosynthetically active light radiation. In some embodiments, for example, the predetermined growth rate is equivalent to the maximum growth rate of the production purpose phototrophic biomass within the reaction mixture which is disposed within the reaction zone 10 and is being exposed to the photosynthetically active light radiation.

Figure 7:
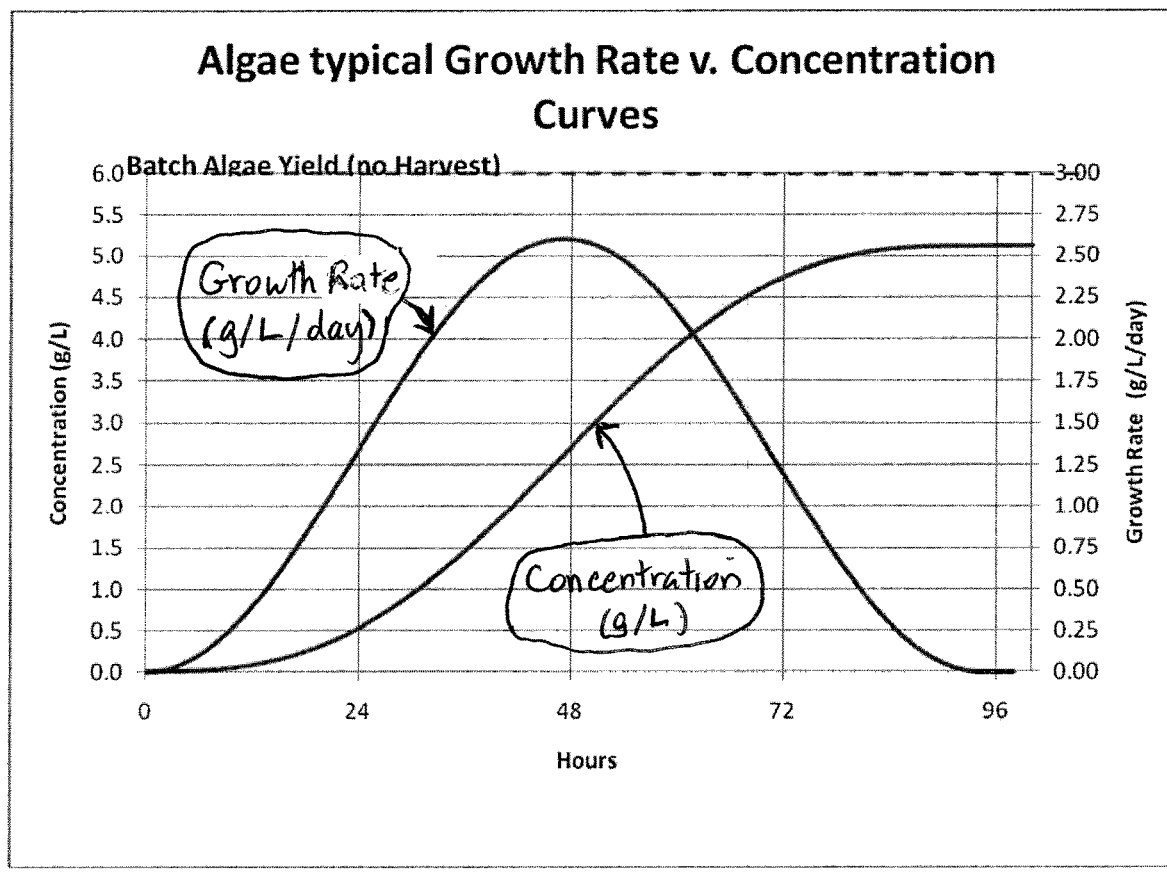
FIG. 7 is a graph generally illustrating typical algae growth rate and concentration as a function of time.

FIG. 7 illustrates how the maximum rate of growth of mass of phototrophic biomass (algae), expressed as a maximum rate of growth of mass concentration of phototrophic biomass within a photobioreactor system, is determined by measuring mass concentration of phototrophic biomass (algae) during growth of the phototrophic biomass within the system. The curves depicted in FIG. 7 are characteristic of a typical algae growth system, but the exact time and concentration limits will vary with each set-up (maximum mass concentration and maximum rate of growth of mass concentration are determined system limitations). With the knowledge of the form and behaviour of these characteristic curves, it is possible to determine these system parameters by monitoring the mass concentration (or density) in short time intervals, so that it can be converted to real-time growth rates. These density measurements and the corresponding growth estimates in real time, assist in determining the algae concentration at which the maximum growth occurs by calculating the growth acceleration (A=dG/dt) and identifying the range where this value approaches zero (see also FIGS. 9A and 9B). Once the maximum growth rate is determined, the harvesting cycle can start to effectively remove the algae growth and maintain the same consistency and growth conditions required to support the maximum growth rate for the system.

Figure 8:
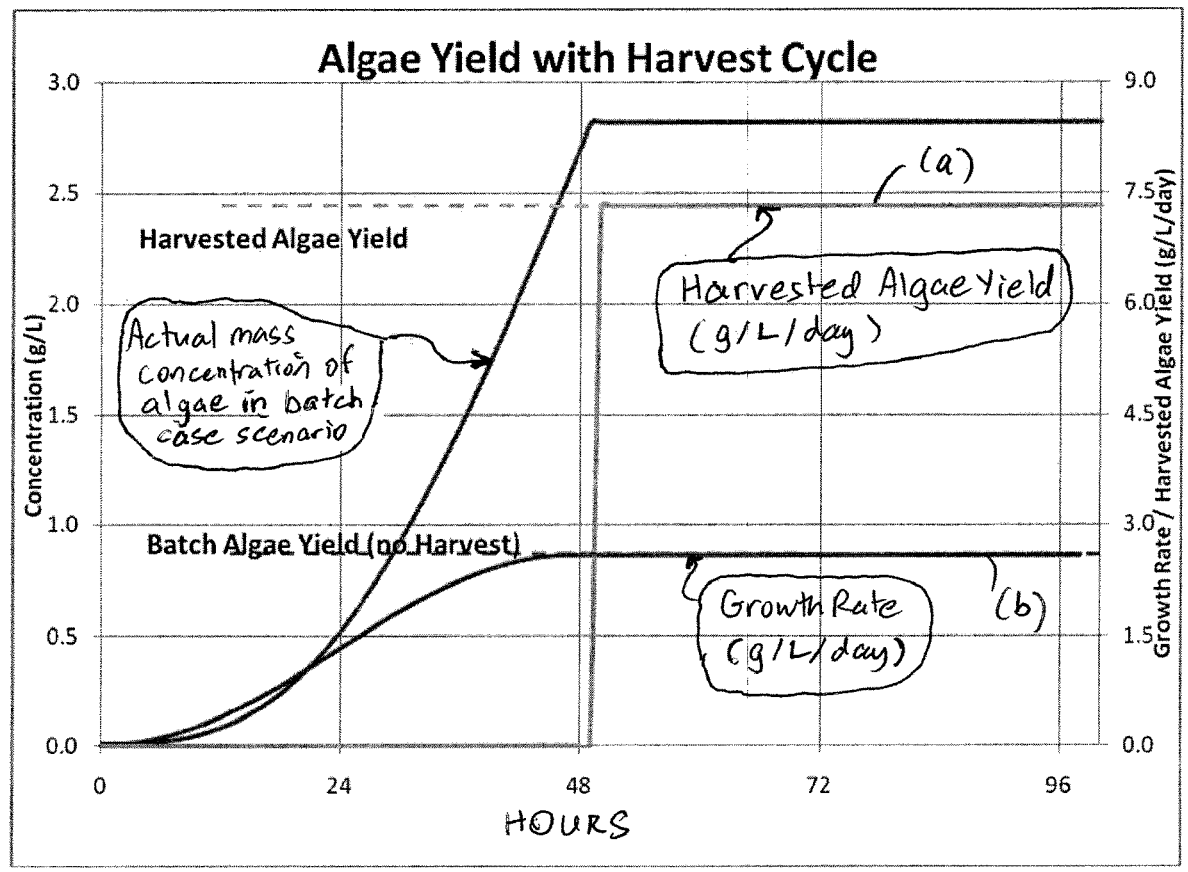
FIG. 8 is a graph generally illustrating a comparison between yield from typical harvesting of algae at the concentration correlated with maximum growth rate versus growth rate of algae in a "batch" scenario.

FIG. 8 illustrates the improved yields of phototrophic biomass (algae) when harvesting occurs while mass concentration of the phototrophic biomass (algae) within the photobioreactor is controlled at a concentration which is correlated with maximum rate of growth of mass concentration of the phototrophic biomass (algae) (a), versus the case when the phototrophic biomass (algae) is grown on a batch basis for an equivalent period of time without any harvesting (b). Importantly, the improved harvesting yield can be sustained for longer periods of time and will not end when the culture reached its maximum density (because it is never allowed to do so), when compared to the batch case scenario.

Figure 9A:
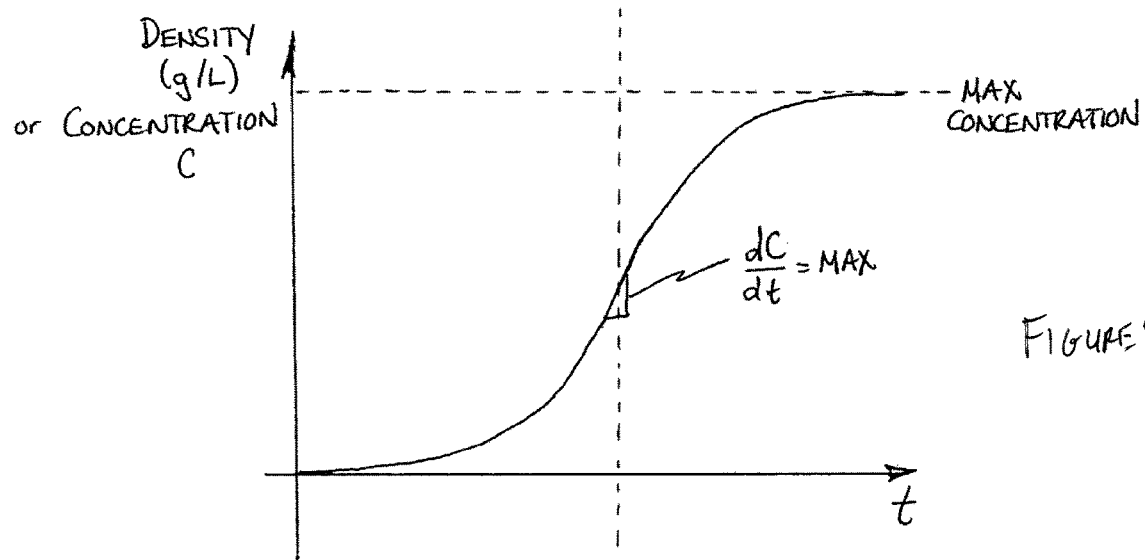
FIGS. 9A and 9B illustrates, generally, the growth of mass concentration of phototrophic biomass as a function of mass concentration of phototrophic biomass, and rate growth of mass concentration of phototrophic biomass versus mass concentration of phototrophic biomass, and how the maximum rate of growth of mass concentration of phototrophic biomass is determined.
Figure 9B:
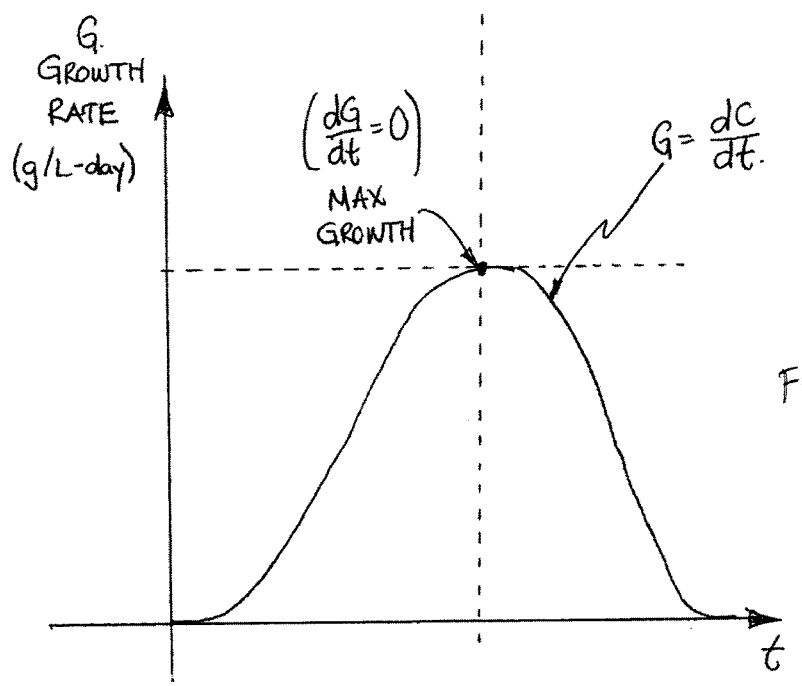

FIGS. 9A and 9B illustrate, generally, the growth of mass concentration of phototrophic biomass (algae) as a function of mass concentration of phototrophic biomass, and the maximum rate of growth of mass concentration of phototrophic biomass (algae), and the mass concentration at which this occurs and how it is determined.

FIGS. 7, 8, 9A and 9B are illustrative of algae growth systems, but their information is also relevant to other phototrophic biomass growth systems.

In some embodiments, for example, while the modulating of the rate of discharge of the production purpose phototrophic biomass from the reaction zone 10 is being effected, the volume of the reaction mixture disposed within the reaction zone is maintained constant or substantially constant for a time period of at least one (1) hour. In some embodiments, for example, the time period is at least six (6) hours. In some embodiments, for example, the time period is at least 24 hours. In some embodiments, for example, the time period is at least seven (7) days. In some embodiments, for example, while the modulating is being effected, the volume of the reaction mixture disposed within the reaction zone is maintained constant or substantially constant for a period of time such that the predetermined phototrophic biomass growth indicator value, as well as the predetermined rate of growth of phototrophic biomass, is maintained constant or substantially constant during this period, with a view to optimizing economic efficiency of the process.

In some embodiments, for example, the reaction zone 10 is disposed within a photobioreactor 10, and the production purpose phototrophic biomass is discharged from the photobioreactor 12 (and reaction zone 10) by displacement effected in response to supplying of an aqueous feed material 4 to the reaction zone 10. In other words, the supplying of an aqueous feed material 4 to the reaction zone 10 effects displacement of the production purpose phototrophic biomass from the photobioreactor 12 (and the reaction zone 10), thereby effecting discharge of the production purpose phototrophic biomass from the photobioreactor 12 (and the reaction zone 10). In some embodiments, for example, the production purpose phototrophic biomass is discharged from the photobioreactor 12 by displacement as an overflow from the photobioreactor 12.

In some embodiments, for example, the aqueous feed material 4 includes substantially no phototrophic biomass.

In other embodiments, for example, the aqueous feed material includes phototrophic biomass at a mass concentration less than the mass concentration of phototrophic biomass disposed within the reaction mixture disposed within the reaction zone 10.

In some embodiments, for example, with respect to the aqueous feed material 4, the aqueous feed material 4 is supplied as a flow from a source 6 of aqueous feed material 4. For example, the flow is effected by a prime mover, such as pump. In some embodiments, for example, the aqueous feed material includes the supplemental aqueous material supply 44. As described above, in some embodiments, for example, at least a fraction of the supplemental aqueous material supply 44 is supplied from a container 28. In this respect, in those embodiments where the supplemental aqueous material supply 44 is included within the aqueous feed material, the container functions as the source 6 of the aqueous feed material 4.

In some embodiments, for example, the aqueous feed material 4 includes the supplemental nutrient supply 42 and the supplemental aqueous material supply 44. In some of these embodiments, the aqueous feed material 4 is supplied to the reaction zone feed material 22 upstream of the reaction zone 10. In this respect, and referring to FIG. 2, and as described above, in some of these embodiments, the supplemental nutrient supply 42 and the supplemental aqueous material supply 44 are supplied to the reaction zone feed material 22 through the sparger 40 upstream of the reaction zone 10.

In some embodiments, for example, when the detected phototrophic biomass growth indicator is a mass concentration of phototrophic biomass within the reaction mixture disposed within the reaction zone 10, and the detected mass concentration of phototrophic biomass within the reaction mixture disposed within the reaction zone 10 is less than the predetermined phototrophic biomass mass concentration target value, the modulating includes effecting a decrease in the rate of discharge of mass of the production purpose phototrophic biomass from the reaction zone 10. In some of these embodiments, for example, the production purpose phototrophic biomass is discharged by displacement from the reaction zone 10 in response to the supplying of the aqueous feed material 4 to the reaction zone 10, and the decrease in the rate of discharge of mass of the production purpose phototrophic biomass from the reaction zone 10 is effected by effecting a decrease in the rate of supply (such as a volumetric rate of supply or a molar rate of supply) of, or termination of the supply of, the aqueous feed material 4 to the reaction zone 10. In this respect, when the production purpose phototrophic biomass is discharged by such displacement, in some embodiments, for example, when the detected phototrophic biomass growth indicator is a mass concentration of phototrophic biomass within the reaction mixture disposed within the reaction zone 10, upon comparing the detected mass concentration of phototrophic biomass within the reaction mixture disposed within the reaction zone 10, which is detected by the cell counter 47, with the predetermined phototrophic biomass mass concentration target value, and determining that the detected mass concentration is less than the predetermined phototrophic biomass mass concentration target value, the controller responds by effecting a decrease in the rate of supply (for example, volumetric rate of supply or a molar rate of supply) of, or termination of supply of, the aqueous feed material 4 to the reaction zone 10, which thereby effects a decrease in the mass rate of discharge of, or termination of the discharge of, the production purpose phototrophic biomass from the reaction zone 10. In some embodiments, for example, the decrease in the rate of supply of the aqueous feed material 4 to the reaction zone 10 is effected by the controller by actuating a decrease in the opening of a control valve 441 that is disposed in a fluid passage that facilitates supply of a flow of the aqueous feed material 4 from the source 6 to the reaction zone 10. In some embodiments, for example, the termination of supply of the aqueous feed material 4 to the reaction zone 10 is effected by the controller by actuating closure of a control valve 441 that is disposed in a fluid passage that facilitates supply of a flow of the aqueous feed material 4 from the source 6 to the reaction zone 10. In some embodiments, for example, the flow of the aqueous feed material 4 is being effected by a prime mover, such as a pump 281. In some embodiments, for example, the flow of the aqueous feed material 4 is being effected by gravity. In some embodiments, for example, the aqueous feed material 4 includes the supplemental aqueous material supply 44 which is supplied from the container 28. In some embodiments, the aqueous feed material 4 is the supplemental aqueous material supply 44 which is supplied from the container 28. In some of these embodiments, for example, the supplemental aqueous material supply 44 is supplied from the container 28 by the pump 281, and in other ones of these embodiments, for example, the supplemental aqueous material supply 44 is supplied from the container 28 by gravity. In some embodiments, for example, where a prime mover (such as the pump 281) is provided for effecting the flow of the aqueous feed material 4 to the reaction zone 10, the decrease in the rate of supply of the aqueous feed material 4 to the reaction zone 10 is effected by the controller actuating a decrease to the power being supplied to the prime mover 281 (such as the pump 281) to the aqueous feed material 4, such as by reducing the speed of the prime mover 281. In some embodiments, for example, where a prime mover (such as the pump 281) is provided for effecting the flow of the aqueous feed material 4 to the reaction zone 10, the termination of supply of the aqueous feed material 4 to the reaction zone 10 is effected by the controller actuating stoppage of the prime mover.

In some embodiments, for example, when the detected phototrophic biomass growth indicator is a mass concentration of phototrophic biomass within the reaction mixture disposed within the reaction zone 10, and the detected mass concentration of phototrophic biomass within the reaction mixture disposed within the reaction zone 10 is greater than the predetermined phototrophic biomass mass concentration target value, the modulating includes effecting an increase in the rate of discharge of mass of the production purpose phototrophic biomass from the reaction zone 10. In some of these embodiments, for example, the production purpose phototrophic biomass is discharged from the reaction zone 10 by displacement in response to the supplying of the aqueous feed material 4 to the reaction zone 10, and the increase in the rate of discharge of mass of the production purpose phototrophic biomass from the reaction zone 10 is effected by effecting initiation of supply of, or an increase in the rate of supply (for example, a volumetric rate of supply or a molar rate of supply) of, the aqueous feed material 4 to the reaction zone 10. In this respect, when the production purpose phototrophic biomass is discharged by such displacement, in some embodiments, for example, when the detected phototrophic biomass growth indicator is a mass concentration of phototrophic biomass in the reaction zone 10, upon comparing the detected mass concentration of phototrophic biomass within the reaction mixture disposed within the reaction zone 10, which is detected by the cell counter 47, with the predetermined phototrophic biomass mass concentration target value, and determining that the detected mass concentration is greater than the predetermined phototrophic biomass mass concentration target value, the controller responds by effecting initiation of supply of, or an increase in the rate of supply (molar rate of supply and/or volumetric rate of supply) of, the aqueous feed material 4 to the reaction zone 10, which thereby effects an increase in the rate of discharge of mass of the production purpose phototrophic biomass from the reaction zone 10. In some embodiments, for example, the initiation of supply of the aqueous feed material 4 to the reaction zone 10 is effected by the controller by actuating opening of a control valve 441 that is disposed in a fluid passage that facilitates supply of a flow of the aqueous feed material 4 from the source 6 to the reaction zone 10. In some embodiments, for example, the increase in the rate of supply of the aqueous feed material 4 to the reaction zone 10 is effected by the controller by actuating an increase in the opening of a control valve 441 that is disposed in a fluid passage that facilitates supply of a flow of the aqueous feed material 4 from the source 6 to the reaction zone 10. In some embodiments, for example, the flow of the aqueous feed material 4 is being effected by a prime mover, such as a pump 281. In some embodiments, for example, the flow of the aqueous feed material 4 is being effected by gravity. In some embodiments, for example, the aqueous feed material includes the supplemental aqueous material supply 44 which is supplied from the container 28. In some embodiments, for example, the aqueous feed material is the supplemental aqueous material supply 44 which is supplied from the container 28. In some of these embodiments, for example, the supplemental aqueous material supply 44 is supplied from the container 28 by the pump 281, and in other ones of these embodiments, for example, the supplemental aqueous material supply 44 is supplied from the container 28 by gravity. In some embodiments, for example, where a prime mover (such as the pump 281) is provided for effecting the flow of the aqueous feed material 4 to the reaction zone 10, the initiation of supply of the aqueous feed material 4 to the reaction zone 10 is effected by the controller actuating operation of the prime mover. In some embodiments, for example, where a prime mover (such as the pump 281) is provided for effecting the flow of the aqueous feed material 4 to the reaction zone 10, the increase in the rate of supply of the aqueous feed material 4 to the reaction zone 10 is effected by the controller actuating an increase to the power being supplied to the prime mover to the aqueous feed material 4.

In some embodiments, for example, the discharging of the phototrophic biomass 58 from the reaction zone 10 is effected by a prime mover that is fluidly coupled to the reaction zone 10. In this respect, in some embodiments, for example, the modulating of the rate of discharge of mass of the phototrophic biomass from the reaction zone includes:

(i) modulating the power being supplied to the prime mover effecting the discharge of the phototrophic biomass from the reaction zone 10 in response to detection of a difference between a detected phototrophic biomass growth indicator (within the reaction mixture disposed within the reaction zone) and a predetermined phototrophic biomass growth indicator target value, wherein the predetermined phototrophic biomass growth indicator target value is correlated with a predetermined rate of growth of mass of the phototrophic biomass within the reaction mixture which is disposed within the reaction zone 10 and is being exposed to the photosynthetically active light radiation, and;

(ii) while the modulating of the power supplied to the prime mover is being effected, modulating the rate of supply (for example, a volumetric rate of supply or a molar rate of supply) of the supplemental aqueous material supply 44 to the reaction zone 10 in response to detection of a difference between a detected indication of volume of reaction mixture within the reaction zone and a predetermined reaction mixture volume indication value, wherein the predetermined reaction mixture volume indication value is representative of a volume of reaction mixture within the reaction zone 10 within which growth of the phototrophic biomass is being effected within the reaction mixture at the predetermined rate of growth of mass (or mass concentration) of the phototrophic biomass while the phototrophic biomass growth indicator within the reaction mixture is disposed at the predetermined phototrophic biomass growth indicator target value.

In some embodiments, for example, the indication of volume of reaction mixture within the reaction zone 10 (or, simply, the "reaction mixture volume indication") is an upper liquid level of the reaction mixture within the reaction zone 10. In some embodiments, for example, this upper liquid level is detected with a level sensor. In this respect, in some embodiments, for example, the level sensor is provided to detect the level of the reaction mixture within the reaction zone 10, and transmit a signal representative of the detected level to a controller. The controller compares the received signal to a predetermined level value (representative of the predetermined reaction mixture volume indication value). If the received signal is less than the predetermined level value, the controller responds by effecting initiation of supply, or an increase to the rate of supply (such as a volumetric rate of supply or a molar rate of supply), of the supplemental aqueous material supply 48 to the reaction zone 10, such as by opening (in the case of initiation of supply), or increasing the opening (in the case of increasing the molar rate of supply), of a valve configured to interfere with the supply of the supplemental aqueous material supply 48 to the reaction zone 10. If the received signal is greater than the predetermined level value, the controller responds by effecting a decrease to the rate of supply (such as a volumetric rate of supply or a molar rate of supply), or termination of supply, of the supplemental aqueous material supply 48 to the reaction zone 10, such as by decreasing the opening of (in the case of decreasing the molar rate of supply), or closing the valve (in the case of terminating the supply) that is configured to interfere with the supply of the supplemental aqueous material supply 48 to the reaction zone 10. By regulating the supplying of the supplemental aqueous material supply 48 to the reaction zone 10 so as to effect the maintaining of a desired level within the reaction zone 10, make-up water is supplied to the reaction zone 10 to replace water that is discharged with the phototrophic biomass from the reaction zone 10, with a view to optimizing the rate of growth of mass of concentration of the phototrophic biomass within the reaction zone 10, and thereby optimizing the rate at which mass of the phototrophic biomass is being discharged from the reaction zone 10.

In some embodiments, for example, while the modulating of the rate of discharge of mass of the phototrophic biomass from the reaction zone 10 is being effected, the process further includes modulating the rate of supply (such as a molar rate of supply or a volumetric rate of supply) of the supplemental nutrient supply to the reaction zone in response to the detection of a difference between a detected concentration of one or more nutrients (eg. $NO_3$) within the reaction zone 10 and a corresponding predetermined target concentration value.

In some embodiments, for example, while the modulating of the rate of discharge of mass of the phototrophic biomass from the reaction zone 10 is being effected, the process further includes modulating the rate of flow (such as a molar rate of flow, or a volumetric rate of flow) of the carbon dioxide to the reaction zone 10 in response to detecting of at least one carbon dioxide processing capacity indicator. In some embodiments, for example, the detecting of at least one of the at least one carbon dioxide processing capacity indicator is effected in the reaction zone 10. The carbon dioxide processing capacity indicator which is detected is any characteristic that is representative of the capacity of the reaction zone 10 for receiving carbon dioxide and having at least a fraction of the received carbon dioxide converted in a photosynthesis reaction effected by phototrophic biomass disposed within the reaction zone. In some embodiments, for example, the carbon dioxide processing capacity indicator which is detected is a pH within the reaction zone 10. In some embodiments, for example, the carbon dioxide processing capacity indicator which is detected is a mass concentration of phototrophic biomass within the reaction zone 10.

In some embodiments, for example, while the modulating of the rate of discharge of mass of the phototrophic biomass from the reaction zone 10 is being effected, the process further includes modulating the intensity of the photosynthetically active light radiation to which the reaction mixture is exposed to, in response to a detected change in the rate (such as a molar rate, or a volumetric rate) at which the carbon dioxide is being supplied to the reaction zone 10.

In another aspect, the process further includes effecting the predetermination of the phototrophic biomass growth indicator target value. In this respect, an evaluation purpose reaction mixture that is representative of the production purpose reaction mixture and is operative for effecting photosynthesis, upon exposure to photosynthetically active light radiation, is provided, such that the phototrophic biomass of the evaluation purpose reaction mixture is an evaluation purpose phototrophic biomass that is representative of the production purpose phototrophic biomass. In some embodiments, for example, the production purpose reaction mixture further includes water and carbon dioxide, and the evaluation purpose reaction mixture further includes water and carbon dioxide. While the evaluation purpose reaction mixture disposed in the reaction zone 10 is exposed to photosynthetically active light radiation and growth of the evaluation purpose phototrophic biomass is being effected within the evaluation purpose reaction mixture, the process further includes:

(i) at least periodically detecting the phototrophic biomass growth indicator to provide a plurality of detected values of the phototrophic biomass growth indicator that have been detected during a time period ("at least periodically" means that the detecting could be done intermittently, at equally spaced intervals or at unequally spaced time intervals, or could be done continuously);

(ii) calculating growth rates of mass (or mass concentration) of the evaluation purpose phototrophic biomass based on the plurality of detected values of the phototrophic biomass growth indicator such that a plurality of growth rates of mass (or mass concentration) of the evaluation purpose phototrophic biomass are determined during the time period; and (iii) establishing a relationship between the growth rate of mass (or mass concentration) of the evaluation purpose phototrophic biomass and the phototrophic biomass growth indicator, based on the calculated growth rates and the detected values of the phototrophic biomass growth indicator upon which the calculated growth rates have been based, such that the established relationship between the growth rate of the mass (or mass concentration) of evaluation purpose phototrophic biomass and the phototrophic biomass growth indicator is representative of a relationship between the growth rate of mass (or mass concentration) of the production purpose phototrophic biomass within the reaction zone 10 and the phototrophic biomass growth indicator, and such that the relationship between the growth rate of mass (or mass concentration) of the production purpose phototrophic biomass within the reaction zone 10 and the phototrophic biomass growth indicator is thereby determined.

A predetermined growth rate is selected. The phototrophic biomass growth indicator target value is defined as the phototrophic biomass growth indicator at which the predetermined growth rate is being effected based on the determined relationship between the growth rate of mass (or mass concentration) of the production purpose phototrophic biomass within the reaction zone and the phototrophic biomass growth indicator. In this respect, the correlation between the phototrophic biomass growth indicator target value and the predetermined growth rate is also thereby effected.

In some embodiments, for example, the growth of the evaluation purpose phototrophic biomass in the reaction zone 10 is effected while the reaction zone is characterized by at least one evaluation purpose growth condition, wherein each one of the at least one evaluation purpose growth condition is representative of a production purpose growth condition by which the reaction zone 10 is characterized while growth of the production purpose phototrophic biomass, within the reaction zone 10, is being effected. In some embodiments, for example, the production purpose growth condition is any one of a plurality of production purpose growth conditions including composition of the reaction mixture, reaction zone temperature, reaction zone pH, reaction zone light intensity, reaction zone lighting regimes (eg. variable intensities), reaction zone lighting cycles (eg. duration of ON/OFF lighting cycles), and reaction zone temperature. In some embodiments, for example, providing one or more evaluation purpose growth conditions, each of which is representative of a production purpose growth condition to which the production purpose reaction mixture is exposed to while growth of the production purpose phototrophic biomass in the reaction zone 10 is being effected, promotes optimization of phototrophic biomass production.

In another aspect, while the phototrophic biomass is growing at or relatively close to the maximum growth rate within the reaction zone 10, a rate of discharge of mass of the phototrophic biomass is effected that at least approximates the rate of growth of mass of the phototrophic biomass within the reaction zone.

The reaction mixture, in the form of a production purpose reaction mixture that is operative for effecting photosynthesis upon exposure to photosynthetically active light radiation, is disposed within the reaction zone 10. The production purpose reaction mixture includes phototrophic biomass in the form of production purpose phototrophic biomass that is operative for growth within the reaction zone 10. While the reaction mixture disposed in the reaction zone 10 is exposed to photosynthetically active light radiation and growth of the production purpose phototrophic biomass is being effected within the reaction mixture, mass of production purpose phototrophic biomass is discharging from the reaction zone 10 at a rate that is within 10% of the rate at which the growth of mass of the production purpose phototrophic biomass is being effected within the reaction zone 10. The effected growth of the production purpose phototrophic biomass within the reaction zone 10 is being effected at a rate that is at least 90% of the maximum growth rate of mass of the production purpose phototrophic biomass within the reaction mixture which is disposed in reaction zone 10 and is being exposed to the photosynthetically active light radiation. In some embodiments, for example, the rate of discharge of mass of the production purpose phototrophic biomass is within 5% of the rate of growth of mass of the production purpose phototrophic biomass within the reaction zone 10. In some embodiments, for example, the rate of discharge of mass of the production purpose phototrophic biomass is within 1% of the rate of growth of mass the production purpose phototrophic biomass within the reaction zone 10. In some embodiments, for example, the effected growth of the production purpose phototrophic biomass within the reaction zone 10 is being effected at a mass growth rate of at least 95% of the maximum rate of growth of mass of the production purpose phototrophic biomass within the reaction mixture which is disposed within the reaction zone 10 and is being exposed to the photosynthetically active light radiation, and in some of these embodiments, for example, the rate of discharge of mass of the production purpose phototrophic biomass that is provided is within 5%, such as within 1%, of the rate of growth of mass of the production purpose phototrophic biomass within the reaction zone 10. In some embodiments, for example, the effected growth of the production purpose phototrophic biomass within the reaction zone 10 is being effected at a mass growth rate of at least 99% of the maximum rate of growth of mass of the production purpose phototrophic biomass within the reaction mixture which is disposed within the reaction zone 10 and is being exposed to the photosynthetically active light radiation, and in some of these embodiments, for example, the rate of discharge of mass of the production purpose phototrophic biomass that is provided is within 5%, such as within 1%, of the rate of growth of mass of the production purpose phototrophic biomass within the reaction zone 10.

In some embodiments, for example, the effecting of the growth of the production purpose phototrophic biomass includes supplying carbon dioxide to the reaction zone 10 and exposing the production purpose reaction mixture to photosynthetically active light radiation. In some embodiments, for example, the supplied carbon dioxide is supplied from the gaseous exhaust material 18 of the gaseous exhaust material producing process 20. In some embodiments, for example, the supplied carbon dioxide is supplied from the gaseous exhaust material 18 of the gaseous exhaust material producing process 20 while the gaseous exhaust material 18 is being discharged by the gaseous exhaust material producing process 20, and while at least a fraction of the gaseous exhaust material 18 is being supplied to the reaction zone feed material 22 (as the gaseous exhaust material reaction zone supply 24), and while the reaction zone feed material 22 is being supplied to the reaction zone 10. In this respect, in some embodiments, for example, the carbon dioxide is supplied to the reaction zone 10 while the growth is being effected, wherein at least a fraction of the carbon dioxide being supplied to the reaction zone is supplied from a gaseous exhaust material while the gaseous exhaust material is being discharged from a gaseous exhaust material producing process.

In some embodiments, for example, the reaction zone 10 is disposed within a photobioreactor 10, and the production purpose phototrophic biomass is discharged from the photobioreactor 12 (and the reaction zone 10) by displacement effected in response to supplying of an aqueous feed material 4 to the reaction zone 10. In other words, the supplying of an aqueous feed material 4 to the reaction zone 10 effects displacement of the production purpose phototrophic biomass from the photobioreactor 12 (and the reaction zone 10), thereby effecting discharge of the production purpose phototrophic biomass from the photobioreactor 12 (and the reaction zone 10). In some embodiments, for example, the production purpose phototrophic biomass product is discharged as an overflow from the photobioreactor.

In some embodiments, for example, the aqueous feed material 4 is supplied to the reaction zone 10 and effects displacement of the production purpose phototrophic biomass from the reaction zone 10, thereby effecting discharge of the production purpose phototrophic biomass from the reaction zone 10. In some of these embodiments, for example, the aqueous feed material 4 includes substantially no production purpose phototrophic biomass. In other ones of these embodiments, for example, the aqueous feed material 4 includes production purpose phototrophic biomass at a concentration less than the reaction zone concentration of the production purpose phototrophic biomass.

In some embodiments, for example, with respect to the aqueous feed material 4, the aqueous feed material 4 is supplied as a flow from a source 6 of aqueous feed material 4. For example, the flow is effected by a prime mover, such as pump. In some embodiments, for example, the aqueous feed material includes the supplemental aqueous material supply 44. As described above, in some embodiments, for example, at least a fraction of the supplemental aqueous material supply 44 is supplied from a container 28. In this respect, in those embodiments where the supplemental aqueous material supply 44 is included within the aqueous feed material, the container functions as the source 6 of the aqueous feed material 4.

In some embodiments, for example, the aqueous feed material 4 includes the supplemental nutrient supply 42 and the supplemental aqueous material supply 44. In some of these embodiments, the aqueous feed material 4 is supplied to the reaction zone feed material 22 upstream of the reaction zone 10. In this respect, and referring to FIG. 2, and as described above, in some of these embodiments, the supplemental nutrient supply 42 and the supplemental aqueous material supply 44 are supplied to the reaction zone feed material 22 through the sparger 40 upstream of the reaction zone 10.

In some of these embodiments, for example, and as described above, the discharging of the phototrophic biomass 58 from the reaction zone 10 is effected by a prime mover that is fluidly coupled to the reaction zone 10. In some embodiments, for example, supplemental aqueous material supply 44 is supplied to the reaction zone 10 so as to maintain a predetermined volume of reaction mixture within the reaction zone 10, as described above.

In another aspect, discharging of the phototrophic biomass is effected at a rate that matches the growth rate of mass of the phototrophic biomass within the reaction zone 10. In some embodiments, for example, this mitigates shocking of the phototrophic biomass in the reaction zone 10. With respect to some embodiments, for example, the discharging of the phototrophic biomass is controlled through the rate of supply (such as a volumetric rate of supply, or a molar rate of supply) of supplemental aqueous material supply 44, which influences the displacement from the photobioreactor 12 of the phototrophic biomass-comprising product 500 from the photobioreactor 12. For example, the product 500, including the phototrophic biomass, is discharged as an overflow. In some of these embodiments, the upper portion of phototrophic biomass suspension in the reaction zone 10 overflows the photobioreactor 12 (for example, the phototrophic biomass is discharged through an overflow port of the photobioreactor 12) to provide the phototrophic biomass-comprising product 500. In other embodiments, for example, the discharging of the product 500 is controlled with a valve disposed in a fluid passage which is fluidly communicating with an outlet of the photobioreactor 12.

In some embodiments, for example, the discharging of the product 500 is effected continuously. In other embodiments, for example, the discharging of the product is effected periodically. In some embodiments, for example, the discharging of the product is designed such that the concentration of mass of the biomass in the phototrophic biomass-comprising product 500 is maintained at a relatively low concentration. In those embodiments where the phototrophic biomass includes algae, it is desirable, for some embodiments, to effect discharging of the product 500 at lower concentrations to mitigate against sudden changes in the molar growth rate of the algae in the reaction zone 10. Such sudden changes could effect shocking of the algae, which thereby contributes to lower yield over the longer term. In some embodiments, where the phototrophic biomass is algae and, more specifically, *scenedesmus obliquus*, the concentration of this algae in the phototrophic biomass-comprising product 500 could be between 0.5 and 3 grams per litre. The desired concentration of the discharged algae product 500 depends on the strain of algae such that this concentration range changes depending on the strain of algae. In this respect, in some embodiments, maintaining a predetermined water content in the reaction zone is desirable to promote the optimal growth of the phototrophic biomass, and this can also be influenced by controlling the supply of the supplemental aqueous material supply 44.

The phototrophic biomass-comprising product 500 includes water. In some embodiments, for example, the phototrophic biomass-comprising product 500 is supplied to a separator 52 for effecting removal of at least a fraction of the water from the phototrophic biomass-comprising product 500 to effect production of an intermediate concentrated phototrophic biomass-comprising product 34 and a recovered aqueous material 72 (in some embodiments, substantially water). In some embodiments, for example, the separator 52 is a high speed centrifugal separator 52. Other suitable examples of a separator 52 include a decanter, a settling vessel or pond, a flocculation device, or a flotation device. In some embodiments, the recovered aqueous material 72 is supplied to a container 28, such as a container, for re-use by the process.

In some embodiments, for example, after the product 500 is discharged, and before being supplied to the separator 52, the phototrophic biomass-comprising product 500 is supplied to a harvest pond 54. The harvest pond 54 functions both as a buffer between the photobioreactor 12 and the separator 52, as well as a mixing vessel in cases where the harvest pond 54 receives different biomass strains from multiple photobioreactors. In the latter case, customization of a blend of biomass strains can be effected with a predetermined set of characteristics tailored to the fuel type or grade that will be produced from the blend.

As described above, the container 28 provides a source of supplemental aqueous material supply 44 for the reaction zone 10, and functions to contain the supplemental aqueous material supply 44 before supplemental aqueous material supply 44 is supplied to the reaction zone 10. Loss of water is experienced in some embodiments as moisture in the final phototrophic biomass-comprising product 36, as well as through evaporation in the dryer 32. The supplemental aqueous material in the container 28, which is recovered from the process, can be supplied to the reaction zone 10 as the supplemental aqueous material supply 44. In some embodiments, for example, the supplemental aqueous material supply 44 is supplied to the reaction zone 10 with the pump 281. In other embodiments, the supply can be effected by gravity, if the layout of the process equipment of the system, which embodies the process, permits. As described above, the supplemental aqueous material recovered from the process includes at least one of: (a) aqueous material 70 which has been condensed from the reaction zone feed material 22 while the reaction zone feed material 22 is being cooled before being supplied to the reaction zone 10, and (b) aqueous material 72 which has been separated from the phototrophic biomass-comprising product 500. In some embodiments, for example, the supplemental aqueous material supply 44 is supplied to the reaction zone 10 to effect displacement of the product 500 from the reaction zone. In some embodiments, for example, the product 500 is displaced as an overflow from the photobioreactor 12. In some embodiments, for example, the supplemental aqueous material supply 44 is supplied to the reaction zone 10 to effect a desired predetermined concentration of phototrophic biomass within the reaction zone by diluting the reaction mixture disposed within the reaction zone.

Examples of specific structures which can be used as the container 28 by allowing for containment of aqueous material recovered from the process, as above-described, include, without limitation, tanks, ponds, troughs, ditches, pools, pipes, tubes, canals, and channels.

In some embodiments, for example, the supplying of the supplemental aqueous material supply 44 to the reaction zone 10 is effected while the gaseous exhaust material 18 is being discharged by the gaseous exhaust material producing process 20, and while the gaseous exhaust material reaction zone supply 24 is being supplied to the reaction zone feed material 22. In some embodiments, for example, the exposing of the carbon dioxide-enriched phototrophic biomass disposed in the aqueous medium to photosynthetically active light radiation is effected while the supplying of the supplemental aqueous material supply to the reaction zone 10 is being effected.

In some embodiments, for example, the supplying of the supplemental aqueous material supply 44 to the reaction zone 10 is modulated based upon the detection of a deviation of a value of a phototrophic biomass growth indicator from that of a predetermined target value of the process parameter, wherein the predetermined target value of the phototrophic biomass growth indicator is based upon a predetermined growth rate of mass of the phototrophic biomass within the reaction zone. The detection of a deviation of the phototrophic biomass growth indicator from that of the target value of the phototrophic biomass growth indicator, and the modulation of the supplying of the supplemental aqueous material supply 44 to the reaction zone 10 in response to the detection, is discussed above.

In some embodiments, for example, supply of the supplemental aqueous material supply 44 to the reaction zone 10 is dictated by the mass concentration of phototrophic biomass. In this respect, mass concentration of the phototrophic biomass in the reaction zone 10, or an indication of mass concentration of the phototrophic biomass in the reaction zone 10, is detected by a cell counter, such as the cell counters described above. The detected mass concentration of the phototrophic biomass, or the detected indication of mass concentration of phototrophic biomass, is transmitted to the controller, and when the controller determines that the detected mass concentration exceeds a predetermined high mass concentration value, the controller responds by initiating the supply, or increasing the rate of supply (such as a volumetric rate of supply, or a molar rate of supply), of the supplemental aqueous material supply 44 to the reaction zone 10. In some embodiments, for example, the initiating of the supply, or increasing the rate of supply, of the supplemental aqueous material supply 44 to the reaction zone 10 includes actuating a prime mover, such as the pump 281, to initiate supply, or an increase in the molar rate of supply, of the supplemental aqueous material supply 44 to the reaction zone 10. In some embodiments, for example, the effecting supply, or increasing the rate of supply, of the supplemental aqueous material supply 44 to the reaction zone 10 includes initiating the opening, or increase the opening, of a valve that is configured to interfere with supply of the supplemental aqueous material supply 44 from the container 28 to the reaction zone 10.

In some embodiments, for example, when the upper level of the contents of the reaction zone 10 within the photobioreactor 12 becomes disposed below a predetermined minimum level, the initiation of the supply of, or an increase to the rate of supply (such as a volumetric rate of supply, or a molar rate of supply) of, the supplemental aqueous material supply 44 (which has been recovered from the process) is effected to the reaction zone 10. In some of these embodiments, for example, a level sensor 76 is provided for detecting the position of the upper level of the contents of the reaction zone 10 within the photobioreactor, and transmitting a signal representative of the upper level of the contents of the reaction zone 10 to the controller. Upon the controller comparing a received signal from the level sensor 76, which is representative of the upper level of the contents of the reaction zone 10, to a predetermined low level value, and determining that the detected upper level of the contents of the reaction zone is below the predetermined low level value, the controller effects the initiation of the supply of, or an increase to the rate of supply of, the supplemental aqueous material supply 44. When the supply of the supplemental aqueous material supply 44 to the reaction zone 10 is effected by a pump 281, the controller actuates the pump 281 to effect the initiation of the supply, or an increase to the rate of supply, of the supplemental aqueous material supply 44 to the reaction zone 10. When the supply of the supplemental aqueous material supply 44 to the reaction zone 10 is effected by gravity, the controller actuates the opening of a valve to effect the initiation of the supply, or an increase to the molar rate of supply, of the supplemental aqueous material supply 44 to the reaction zone 10. For example, control of the position of the upper level of the contents of the reaction zone 10 is relevant to operation for some of those embodiments where the discharging of the phototrophic biomass 58 from the reaction zone 10 is effected from a lower portion of the reaction zone 10, such as when the discharging of the phototrophic biomass 58 from the reaction zone 10 is effected by a prime mover that is fluidly coupled to the reaction zone 10, as discussed above. In those embodiments where the discharging of the phototrophic biomass 58 from the reaction zone 10 is effected by an overflow, in some of these embodiments, control of the position of the upper level of the contents of the reaction zone 10 is relevant during the "seeding stage" of operation of the photobioreactor 12.

In some embodiments, for example, where the discharging of the product 500 is controlled with a valve disposed in a fluid passage which is fluidly communicating with an outlet of the photobioreactor 12, mass concentration of phototrophic biomass in the reaction zone is detected by a cell counter 47, such as the cell counters described above. The detected mass concentration of phototrophic biomass is transmitted to the controller, and when the controller determines that the detected molar phototrophic biomass concentration exceeds a predetermined high phototrophic biomass mass concentration value, the controller responds by initiating opening, or increasing the opening, of the valve to effect an increase in the rate of discharging of mass of the product 500 from the reaction zone 10.

In some embodiments, for example, a source of additional make-up water 68 is provided to mitigate against circumstances when the supplemental aqueous material supply 44 is insufficient to make-up for water which is lost during operation of the process. In this respect, in some embodiments, for example, the supplemental aqueous material supply 44 is mixed with the reaction zone feed material 22 in the sparger 40. Conversely, in some embodiments, for example, accommodation for draining of the container 28 to drain 66 is provided to mitigate against the circumstances when aqueous material recovered from the process exceeds the make-up requirements.

In some embodiments, for example, a reaction zone gaseous effluent product 80 is discharged from the reaction zone 10. At least a fraction of the reaction zone gaseous effluent 80 is recovered and supplied to a reaction zone 110 of a combustion process unit operation 100. As a result of the photosynthesis being effected in the reaction zone 10, the reaction zone gaseous effluent 80 is rich in oxygen relative to the gaseous exhaust material reaction zone supply 24. The gaseous effluent 80 is supplied to the combustion zone 110 of a combustion process unit operation 100 (such as a combustion zone 110 disposed in a reaction vessel), and, therefore, functions as a useful reagent for the combustion process being effected in the combustion process unit operation 100. The reaction zone gaseous effluent 80 is contacted with combustible material (such as carbon-comprising material) in the combustion zone 100, and a reactive process is effected whereby the combustible material is combusted. Examples of suitable combustion process unit operations 100 include those in a fossil fuel-fired power plant, an industrial incineration facility, an industrial furnace, an industrial heater, an internal combustion engine, and a cement kiln.

In some embodiments, for example, the contacting of the recovered reaction zone gaseous effluent 80 with a combustible material is effected while the gaseous exhaust material 18 is being discharged by the gaseous exhaust material producing process 20 and while the gaseous exhaust material reaction zone supply 24 is being supplied to the reaction zone feed material 22. In some embodiments, for example, the contacting of the recovered reaction zone gaseous effluent with a combustible material is effected while the gaseous exhaust material reaction zone supply 24 is being supplied to the reaction zone feed material 22. In some embodiments, for example, the contacting of the recovered reaction zone gaseous effluent with a combustible material is effected while the reaction zone feed material is being supplied to the reaction zone. In some embodiments, for example, the exposing of the carbon dioxide-enriched phototrophic biomass disposed in the aqueous medium to photosynthetically active light radiation is effected while the contacting of the recovered reaction zone gaseous effluent with a combustible material is being effected.

The intermediate concentrated phototrophic biomass-comprising product 34 is supplied to a dryer 32 which supplies heat to the intermediate concentrated phototrophic biomass-comprising product 34 to effect evaporation of at least a fraction of the water of the intermediate concentrated phototrophic biomass-comprising product 34, and thereby effect production of a final phototrophic biomass-comprising product 36. As discussed above, in some embodiments, the heat supplied to the intermediate concentrated phototrophic biomass-comprising product 34 is provided by a heat transfer medium 30 which has been used to effect the cooling of the reaction zone feed material 22 prior to supply of the reaction zone feed material 22 to the reaction zone 10. By effecting such cooling, heat is transferred from the reaction zone feed material 22 to the heat transfer medium 30, thereby raising the temperature of the heat transfer medium 30. In such embodiments, the intermediate concentrated phototrophic biomass-comprising product 34 is at a relatively warm temperature, and the heat requirement to effect evaporation of water from the intermediate concentrated phototrophic biomass-comprising product 34 is not significant, thereby rendering it feasible to use the heated heat transfer medium 30 as a source of heat to effect the drying of the intermediate concentrated phototrophic biomass-comprising product 34. As discussed above, after heating the intermediate concentrated phototrophic biomass-comprising product 34, the heat transfer medium 30, having lost some energy and becoming disposed at a lower temperature, is recirculated to the heat exchanger 26 to effect cooling of the reaction zone feed material 22. The heating requirements of the dryer 32 is based upon the rate of supply of mass of intermediate concentrated phototrophic biomass-comprising product 34 to the dryer 32. Cooling requirements (of the heat exchanger 26) and heating requirements (of the dryer 32) are adjusted by the controller to balance the two operations by monitoring flowrates (the molar and/or volumetric flowrates) and temperatures of each of the reaction zone feed material 22 and the rate of production of the product 500 through discharging of the product 500 from the photobioreactor.

In some embodiments, changes to the phototrophic biomass growth rate effected by changes to the rate of supply of the gaseous exhaust material reaction zone supply 24 to the reaction zone material feed 22 are realized after a significant time lag (for example, in some cases, more than three (3) hours, and sometimes even longer) from the time when the change is effected to the rate of supply of the gaseous exhaust material reaction zone supply 24 to the reaction zone feed material 22. In comparison, changes to the thermal value of the heat transfer medium 30, which are based on the changes in the rate of supply (the molar rate of supply and/or the volumetric rate of supply) of the gaseous exhaust material reaction zone supply 24 to the reaction zone feed material 22, are realized more quickly. In this respect, in some embodiments, a thermal buffer is provided for storing any excess heat (in the form of the heat transfer medium 30) and introducing a time lag to the response of the heat transfer performance of the dryer 32 to the changes in the gaseous exhaust material reaction zone supply 24. In some embodiments, for example, the thermal buffer is a heat transfer medium storage tank. Alternatively, an external source of heat may be required to supplement heating requirements of the dryer 32 during transient periods of supply of the gaseous exhaust material reaction zone supply 24 to the reaction zone material 22. The use of a thermal buffer or additional heat may be required to accommodate changes to the rate of growth of the phototrophic biomass, or to accommodate start-up or shutdown of the process. For example, if growth of the phototrophic biomass is decreased or stopped, the dryer 32 can continue operating by using the stored heat in the buffer until it is consumed, or, in some embodiments, use a secondary source of heat.

Further embodiments will now be described in further detail with reference to the following non-limitative example.

Example 1

A prophetic example, exemplifying an embodiment of determining a target value of a phototrophic biomass growth indicator (eg. algae concentration in the reaction zone of a photobioreactor), and effecting operation of an embodiment of the above-described process, including modulating the molar rate of discharge of the phototrophic biomass-comprising product from the reaction zone based on a deviation of a detected value of the process parameter from the target value, will now be described.

Initially, an initial algae concentration in an aqueous medium, with suitable nutrients, is provided in a reaction zone of a photobioreactor. Gaseous carbon dioxide is supplied to the reaction zone, and the reaction zone is exposed to light from a light source (such as LEDs), to effect growth of the algae. When algae concentration in the reaction zone reaches 0.5 grams per litre, water is flowed to the reaction zone of the photobioreactor to effect harvesting of the algae by effecting overflow of the reactor contents, and an initial target algae concentration is set at 0.5 grams per litre. Initially, the supplied water is flowed at a relatively moderate and constant rate such that the half (½) of the volume of the photobioreactor is exchanged per day, as it is found that periodically replacing water volume within the reaction zone with fresh water promotes growth of the algae and enables attaining the target value in a shorter period of time. If the algae growth rate is lower than the dilution rate, and the detected algae concentration drops at least 2% from the algae concentration set point at any time during this determination exercise, the control system will stop or reduce the dilution rate to avoid further dilution of the algae concentration in the reaction zone. If the algae growth rate is higher than the dilution rate, the algae concentration will increase above the initial algae concentration set point, and the control system will increase the algae concentration set point so as to keep pace with the increasing algae concentration, while maintaining the same dilution rate. For example, the algae concentration may increase to 0.52 grams per litre, at which point the control system will increase the algae concentration set point to 0.51. The control system continues to monitor the increase in algae concentration and, in parallel, increasing the target algae concentration. When a maximum change in the algae growth rate has been detected, the target algae concentration is locked at its existing value to become the target value, and dilution rate is then modulated so that harvesting of the algae is effected at a rate which is equivalent to the growth rate of the algae within the photobioreactor when the algae concentration is at the target value.

Algae growth rate corresponds with algae concentration. When a considerable change in the algae growth rate is detected, this is indicative of growth of algae within the reaction zone at, or close to, its maximum rate, and this growth rate corresponds to an algae concentration at the target value. In this respect, by maintaining algae concentration in the reaction zone at the target value by controlling dilution rate, algae growth is maintained at or close to the maximum, and, as a corollary, over time, the rate of discharge of algae is optimized.

In the above description, for purposes of explanation, numerous details are set forth in order to provide a thorough understanding of the present disclosure. However, it will be apparent to one skilled in the art that these specific details are not required in order to practice the present disclosure. Although certain dimensions and materials are described for implementing the disclosed example embodiments, other suitable dimensions and/or materials may be used within the scope of this disclosure. All such modifications and variations, including all suitable current and future changes in technology, are believed to be within the sphere and scope of the present disclosure. All references mentioned are hereby incorporated by reference in their entirety.

The invention claimed is:

1. A process for growing phototrophic biomass in a reaction zone, wherein the phototrophic biomass includes at least one phototrophic organism selected from algae, a plant cell, and a microorganism, wherein the reaction zone includes a reaction mixture that is operative for effecting photosynthesis upon exposure to photosynthetically active light radiation, wherein the reaction mixture includes phototrophic biomass that is operative for growth within the reaction zone, comprising:
while exposing the reaction mixture disposed in the reaction zone to photosynthetically active light radiation and growth of the phototrophic biomass is being effected within the reaction mixture:
supplying an aqueous mixture into the reaction zone, with effect that a produced biomass of the phototrophic biomass is discharged by displacement from the reaction zone;
wherein the growth of mass of the phototrophic biomass within the reaction zone is being effected at a rate that is at least 90% of a maximum rate of growth of mass of the phototrophic biomass within the reaction mixture which is disposed in the reaction zone and is being exposed to the photosynthetically active light radiation.

2. The process as claimed in claim 1;
wherein the effecting of the growth of the phototrophic biomass includes supplying carbon dioxide to the reaction zone and exposing the reaction mixture to photosynthetically active light radiation.

3. The process as claimed in claim 1;
wherein the growth of mass of the phototrophic biomass within the reaction zone is being effected at a rate that is at least 95% of the maximum rate of growth of mass of the phototrophic biomass within the reaction mixture which is disposed in reaction zone and is being exposed to the photosynthetically active light radiation.

4. The process as claimed in claim 1;
wherein the growth of mass of the phototrophic biomass within the reaction zone is being effected at a rate that is at least 99% of the maximum rate of growth of mass of the phototrophic biomass within the reaction mixture which is disposed in reaction zone and is being exposed to the photosynthetically active light radiation.

5. The process as claimed in claim 1;
wherein the discharging of the produced biomass from the reaction zone is effected at a rate that is within 5% of the rate at which the growth of mass of the phototrophic biomass is being effected within the reaction zone.

6. The process as claimed in claim 1;
wherein the discharging of the produced biomass from the reaction zone is effected at a rate that is within 1% of the rate at which the growth of mass of the phototrophic biomass is being effected within the reaction zone.

7. The process as claimed in claim 1;
wherein the reaction zone is disposed within a photobioreactor, and wherein the produced biomass is included in an overflow from the photobioreactor.

* * * * *